(12) United States Patent
De Haën et al.

(10) Patent No.: US 7,989,417 B2
(45) Date of Patent: Aug. 2, 2011

(54) LINKERS FOR RADIOPHARMACEUTICAL COMPOUNDS

(75) Inventors: Christoph De Haën, Borromeo (IT);
Adrian D. Nunn, Lamberville, NJ (US);
Rolf E. Swenson, Princeton, NJ (US)

(73) Assignee: Bracco Imaging S.p.A., Milan (IT)

( * ) Notice: Subject to any disclaimer, the term of this patent is extended or adjusted under 35 U.S.C. 154(b) by 641 days.

(21) Appl. No.: 10/542,396

(22) PCT Filed: Dec. 24, 2003

(86) PCT No.: PCT/US03/41656
§ 371 (c)(1),
(2), (4) Date: Feb. 27, 2006

(87) PCT Pub. No.: WO2004/062574
PCT Pub. Date: Jul. 29, 2004

(65) Prior Publication Data
US 2006/0241018 A1    Oct. 26, 2006

Related U.S. Application Data

(60) Provisional application No. 60/439,722, filed on Jan. 13, 2003.

(51) Int. Cl.
*A61K 38/28* (2006.01)
(52) U.S. Cl. .............................. 514/3; 514/12; 530/328
(58) Field of Classification Search .................. None
See application file for complete search history.

(56) References Cited

U.S. PATENT DOCUMENTS

| | | | |
|---|---|---|---|
| 4,885,363 A | 12/1989 | Tweedle | |
| 4,988,496 A | 1/1991 | Srinvasan et al. | |
| 5,068,222 A | 11/1991 | Camble et al. | |
| 5,217,955 A | 6/1993 | Bogden et al. | |
| 5,244,883 A | 9/1993 | Cai et al. | |
| 5,369,094 A | 11/1994 | Schally et al. | |
| 5,410,018 A | 4/1995 | Spindel et al. | |
| 5,428,018 A | 6/1995 | Edwards et al. | |
| 5,428,019 A | 6/1995 | Edwards et al. | |
| 5,534,497 A | 7/1996 | Verbruggen | |
| 5,620,955 A | 4/1997 | Knight et al. | |
| 5,620,959 A | 4/1997 | Leban et al. | |
| 5,646,272 A | 7/1997 | Kramer et al. | |
| 5,686,410 A | 11/1997 | Albert et al. | |
| 5,753,206 A * | 5/1998 | McBride et al. ............. | 424/1.69 |
| 5,834,433 A | 11/1998 | Krstenansky | |
| 5,965,695 A | 10/1999 | Simon et al. | |
| 6,075,121 A | 6/2000 | Simon et al. | |
| 6,153,729 A | 11/2000 | Stein et al. | |
| 6,200,546 B1 | 3/2001 | Hoffman et al. | |
| 6,461,588 B1 | 10/2002 | Anelli et al. | |
| 2003/0224998 A1 | 12/2003 | Reubi et al. | |

FOREIGN PATENT DOCUMENTS

| | | | |
|---|---|---|---|
| WO | WO91/01144 | | 2/1991 |
| WO | WO96/03427 | | 2/1996 |
| WO | WO 98/02192 | * | 1/1998 |
| WO | 99/55376 | | 11/1999 |
| WO | 01/09163 | | 2/2001 |
| WO | PCT/EP01/01971 | * | 2/2001 |
| WO | 01/64708 | | 9/2001 |
| WO | WO 01/64708 | * | 9/2001 |
| WO | WO 01/76531 A2 | | 10/2001 |
| WO | 02/087597 | | 11/2002 |

OTHER PUBLICATIONS

Betebenner et al. "Hepatobiliary delivery of polyaminopolycarboxylate chelates: synthesis and characterization of a cholic acid conjugate of EDTA and biodistribution and imaging studies with its indium-111 chelate" Bioconjugate Chemistry vol. 2, No. 2, 1991 pp. 117-123.
Supplementary European Search Report for European Application No. 03808615, May 2, 2007.
Giblin et al. (1998), Proc. Natl. Aca. Sci., USA, vol. 95, pp. 12814-12818.
Walsh et al., Western Journal of Medicine, vol. 155, pp. 152-163, 1991.
Heppeler et al., Receptor Targeting for Tumor Localization and Therapy with Radiopeptides. Current Medicinal Chemistry 2000, 7:971-994.
Sethi et al., Growth of small cell lung cancer cells: stimulation by multiple neuropeptides and inhibition by broad spectrum antagonists in vitro and in vivo, Cancer Res. May 1, 1992;52(9 Suppl):2737s-2742s.
Halmos, T., Wittliff, J.L., and Schally, A.V., Characterization of bombesin/gastrin releasing peptide receptors on human breast cancer and their Relationship to steroid receptor expression, Cancer Research 55:280-287, 1995.
Kelly, K., Kane, M.A., and Bunn, P.A., "Growth factors in lung cancer: Possible etiologic role and clinical target", Medical and Pediatric Oncology 19:449-458, 1991.
Jensen, R.T., Mrozinski, J.E., and Coy, D.H., "Bombesin receptor antagonists: Different classes and cellular basis of action", Recent Results in Cancer Research 129:87-113, 1993.
Reile, H., Armatis, P.E., and Schally, A.V., Characterization of high-affinity receptors for bombesin/gastrin releasing peptide on the human prostate cancer cell lines PC-3 and DU-145: internalization of receptor bound 125I-(Tyr4) bombesin by tumor cells, Prostate, Jul. 1994;25(1):29-38.

(Continued)

*Primary Examiner* — Christopher R. Tate
*Assistant Examiner* — Roy Teller
(74) *Attorney, Agent, or Firm* — Kramer Levin Naftalis & Frankel LLP

(57) ABSTRACT

A new and improved method for extending the half life of pharmaceutical compounds for use in diagnostic imaging or therapy uses a novel linker to attach a diagnostic or therapeutic moiety to a targeting peptide or another diagnostic or therapeutic moiety. The resulting compound may have the general formula M-N-O-P-Q, wherein M is the diagnostic or therapeutic moiety, N-O-P is the linker of the present invention, and Q is the targeting peptide. In another embodiment the compounds may have the formula M-N-O-P-M, wherein M is independently a diagnostic or therapeutic moiety and N-O-P is the linker of the invention. Methods for imaging or treating a patient using the compounds of the invention are also provided. Methods and kits for preparing a diagnostic imaging agent from the compound are further provided. Methods for radiotherapy of a patient using the compounds are further provided, as are methods for preparing a radiotherapeutic agent from the compounds.

14 Claims, 29 Drawing Sheets

OTHER PUBLICATIONS

Schutte, J., and Seeber, S., "Bombesin antagonists: Experimental and clinical results", Recent Results in Cancer Research 129:115-129, 1993.

Walsh, J.H., Karnes, W.E., Cuttitta, F., and Walker, A., "Autocrine growth factors and solid tumor malignancy", Western Journal of Medicine 155: 152-163, 1991.

Leban, et al., Potent gastrin-releasing peptide (GRP) antagonists derived from GRP (19-27) with a C-terminal DPro psi [CH2NH]Phe-NH2 and N-terminal aromatic residues, J Med Chem. Feb. 18, 1994;37(4):439-45.

Li, et al.; In-Vivo and In-Vitro Characterization of a Rh-105-Tetrathiamacrocycle Conjugate of a Bombesin Analogue, Proceedings of the 43rd Annual Meeting, vol. 37, No. 5, May 1996 Supplement, p. 61.

Zhu, et al.; Binding, internalization, and processing of bombesin by rat pancreatic acini, Bombesin Binding and Internalization, 1991, pp. G57-G64.

Moody, et al.; BW1023U90: A new GRP Receptor Antagonist for Small-Cell Lung Cancer Cells, Peptides vol. 17, No. 8, pp. 1337-1343, 1996.

Moody, et al.; A GRP Receptor Antagonist Which Inhibits Small-Cell Lung Cancer Growth; Life Sciences, vol. 56, No. 7, pp. 521-529, 1995.

Seifert, et al.; No Carrier Added Preparations of '3+1' Mixed-ligand 99mTc Complexes, Appl. Radiat. Isot. vol. 49, Nos. 1-2, pp. 5-11, 1998.

Smith, et al.; In Vivo and In Vitro Characterization of Novel Water-Soluble Dithio-Bisphosphine 99mTc Complexes, Nuclear Medicine & Biology, vol. 24, pp. 685-691, 1977.

Coy et al, "Short Chain Pseudopeptide bombesin receptor antagonists with enhanced binding affinities for pancreatic Acinar and swiss 3T3 cells display strong Antimitotic activity" J. Biol. Chem., vol. 264, No. 25, pp. 14691-14697, 1989.

Thomas et al., Antitumoral Activity of Bombesin Analogues on Small Cell Lung Cancer Xenografts: Relationship with Bombesin Receptor Expression, Cancer Res. Sep. 15, 1992;52(18):4872-7.

Radulovic et al., Inhibitory effects of antagonists of bombesin/gastrin releasing peptide (GRP) and somatostatin analog (RC-160) on growth of HT-29 human colon cancers in nude mice, Acta Oncol. 1994;33(6):693-701.

Qin, et al., Inhibitory effect of bombesin receptor antagonist RC-3095 on the growth of human pancreatic cancer cells in vivo and in vitro, Cancer Res. Feb. 15, 1994;54(4):1035-41.

Qin, et al., Antagonists of bombesin/gastrin-releasing peptide inhibit growth of SW-1990 human pancreatic adenocarcinoma and production of cyclic AMP, Int J Cancer. Oct. 9, 1995;63(2):257-62.

Cai et al., Potent Bombesin antagonists with C-Terminal Leu-(CH2-N)-Tac-NH2 or its Derivatives, (1994) Proc. Natl. Acad. Sci., 91:12664-12668.

Radulovic, et al., Biological effects and receptor binding affinities of new pseudononapeptide bombesin/GRP receptor antagonists with N-terminal D-Trp or D-Tpi, Int J Pept Protein Res. Dec. 1991;38(6):593-600.

Staley, et al., [Des-Met14]bombesin analogues function as small cell lung cancer bombesin receptor antagonists, Peptides. Jan.-Feb. 1991;12(1):145-9.

Wang et al., Desmethionine alkylamide bombesin analogues: a new class of bombesin receptor antagonists with potent antisecretory activity in pancreatic acini and antimitotic activity in Swiss 3T3 cells, Biochemistry. Jan. 23, 1990;29(3):616-22.

Wang, Knezetic, Schally, Pour, Adrian; Bombesin May Stimulate Proliferation of Human Pancreatic Cancer Cells Through an Autocrine Pathway, Int. J. Cancer: 68, 528-534 (1996).

Yano, Pinski, Groot, Schally, Stimulation by bombesin and inhibition by bombesin/gastrin-releasing peptide antagonist RC-3095 of growth of human breast cancer cell lines, Cancer Res. Aug. 15, 1992;52(16):4545-7.

Kane, Auguayo, Portanova, Ross, Holley, Kelly, Miller, Isolation of the bombesin/gastrin-releasing peptide receptor from human small cell lung carcinoma NCI-H345 cells, J Biol Chem. May 25, 1991;266(15):9486-93.

Schuller, Receptor-mediated mitogenic signals and lung cancer, Cancer Cells. Dec. 1991;3(12):496-503.

Halmos et al., Characterization of bombesin/gastrin-releasing peptide receptors in human breast cancer and their relationship to steroid receptor expression, Cancer Res. Jan. 15, 1995;55(2):280-7.

Hajri et al., Gastrin-releasing peptide: in vivo and in vitro growth effects on an acinar pancreatic carcinoma, Cancer Res. Jul. 1, 1992;52(13):3726-32.

Fritzberg, et al., Radiolabeling of Antibodies for Targeted Diagnostics, Handbook of Targeted Delivery of Imaging Agents (ed) V.P. Torchilin, CRC Press, Boca Raton, Florida, Chapter 6, pp. 83-101, 1995.

Radulovic, et al., The Binding of Bombesin and Somatostatin and Their Analogs to Human Colon Cancers, 1992.

John E. Taylor, Identification and Characterization Somatostatin (SRIF), Gastrin Releasing Peptide (GRP), and Neuromedin B (NMB) Receptors on Established Tumors and Tumor Cell Lines, 1993.

Benya, et al., Gastrin-releasing peptide receptor-induced internalization, down-regulation, desensitization, and growth: possible role for cyclic AMP, Mol Pharmacol. Aug. 1994;46(2):235-45.

Yano, et al., Inhibitory effect of bombesin/gastrin-releasing peptide antagonist RC-3095 and luteinizing hormone-releasing hormone antagonist SB-75 on the growth of MCF-7 MIII human breast cancer xenografts in athymic nude mice, Cancer. Feb. 15, 1994;73(4):1229-38.

Kull, Jr., et al., Conveyance of partial agonism/antagonism to bombesin/gastrin-releasing peptide analogues on Swiss 3T3 cells by a carboxyl-terminal leucine insertion, J Biol Chem. Oct. 15, 1992;267(29):21132-8.

Heinz-Erian, et al., [D-Phe12]bombesin analogues: a new class of bombesin receptor antagonists, Am J Physiol. Mar. 1987;252(3 Pt 1):G439-42.

Halmos, et al., Characterization of bombesin/gastrin-releasing peptide receptors in membranes of MKN45 human gastric cancer, Cancer Lett. Sep. 30, 1994;85(1):111-8.

Coy, et al., Short-chain pseudopeptide bombesin receptor antagonists with enhanced binding affinities for pancreatic acinar and Swiss 3T3 cells display strong antimitotic activity, J Biol Chem. Sep. 5, 1989;264(25):14691-7.

Woll, et al., [D-Argl,D-Phe5,D-Trp7,9,LeuII]substance P, a potent bombesin antagonist in murine Swiss 3T3 cells, inhibits the growth of human small cell lung cancer cells in vitro, Proc Natl Acad Sci U S A. Mar. 1988;85(6):1859-63.

Wang, et al., Des-Met carboxyl-terminally modified analogues of bombesin function as potent bombesin receptor antagonists, partial agonists, or agonists, J Biol Chem. Sep. 15, 1990;265(26):15695-703.

Von Schrenck, et al., "Potent Bombesin Receptor Antagonists distinguish Receptor Subtypes", Amer. J. Physiol., vol. 259, pp. G468-G473, 1990.

Singh, et al., A novel bombesin receptor antagonist (2258U89), potently inhibits bombesin evoked release of gastrointestinal hormones from rats and dogs, in vitro and in vivo, Regul Pept. Jul. 2, 1992;40(1):75-86.

Leban, et al., Development of Potent Bombesin/Gastrin-Releasing Peptide antagonists Having a D-Pro-(CH2NH)-Phe-NH2 C Terminus, Proc Natl Acad Sci U S A. Mar. 1, 1993;90(5):1922-6.

Mahmoud, et al., "[Psi 13, 14] Bombesin Analogues Inhibit Growth of Small Cell Lung Cancer in Vitro and in Vivo", Cancer Res. Apr. 1, 1991;51(7):1798-802.

Troutner, David E., Chemical and Physical Properties of Radionuclides, Nucl. Med. Biol. vol. 14, No. 3, pp. 171-176, 1987.

Vallabhajosula, et al., Preclinical evaluation of technetium-99m-labeled somatostatin receptor-binding peptides, J Nucl Med. Jun. 1996;37(6):1016-22.

Gali, et al., Synthesis, characterization, and labeling with 99mTc/188Re of peptide conjugates containing a dithia-bisphosphine chelating agent, Bioconjugate Chem. May-Jun. 2001;12(3):354-63.

Bijsterbosch, MK; Selective Drug Delivery by Means of Receptor-Mediated Endocytosis, The Quarterly Journal of Nuclear Medicine, vol. 39, No. 1, pp. 4-19, Mar. 1995.

Parker, David; Tumor Targeting with Radiolabelled Macrocycle-Antibody Conjugates, Chemical Society Reviews, vol. 19, No. 3, Sep. 1990, pp. 271-291.

Wilbur, D. Scott; Radiohalogenation of Proteins: An Overview of Radionuclides, Labeling Methods, and Reagents for Conjugate Labeling, Bioconjugate Chem. Nov.-Dec. 1992;3(6):433-70.

Smythe, et al.; The Mechanism of Receptor-Mediated Endocytosis; Eur. J. Biochem. 202, pp. 689-699, 1991.

Wong, et al.; Rhenium(V), and Technetium(V) Oxo Complexes of an N2N's Peptide Chelator: Evidence of Inter-conversion between the Syn and Anti Conformations; Inorg. Chem., 1997, 36, pp. 5799-5808.

Schumbiger, et al.; Vehicles, Chelators, and Radionuclides: Choosing the "Building Blocks" of an Effective Therapeutic Radioimmunoconjugate; Bioconjugate Chemistry, vol. 7, No. 2, pp. 165-179, Mar./Apr. 1996.

Mattes, M.J.; Pharmacokinetics of Antibodies and their Radiolabels. In: Cancer Therapy with Radiolabelled Antibodies (ed) D.M. Goldenberg, CRC Press, Boca Raton, Florida, Chapter 8, pp. 89-99, 1995.

Li, et al.; Comparisons of Rh(III) Chloride Complexation with [14]aneNS, [14]aneN2S2 and [14]aneN4 Macrocycles in Aqueous Solution, Radiochemica Acta 75, pp. 83-95 (1996).

Lister-James, et al.; Pharmacokinetic considerations in the development of peptide-based imaging agents, The Quarterly Journal of Nuclear Medicine, vol. 41, No. 2, pp. 111-118, 2000.

Lamberts, S.W.J., Reubi, J.C., Krenning, E.P.; Somatostatin and the Concept of Peptide Receptor Scintigraphy in Oncology, Seminars in Oncology, vol. 21, No. 5, Suppl. 13 (Oct. 1994), pp. 1-5.

Hermanson; Bioconjugate Techniques, Academic Press, Functional Targets, Chapter 1, pp. 3-136 (1996).

Hoffken, K.; Peptides in Oncology II, Somatostatin Analogues and Bombesin Antagonists (1993), Springer-Verlag, Berlin-Heidelberg, pp. 87-112.

Krenning, et al.; Essentials of Peptide Receptor Scintigraphy with Emphasis on the Somatostatin Analog Octreotide, Seminars in Oncology, vol. 21, No. 5, Suppl. 13 (Oct. 1994), pp. 6-14.

Eckelman, William C., Gibson, Raymond E., (1993) The Design of Site-Directed Radiopharmaceuticals for use in Drug Discovery, Nuclear Imaging in Drug Discovery, Development, and Approval (eds) H.D. Burns et al., Birkauser Publ. Inc., Boston, Ma.

Fischman, et al.; A ticket to ride: peptide radiopharmaceuticals, J Nucl Med. Dec. 1993;34(12):2253-63.

Duncan et al.; Indium-111-Diethylenetriaminepentaacetic Acid-Octreoide is Delivered in Vivo to Pancreatic, Tumor Cell, Renal, and Hepatocyte Lysosomes, Cancer Res. Feb. 15, 1997;57(4):659-71.

Eckelman, William c.; Radiolabeling with technetium-99m to study high-capacity and lo-capacity biochemical systems, Eur J Nucl Med. Mar. 1995;22(3):249-63.

Davis, et al.; Metabolic Stability and Tumor Inhibition of Bombesin/GRP Receptor Antagonists, Peptides. Mar.-Apr. 1992;13(2):401-7.

De Jong et al.; Yttrium-90 and indium-111 labeling, receptor binding and biodistribution of [DOTAO, d-Phe1,Tyr3]octreotide, a promising somatostatin analogue for radionuclide therapy, Eur J Nucl Med. Apr. 1997;24(4):368-71.

Fritzberg et al.; Targeted proteins for diagnostic imaging: does chemistry make a difference?; J Nucl Med. Mar. 1992;33(3):394-7.

Cai et al.; Pseudononapeptide Bombesin Antagonists Containing C-Terminal Trp or Tpi, Peptides, Mar.-Apr. 1992;13(2):267-71.

Coy et al.; Probing peptide backbone function in bombesin. A reduced peptide bond analogue with potent and specific receptor antagonist activity, J Biol Chem. Apr. 15, 1988;263(11):5056-60.

Donald J. Buchsbaum; Cancer Therapy with Radiolabelled Antibodies; Pharmacokinetics of Antibodies and their Radiolabels; Experimental Radioimmunotherapy and Methods to Increase Therapeutic Efficacy; CRC Press, Boca Raton, Chapter 10, pp. 115-140, 1995.

Zhu et al.; Binding, internalization, and processing of bombesin by rat pancreatic acini, Am J Physiol. Jul. 1991;261(1 Pt 1):G57-64.

Mulshine et al.; Autocrine growth factors as therapeutic targets in lung cancer, Chest. Jul. 1989;96(1 Suppl):31S-34S. Review.

Hoffken, K.; Peptides in Oncology II, Somatostatin Analogues: Mechanisms of Action, (1994), Springer-Verlag, Berlin-Heidelberg, pp. 1-136.

Gali, et al.; In Vitro and in Vivo Evaluation of 111In_Labeled DOTA_8_Aoc_BBN[7_14]NH2 Conjugate for Specific Targeting of Tumors Expressing Gastrin Releasing Peptide (GRP) Receptors, 47th Annual Meeting—Society of Nuclear Medicine, St. Louis, MO, J. Nucl. Med., 41(5), 119P, #471, 2000.

Gali, et al.; Influence of the Radiometal on the In Vivo Pharmacokinetic Properties of a Radiometal-labeled DOTA-Conjugated Peptide, 222nd American Chemical Society National Meeting, Chicago, Il, Aug. 2001 (Accepted).

Hoffman, et al.; Development and Characterization of a Receptor-Avid 111In-Labeled Peptide for Site Specific Targeting of Colon Cancer, 92nd Annual Meeting of the American Association for Cancer Research, New Orleans, LA, Proceedings of the American Association for Cancer Research, vol. 42, 139, #746, Mar. 2001.

Hoffman, et al.; Rh-105 Bombesin Analogs: Selective In Vivo Targeting of Prostate Cancer with a therapeutic Radionuclide, 45th Annual Meeting—Society of Nuclear Medicine, Jun. 1998;J.Nucl. Med., 39(5), #982, 222P.

Hoffman, et al.; Uptake in retention of a Rh-105 Labeled Bombesin Analogue in GRP Receptor Expressing Neoplasms: An In-Vitro Study, 44th Annual Meeting—Society of Nuclear Medicine, Jun. 1997;J.Nucl. Med., 38(5), #808, 188P, 1997.

Hoffman, et al.; Synthesis and Characterization of Rh-105 Labeled Bombesin Analogues: Enhancement of GRP Receptor Binding Affinity Utilizing Aliphatic Carbon Chain Linkers, 12th International Symposium on Radiopharmaceutical Chemistry, Jun. 1997.

Hoffman, et al.; Specific Uptake and retention of Rh-105 Labeled Bombesin Analogues in GRP-Receptor Expressing Cells, European Society of Nuclear Medicine, Aug. 1997; Eur. J. Nucl. Med., 24(8), 901, 1997.

Hoffman et al.; Radiometallated receptor-avid peptide conjugates for specific in vivo targeting of cancer cells, Nucl Med Biol. Jul. 2001;28(5):527-39.

Hoffman et al.; Targeting Small Cell Lung Cancer Using Iodinated Peptide Analogs, 11th International Symposium on Radiopharmaceutical Chemistry, Aug. 1995; J. Label. Comp'd Radiopharm., 37:321-323, 1995.

Hoffman et al.; Iodinated Bombesin Analogs: Effect of N-Terminal Chain Iodine Attachment on BBN/GRP Receptor Binding, 43rd Annual Meeting—Society of Nuclear Medicine, May 1996; J. Nucl. Med., 37(5), p. 185P, #850, 1996.

Hoffman et al.; Accumulation and Retention of 99mTc-RP591 by GRP Receptor Expressing Tumors in SCID Mice, Congress of the European Association of Nuclear Medicine, Barcelona, Spain, Eur. J. Nucl. Med., 26(9), 1157, #PS-416, Sep. 1999.

Hoffman et al.; Accumulation and Retention of 99mTc-RP527 by GRP Receptor Expressing Tumors in SCID Mice, 46th Annual Meting—Society of Nuclear Medicine, Jun. 9, 1999, Los Angeles, CA, J. Nucl. Med., 40(5), 104P, #419, 1999.

Hoffman et al.; 111In/90Y Radiolabelled Peptides for Targeting Prostate Cancer; A Matched Pair Gastrin Releasing Peptide (GRP) Receptor Localizing Radiopharmaceutical, 48th Annual Meting—Society of Nuclear Medicine, #1149, Toronto, Ontario, Canada, Jun. 2001. (Accepted).

Hoffman et al.; Vitro and in Vivo Evaluation of 111In/90Y Radiolabelled Peptides for Specific Targeting of Tumors Expressing Gastrin Releasing Peptide (GRP) Receptors, 92nd Annual Meting of the American Association for Cancer Research, New Orleans, LA. Proceedings of the American Association for Cancer Research, vol. 42, 773, #4148, Mar. 2001.

Hoffman et al.; Development of a Diagnostic Radiopharmaceutical for Visualization of Primary and Metastic Breast Cancer, 48th Annual Meting—Society of Nuclear Medicine, #1149, Toronto, Ontario, Canada, Jun. 2001, J. Nucl. Med., 45(5):245P, #1067.

Hoffman et al.; Targeting Gastrin Releasing Peptide (GRP-R) Expression in Prostate and Pancreatic Cancer Using Radiolabelled GRP Agonist Peptide Vectors, American Association for Cancer Research Annual Meeting, San Francisco, CA, Proceedings of the American Association for Cancer Research, vol. 41, 529, #3374, Apr. 2000.

Hoffman T.J., Smith, C.J., Simpson, S.D., Siekman, G., Higginbotham, C., Jiminez, H., Eshima, D., Thornback, J.R. and Volkert, W.A.; Optimizing Pharmacokinetics of Tc-99m-GRP Receptor Targeting Peptides Using Multi-Amino Acid Linking groups, 47th Annual Meting—Society of Nuclear Medicine, St. Louis, MO, J. Nucl. Med., 41(5), 228), #1013, 2000.

Jurrison, S., Cutler, C., Hu, F., Hoffman, T.J., Volkert, W.A.; DOTA Bombesin Complexes with Sm-153 and NCA PM-149, The International Chemical Congress of Pacific Basin Societies, Pacifichem 2000, Honolulu, HI, Dec. 2000.

Kara, S.R., Schibli, R., Gali, H., Katti, K.V., Hoffman, T.J., Higginbotham, C., Siekman, G., Volkert, W.A.; 99mTc-labeling and in vivo studies of a bombesin analogue with a novel water-soluble dithiadiphosphine-based bifunctional chelating agent, Bioconjug Chem. Mar.-Apr. 1999;10(2):254-60.

Katti, K.V., Gali, H., Schibli, R., Hoffman, T.J., and Volkert, W.A.; 99mTc/Re Coordination Chemistry and Biomolecule Conjugation Strategy of a Novel Water Soluble Phosphine-Based Bifunctional Chelating Agent, In Technetium, Rhenium and Other Metals in Chemistry and Nuclear Medicine (5), Ed by M. Nicolini and U. Mazzi, Servizi Grafici Editoriali, Padova, pp. 93-100, 1999.

Kothari, K.K. Katti, K.V., Prabhu, K.R., Gali, H., Pillarsetty, N.K., Hoffman, T.J., Owen, N.K., and Volkert, W.A.; Development of a Diamido-Diphosphine (N2P2)-BFCA for Labeling Cancer Seeking Peptides via the 99mTc(1)(CO)3(H2O)3 Intermediate, 47th Annual Meeting—Society of Nuclear Medicine, St. Louis, MO, J. Nucl. Med., 41(5), 244P, #1079, 2000.

Li, et al.; Development of an in vitro model for assessing the in vivo stability of lanthanide chelates, Nucl Med Biol. Feb. 2001;28(2):145-54.

Qin, et al.; Bombesin antagonists inhibit in vitro and in vivo growth of human gastric cancer and binding of bombesin to its receptors, J Cancer Res Clin Oncol., 1994; 120(9): 519-28.

Schibli, R., Karra, S.R., Gali, H., Katti, K.V., Higginbotham, C., Smith, C.J., Hoffman, T.J., and Volkert, W.A.; Conjugation of Small Biomolecules and Peptides with Water-Soluble Dithio-Bis-Hydroxymethylphosphine Ligands, Center Radiological Research, University of Missouri, Columbia, MO, USA. Book of Abstracts, 215th ACS National Meeting, Dallas, Mar. 29-Apr. 2, 1998, NUCL-062.

Schibli, R., Karra, S.R., Katti, K.V., Gali, H., Higginbotham, C., Siekman, G., Hoffman, T.J., and Volkert, W.A.; A Tc-99m-Dithia-Di(Bis-Hydroxy-methylene) Phosphine Conjugate of Bombesin: In Vitro and In Vivo Studies, 45th Annual Meeting—Society of Nuclear Medicine, May 1998; J. Nucl. Med., 39(5), 225P, #997.

Smith, C.J., Hoffman, T.J., Gali, H., Hayes, D.L., Owen, N.K., Siekman, G.L. and Volkert, W.A.; Radiochemical investigations of 177Lu-DOTA-8-Aoc-BBN[7-14]NH2: A New Gastrin Releasing Peptide Receptor (GRPr) Targeting Radiopharmaceutical, J. Labeled Compounds and Radiopharmaceutical, J. Labeled Cpd. Radipharm., 44 (51):5706-5708, 2001.

Volkert, W.A.; Rh-105 Bombesin Analogs: Selective In Vivo Targeting of Prostate Cancer with a Therapeutic Radionuclide, 45th Annual Meeting—Society of Nuclear Medicine, Jun. 1998; J. Nucl. Med., 39(5):222P, #59, 1998.

Volkert, W.A., and Hoffman, T.J., Design and Development of Receptor-avid Peptide Conjugates for In Vivo Targeting of Cancer, Part of the SPIE Conference of Molecular Imaging: Reporters-Dyes, Markers and Instrumentation, SPIE vol. 3600:86-98, Jan. 1999.

Volkert, W.A., Gali, H., Hoffman, T.J., Owen, N.K., Sieman, G.L., and Smith, C.J.; In-111/90Y Labeled GRP Analogs: A Structure-Activity Relationship, The International Chemical Congress of Pacific Basin Societies, Pacifichem 2000, Honolulu, HI, Dec. 2000.

Foster, B., and Volkert, W.A.; In-111/90Y Radiolabelled Peptides for targeting Prostate Cancer; A Matched Pair Gastrin releasing Peptide (GRP) Receptor Localizing Radiopharmaceutical, 48th Annual Meeting—Society of Nuclear Medicine, Toronto, Ontario, Canada, Jun. 2001. (Accepted).

"Modulation of Chromatographic Performances of HSA-Based HPLC Column By Reversible Binding of Lithocholic Acid" by C. Bertucci et al., Chromatographia 2801, 53, May, 515-518 (No. 9/10).

"Displacing Effects of Chenodeoxycholic Acid, Ursodeoxycholic Acid and Sulfadimethoxine on Plasma Protein Binding of Tolbutamide" by Shigeru Goto et al., J. Pharmacobio-Dyn., 8, 440-447 (1985).

* cited by examiner

Compound B

Compound D

Compound E

Compound F

L62

L67

L67

1. Morpholine (50% in DMA)
2. 3a, DIC, HOBT, DMA
3. Morpholine (50% in DMA)
4. DOTA tri-t-butyl ester, DIC, HOBT, DIEA, DMA
5. Reagent B

L63

L64

2b

L63

L64

L65

L66

L69

LINKERS FOR RADIOPHARMACEUTICAL COMPOUNDS

This application is the national stage filing of corresponding international application number PCT/US2003/041656, filed Dec. 24, 2003, which claims priority to and benefit of U.S. provisional application No. 60/439,722, filed Jan. 13, 2003, all of which are hereby incorporated by reference.

FIELD OF THE INVENTION

This invention relates to new and improved methods for improving the half life of pharmaceutical compounds which are useful as diagnostic or therapeutic agents by using novel linkers to attach a diagnostic or therapeutic moiety to a targeting moiety, or to attach two diagnostic or therapeutic moieties to each other, or to attach one diagnostic moiety to a therapeutic moiety.

BACKGROUND OF THE INVENTION

The use of pharmaceuticals (e.g., as diagnostic imaging agents, therapeutic agents, etc.) to detect and treat cancer is well known. In more recent years, the discovery of site-directed radiopharmaceuticals for cancer detection and/or treatment has gained popularity and continues to grow as the medical profession better appreciates the specificity, efficacy and utility of such compounds.

These newer radiopharmaceutical agents typically consist of a targeting agent connected to a metal chelator, which can be chelated to (e.g., complexed with) a diagnostic metal radionuclide such as, for example, technetium or indium, or a therapeutic metal radionuclide such as, for example, lutetium, yttrium, or rhenium. The role of the metal chelator is to hold (i.e., chelate) the metal radionuclide as the radiopharmaceutical agent is delivered to the desired site. A metal chelator which does not bind strongly to the metal radionuclide would render the radiopharmaceutical agent ineffective for its desired use since the metal radionuclide would therefore not reach its desired site. Thus, further research and development led to the discovery of metal chelators, such as that reported in U.S. Pat. No. 5,662,885 to Pollak et. al., hereby incorporated by reference, which exhibited strong binding affinity for metal radionuclides and the ability to conjugate with the targeting agent. Subsequently, the concept of using a "spacer" to create a physical separation between the metal chelator and the targeting agent was further introduced, for example in U.S. Pat. No. 5,976,495 to Pollak et. al., hereby incorporated by reference.

The role of the targeting agent, by virtue of its affinity for certain binding sites, is to direct the diagnostic or therapeutic agent, such as, for example, a radiopharmaceutical agent containing the metal radionuclide, to the desired site for detection or treatment. Typically, the targeting agent may include a protein, a peptide, or other macromolecule which exhibits a specific affinity for a given receptor. Other known targeting agents include monoclonal antibodies (MAbs), antibody fragments ($F_{ab}$ and $(F_{ab})_2$), and receptor-avid peptides. Donald J. Buchsbaum, "Cancer Therapy with Radiolabeled Antibodies; Pharmacokinetics of Antibodies and Their Radiolabels; Experimental Radioimmunotherapy and Methods to Increase Therapeutic Efficacy," CRC Press, Boca Raton, Chapter 10, pp. 115-140, (1995); Fischman, et al. "A Ticket to Ride: Peptide Radiopharmaceuticals," The Journal of Nuclear Medicine, vol. 34, No. 12, (December 1993):

In designing an effective compound for use as a diagnostic or therapeutic agent for cancer, it is important that the drug have appropriate in vivo targeting and pharmacokinetic properties. For example, it is preferable that for a radiopharmaceutical, the radiolabeled peptide has high specific uptake by the targeted cells. In addition, it is also preferred that once the radionuclide localizes at a targeted site, it remains there for a desired amount of time to deliver a highly localized radiation dose to the site.

Moreover, developing radiolabeled peptides that are cleared efficiently from normal tissues is also an important factor for radiopharmaceutical agents. When biomolecules (e.g., MAb, $F_{ab}$ or peptides) labeled with metallic radionuclides (via a chelate conjugation), are administered to an animal such as a human, a large percentage of the metallic radionuclide (in some chemical form) can become "trapped" in either the kidney or liver parenchyma (i.e., is not excreted into the urine or bile). Duncan et al.; Indium-111-Diethylenetriaminepentaacetic Acid-Octreotide Is Delivered in Vivo to Pancreatic, Tumor Cell, Renal, and Hepatocyte Lysosomes, Cancer Research 57, pp. 659-671, (Feb. 15, 1997). For the smaller radiolabeled biomolecules (i.e., peptides or $F_{ab}$), the major route of clearance of activity is through the kidneys which can also retain high levels of the radioactive metal (i.e., normally >10-15% of the injected dose). Retention of metal radionuclides in the kidney or liver is undesirable.

Conversely, clearance of a diagnostic or therapeutic agent from the blood stream too quickly by the kidney is also undesirable if longer diagnostic imaging or high tumor uptake for radiotherapy is needed. The retention of the radiopharmaceutical compound in the patient is often measured in terms of half life (i.e., the time it takes for one half of the administered dosage to be cleared from the patient). A radiopharmaceutical compound with a shorter half life indicates that it is cleared from the patient at a faster rate than a radiopharmaceutical compound with a longer half life.

A new and improved method for improving the half life of pharmaceutical compounds has now been found leading to improved diagnostic and therapeutic agents.

SUMMARY OF THE INVENTION

In an exemplary embodiment of the present invention, there is provided a new and improved method for improving the half life of a pharmaceutical compound for diagnostic or therapeutic use, as well as compounds which exhibit such an improved half life. In one embodiment, a diagnostic or therapeutic agent (such as, for example, a chemical moiety capable of complexing a medically useful metal ion or radionuclide (metal chelator) or an optical label) is attached to a targeting peptide by a linker or spacer group of the present invention. Alternatively, a radioactive halogen is attached to a targeting peptide by a linker or spacer group of the present invention.

As a result, compounds of the invention may generally have the formula:

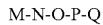

M-N-O-P-Q wherein M is the diagnostic or therapeutic agent, N-O-P is the linker, and Q is the targeting moiety. In one embodiment, M may be a metal chelator in the form complexed with a metal radionuclide or not. Alternatively, M may be a radioactive halogen instead of a metal chelator.

The metal chelator M may be any of the metal chelators known in the art for complexing with a medically useful metal ion or radionuclide. Preferred chelators include DTPA, DOTA, DO3A, HP-DO3A, EDTA, TETA, EHPG, HBED, NOTA, DOTMA, TETMA, PDTA, TTHA, LICAM, MECAM, or peptide chelators, such as, for example, those discussed herein. The metal chelator may or may not be complexed with a metal radionuclide, and may include an optional spacer such as a single amino acid. Preferred metal radionuclides for scintigraphy or radiotherapy include $^{99m}$Tc, $^{51}$Cr, $^{67}$Ga, $^{68}$Ga, $^{47}$Sc, $^{51}$Cr, $^{167}$Tm, $^{141}$Ce, $^{111}$In, $^{168}$Yb, $^{175}$Yb, $^{140}$La, $^{90}$Y, $^{88}$Y, $^{153}$Sm, $^{166}$Ho, $^{165}$Dy, $^{166}$Dy, $^{62}$Cu, $^{64}$Cu, $^{67}$Cu, $^{97}$Ru, $^{103}$Ru, $^{186}$Re, $^{188}$Re, $^{203}$Pb, $^{211}$Bi, $^{212}$Bi, $^{213}$Bi, $^{214}$Bi, $^{105}$Rh, $^{109}$Pd, $^{117m}$Sn, $^{149}$Pm, $^{161}$Tb, $^{177}$Lu, $^{198}$Au, and $^{199}$Au. The choice of metal will be determined based on the desired therapeutic or diagnostic application. For example, for diagnostic purposes the preferred radionuclides include $^{64}$Cu, $^{67}$Ga, $^{68}$Ga, $^{99m}$Tc, and $^{111}$In with $^{99m}$Tc, and $^{111}$In being particularly preferred. For therapeutic purposes, the preferred radionuclides include $^{64}$Cu, $^{90}$Y, $^{105}$Rh and $^{90}$Y, $^{111}$In, $^{117m}$Sn, $^{149}$Pm, $^{153}$Sm, $^{161}$Tb, $^{166}$Dy, $^{166}$Ho, $^{175}$Yb, $^{177}$Lu, $^{186/188}$Re and $^{199}$Au, with $^{177}$Lu, $^{90}$Y, $^{186}$Re and $^{188}$Re being particularly preferred. A most preferred chelator used in compounds of the invention is 1-substituted 4,7,10-tricarboxymethyl-1,4,7,10 tetraazacyclododecane triacetic acid (DO3A).

Where M is a radioactive halogen, preferred radionuclides such as $^{18}$F, $^{124}$I, $^{125}$I, $^{131}$I, $^{123}$I, $^{77}$Br, and $^{76}$Br may be used.

Where M is a diagnostic moiety, preferred diagnostic moieties include, for example, agents which enable detection of the compounds by such techniques as x-ray, magnetic resonance imaging, ultrasound, fluorescence and other optical imaging methodologies. A particularly preferred diagnostic moiety is a photolabel.

Where M is a therapeutic moiety, preferred compounds of the present invention can incorporate, for example, therapeutic moieties such as antibiotics, hormones, enzymes, antibodies, growth factors, etc.

The linker N-O-P contains at least one substituted bile acid.

The targeting peptide Q is any peptide, equivalent, derivative or analogue thereof which has binding affinity for a particular site. The targeting peptide may be a peptide that binds to a receptor or enzyme of interest. For example, the targeting peptide Q may be LHRH, insulin, oxytosin, somatostatin, NK-1, VIP, GRP, bombesin or any other hormone peptides known in the art, as well as analogues and derivatives thereof.

In an alternative embodiment, a diagnostic or therapeutic agent is attached to a diagnostic or therapeutic agent by a linker or specer group of the present invention. Compounds of this embodiment may generally have the formula:

wherein M is a diagnostic or therapeutic agent, as defined above, and N-O-P is the linker as defined above.

There is also provided a novel method of imaging using the compounds of the present invention.

There is further provided a novel method for preparing a diagnostic imaging agent comprising the step of adding to an injectable imaging medium a substance containing the compounds of the present invention.

A single or multi-vial kit that contains all of the componenets needed to prepare the diagnostic or therapeutic agents of the invention is an integral part of the present invention.

Novel methods of therapy (including radiotherapy and phototherapy) using the compounds of the invention is also provided, as is a novel method for preparing a radiotherapeutic agent comprising the step of adding to an injectable therapeutic medium a substance comprising a compound of the invention.

Figure 8A:
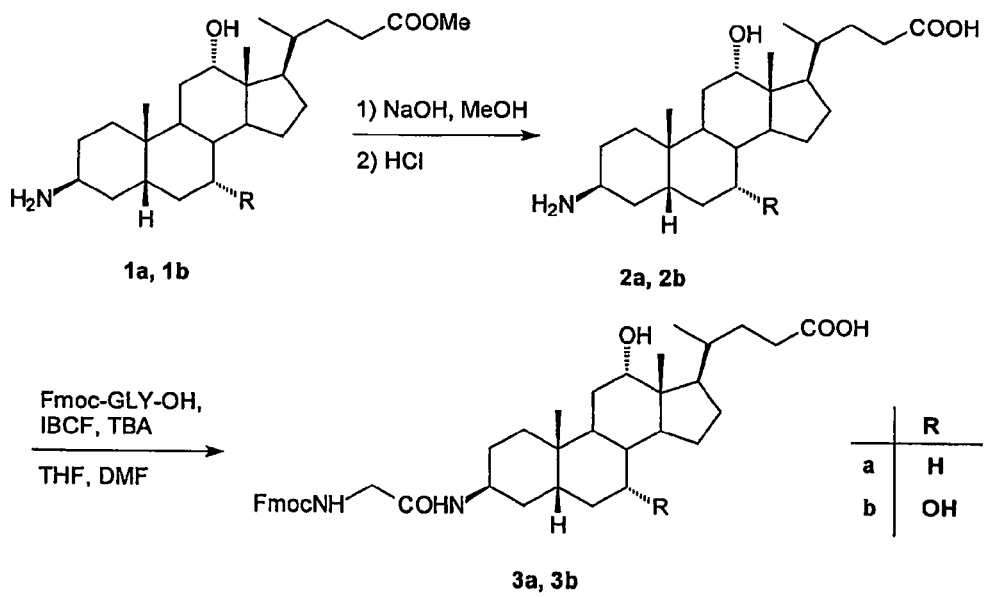
FIG. 8A is a graphical representation of a sequence of reactions to obtain intermediates (3β,5β, 12α)-3-[[(9H-Fluoren-9-ylmethoxy)amino]acetyl]amino-12-hydroxy cholan-24-oic acid (3a) and (3β,5β,7α,12α)-3-[[(9H-Fluoren-9ylmethoxy)amino]acetyl]amino-7,12-dihydroxycholan-2⁴-oic acid (3b), as described in Example X.
Figure 8B:
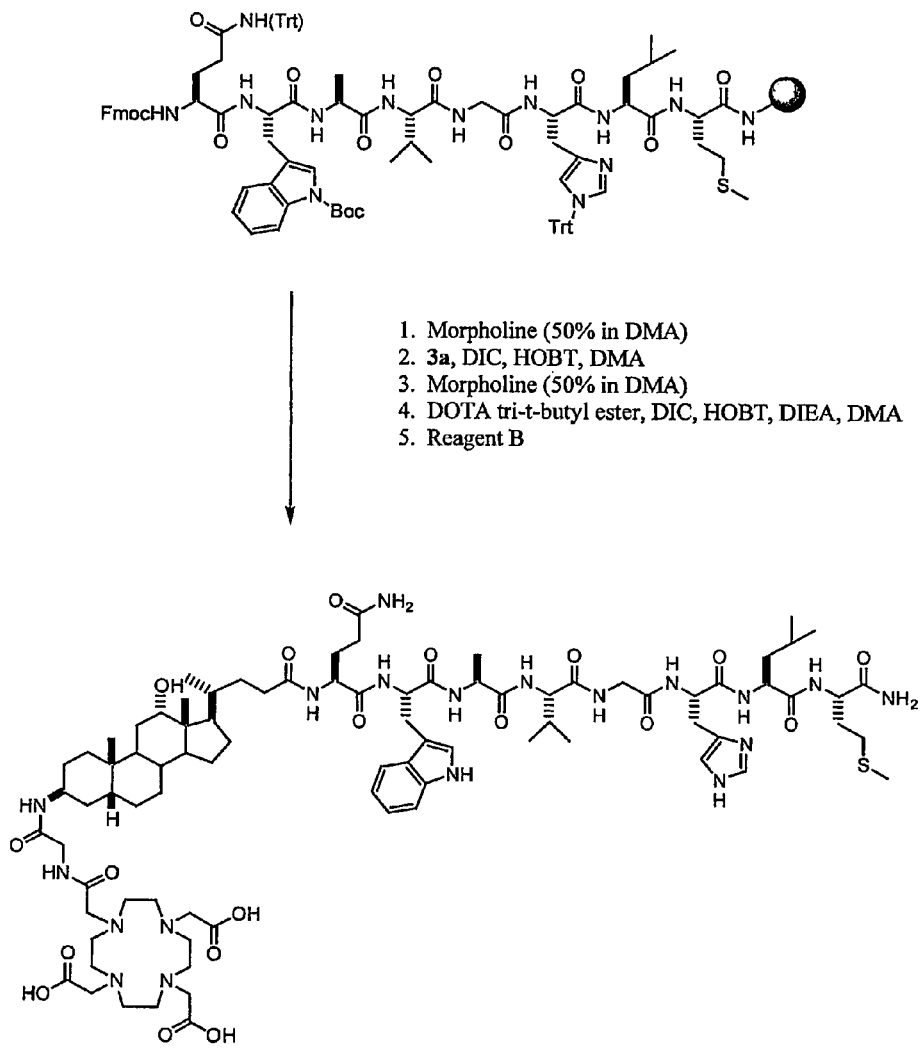
FIG. 8B is a graphical representation of the sequential reaction for the synthesis of N-[(3β,5β,12α)-3-[[[[4,7,10-Tris(carboxymethyl)-1,4,7,10-tetraazacyclododec-1-yl]acetyl]amino]acetyl]amino]-12-hydroxy-24-oxocholan-24-yl]-L-glutaminyl-L-tryptophyl-L-alanyl-L-valyl-glycyl-L-histidyl-L-leucyl-L-methioninamide (L63); N-[(3β,5β,7α, 12α)-3-[[[[4,7,10-Tris(carboxymethyl)-1,4,7,10-tetraazacyclo dodec-1-yl]acetyl]amino]acetyl]amino]-7,12-dihydroxy-24-oxocholan-24-yl]-L-glutaminyl-L-tryptophyl-L-alanyl-L-valyl-glycyl-L-histidyl-L-leucyl-L-methioninamide (L64); and N-[(3β,5β)-3-[[[[4,7,10-Tris(carboxymethyl)-1,4,7,10-tetraazacyclododec-1-yl]acetyl amino] acetyl]amino]-12,24-dioxocholan-24-yl]-L-glutaminyl-L-tryptophyl-L-alanyl-L-valyl-glycyl-L-histidyl-L-leucyl-L-methioninamide (L67) as described in Example X.
Figure 8C:
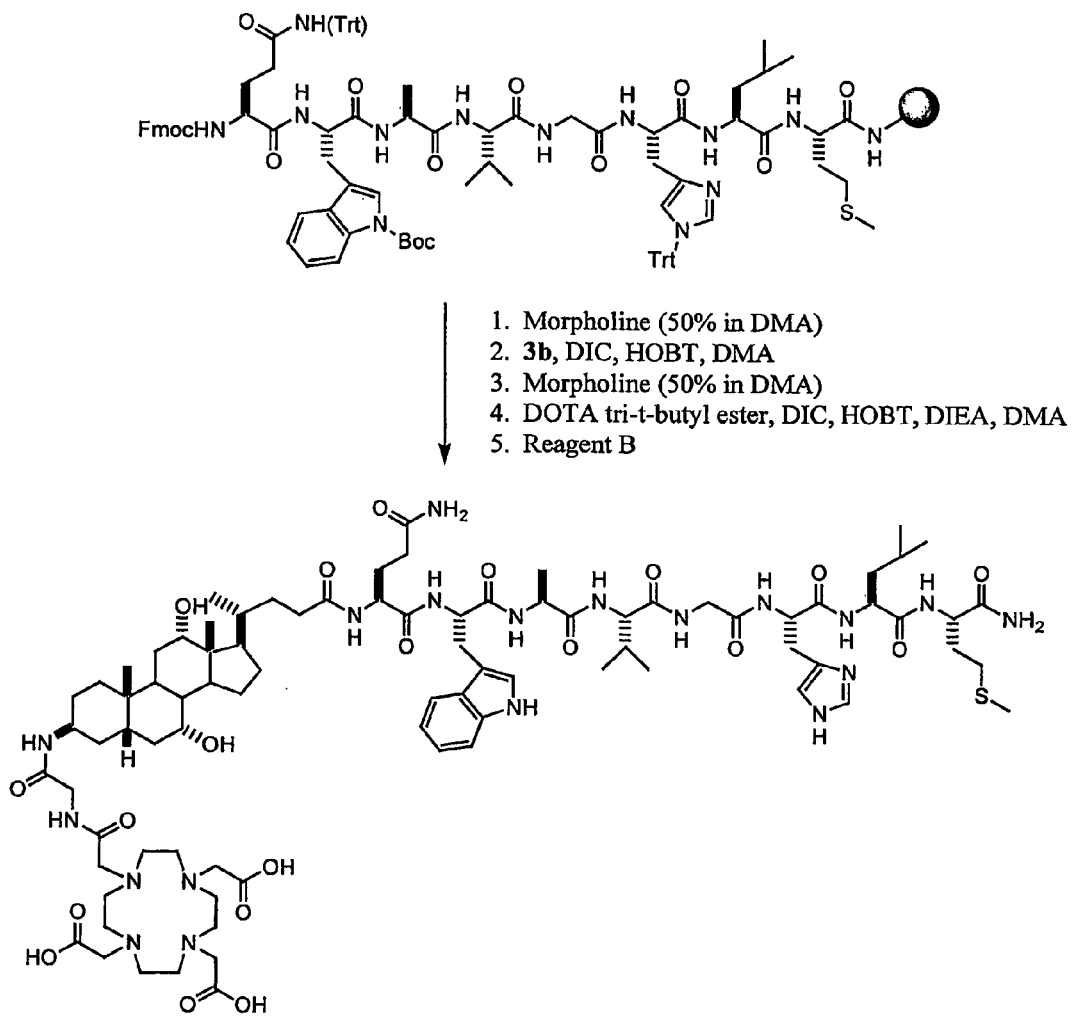
FIG. 8C is a graphical representation of the sequential reaction for the synthesis of N-[(3β,5β,7α,12α)-3-[[[[4,7, 10-Tris(carboxymethyl)-1,4,7,10-tetraazacyclododec-1-yl]
Figure 8D:
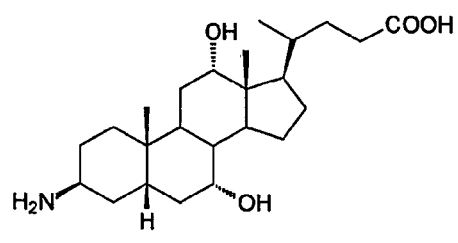
Figure 8E:
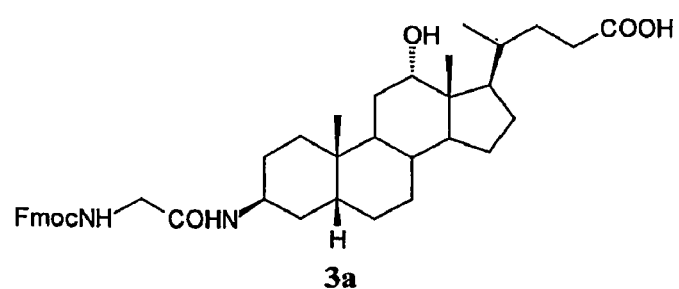
Figure 8F:
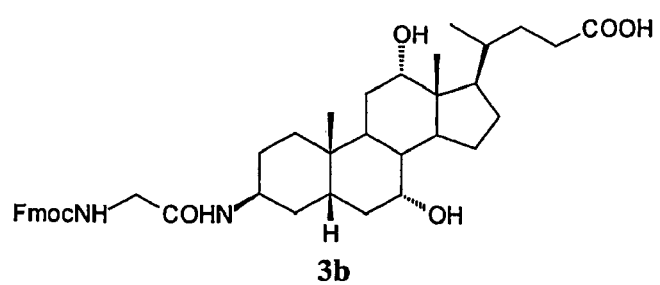
Figure 8G:
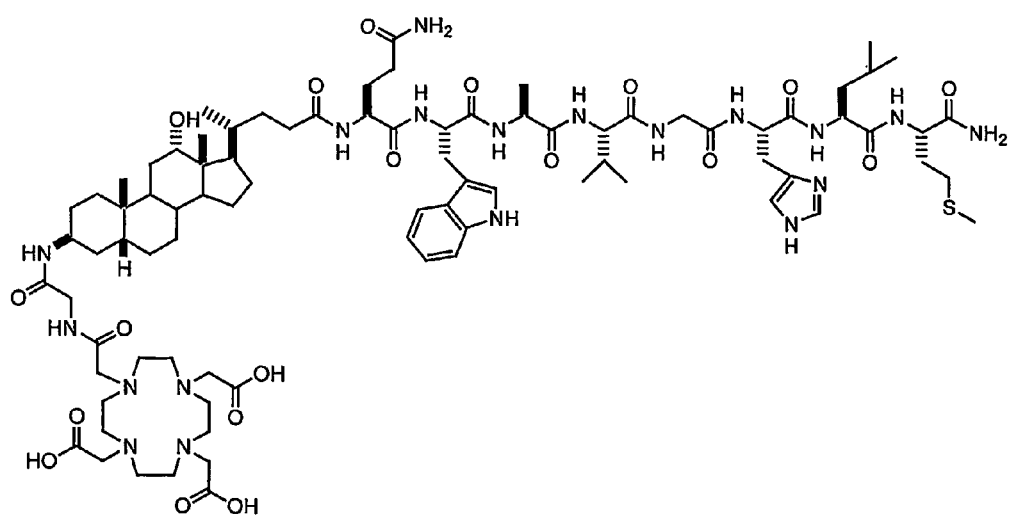
Figure 8H:
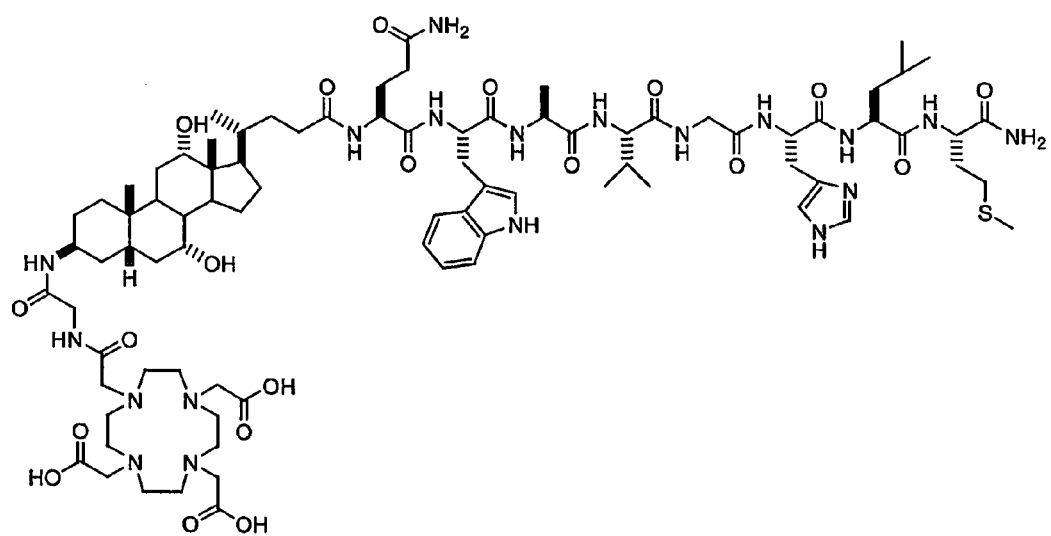
Figure 9:
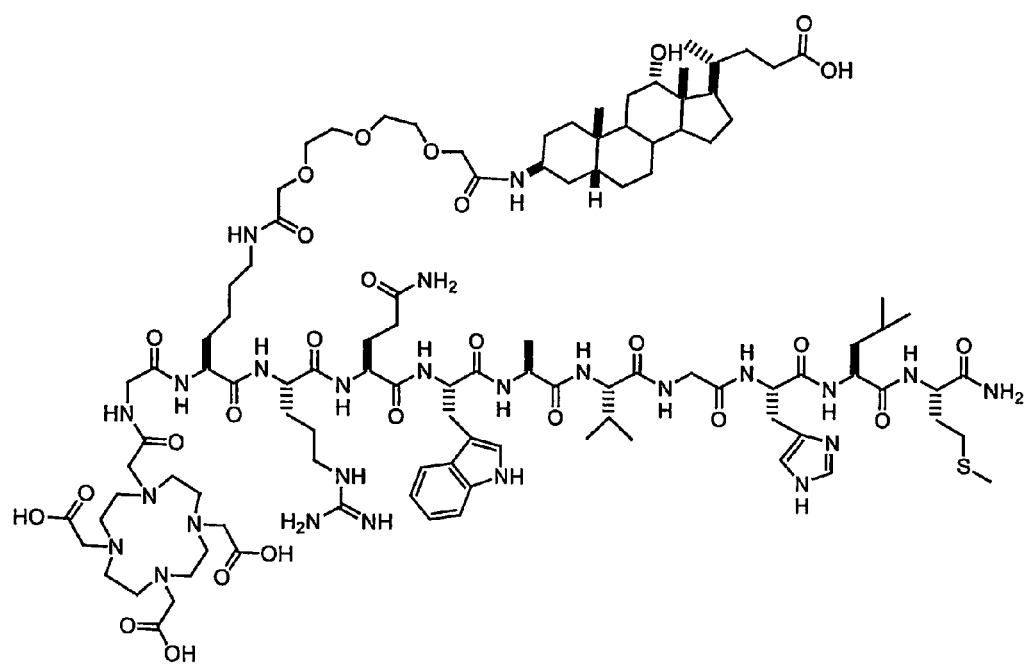
Figure 10A:
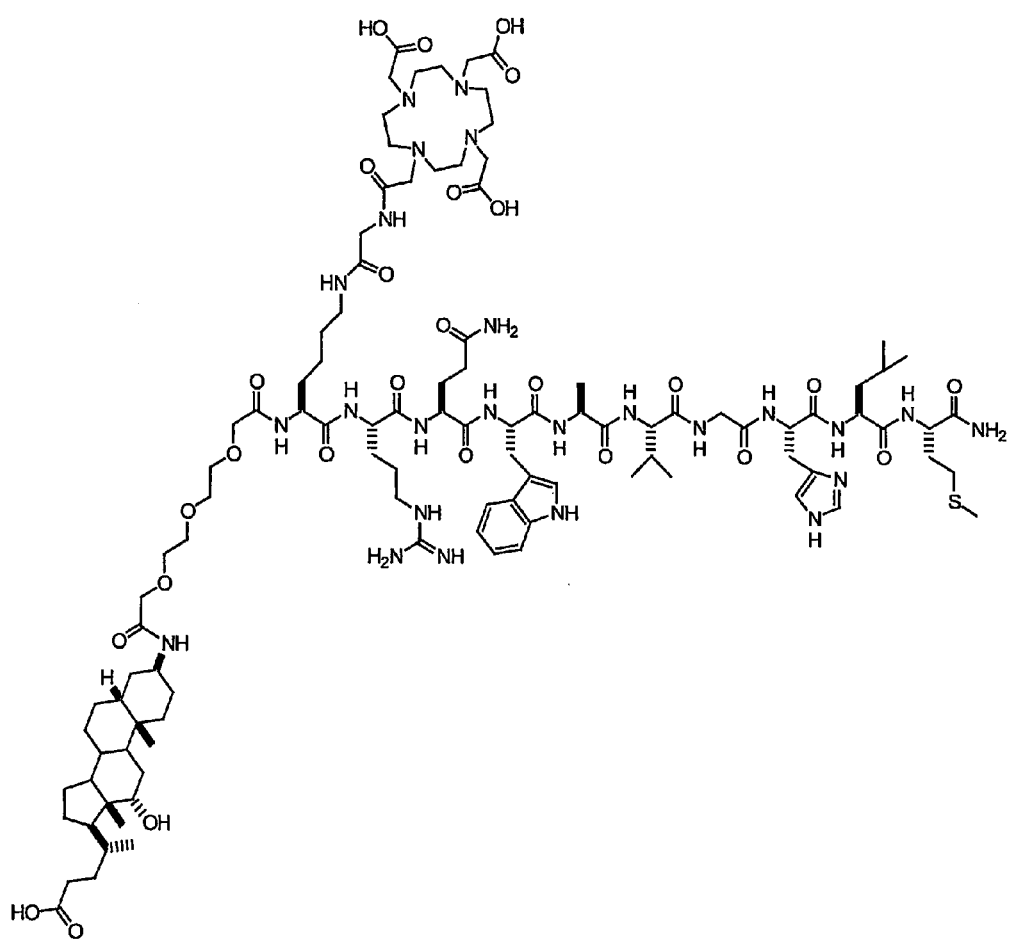
Figure 10B:
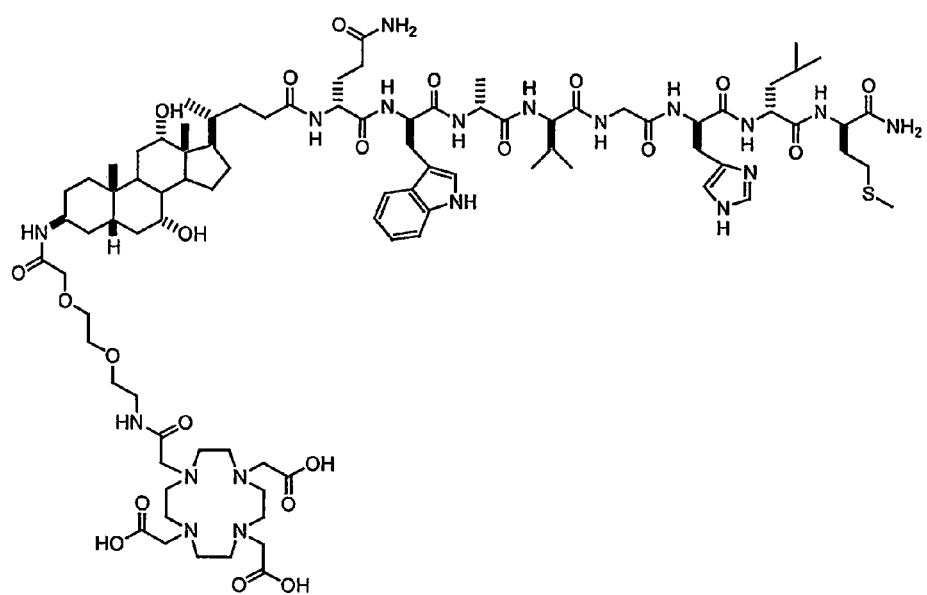
Figure 11A:
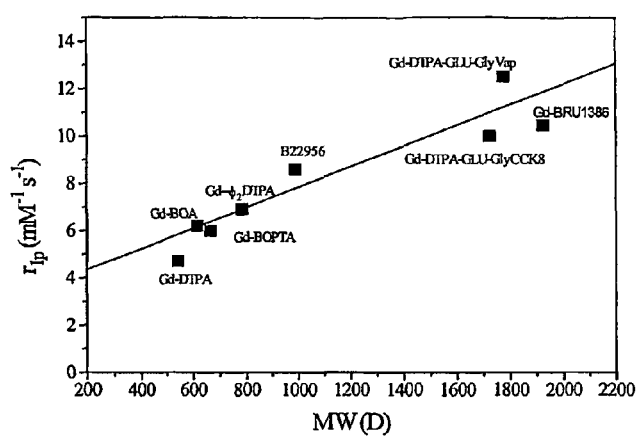
Figure 11B:
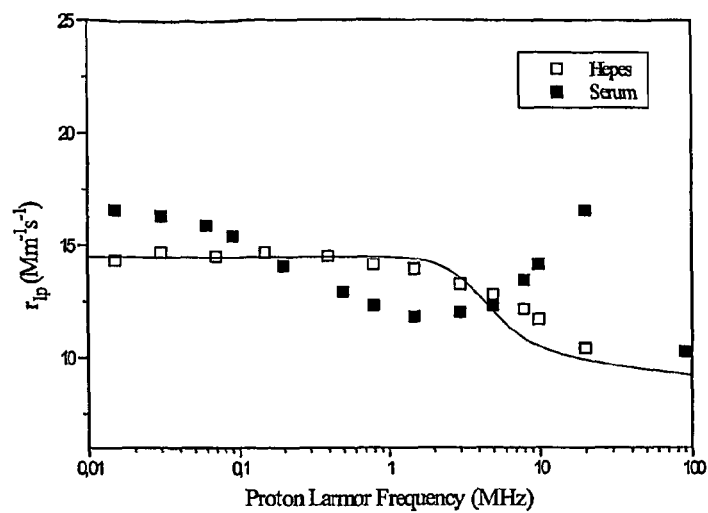
Figure 12A:
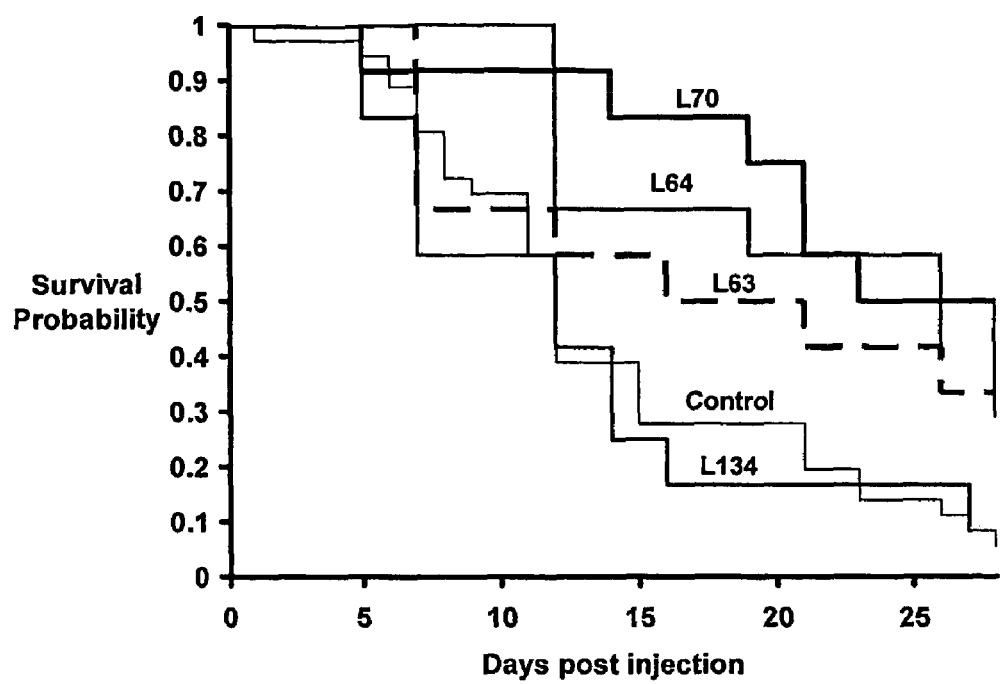
Figure 12B:
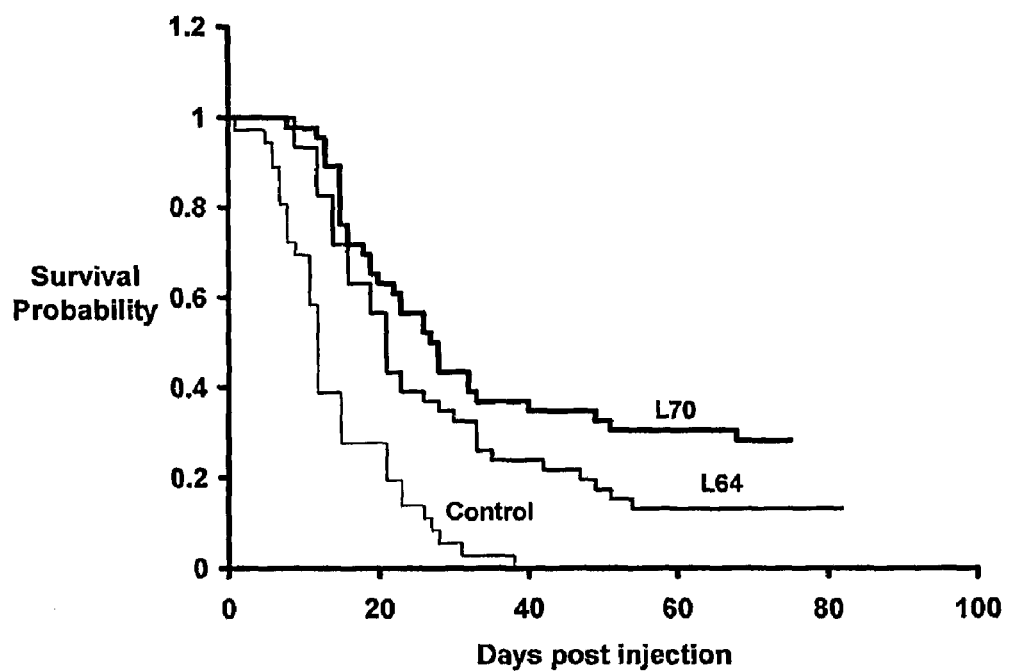

acetyl]amino]acetyl]amino]-7,12-dihydroxy-24-oxocholan-24-yl]-L-glutaminyl-L-tryptophyl-L-alanyl-L-valyl-glycyl-L-histidyl-L-leucyl-L-methioninamide (L64), as described in Example X;

FIG. 8D is a chemical structure of (3β,5β,7α,12α)-3-amino-7,12-dihydroxycholan-24-oic acid (2b), as described in Example X;

FIG. 8E is a chemical structure of (3β,5β,12α)-3-[[(9H-Fluoren-9-ylmethoxy)amino]acetyl]amino]-12-hydroxycholan-24-oic acid (3a), as described in Example X;

FIG. 8F is a chemical structure of (3β,5β,7α,12α)-3-[[(9H-Fluoren-9-ylmethoxy)amino]acetyl]amino-7,12-dihydroxycholan-24-oic acid (3b), as described in Example X;

FIG. 8G is a chemical structure of N-[(3β,5β,12α)-3-[[[[[4,7,10-Tris(carboxymethyl)-1,4,7,10-tetraazacyclododec-1-yl]acetyl]amino]acetyl]amino]-12-hydroxy-24-oxocholan-24-yl]-L-glutaminyl-L-tryptophyl-L-alanyl-L-valyl-glycyl-L-histidyl-L-leucyl-L-methioninamide (L63), as described in Example X;

FIG. 8H is a chemical structure of N-[(3β,5β,7α,12α)-3-[[[[[4,7,10-Tris(carboxymethyl)-1,4,7,10-tetraazacyclododec-1-yl]acetyl]amino]acetyl]amino]-7,12dihydroxy-24-oxocholan-24-yl]-L-glutaminyl-L-tryptophyl-L-alanyl-L-valyl-glycyl-L-histidyl-L-leucyl-L-methioninamide (L64), as described in Example X;

FIG. 9 is a chemical structure of DO3A-monoamide-Gly-Lys-(3,6,9-trioxaundecane-1,11-dicarboxylic acid-3,7-dideoxy-3-aminocholic acid)-L-arginyl-L-glutaminyl-L-triptophyl-L-alanyl-L-valyl-glycyl-L-histidyl-L-leucyl-L-methioninamide (L65);

FIG. 10A is a chemical structure of N-[2-S-[[[[[12α-Hydroxy-17β-(1-methyl-3-carboxypropyl)etiocholan-3 B-carbamoylmnethoxyethoxyethoxyacetyl]-amino-6-[4,7,10-tris(carboxymethyl)-1,4,7,10-tetraazacyclododec-1-yl]acetyl]amino]acetyl]amino]hexanoyl-L-glutaminyl-L-trtophyl-L-alanyl-L-valyl-glycyl-L-histidyl-L-leucyl-L-methioninamide (L66);

FIG. 10B is a chemical structure N-[(3β,5β,7α,12α)-3-[[[[[[4,7,10-Tris(carboxymethyl)-1,4,7,10-tetraazacyclododec-1-yl]acetyl]amino]ethoxyethoxy]acetyl]amino]-7,12-dihydroxycholan-24-yl]-L-glutaminyl-L-tryptophyl-L-alanyl-L-valyl-glycyl-L-histidyl-L-leucyl-L-methioninamide (L69);

FIG. 11A is a graphical representation of the results of HSA binding experiments with Gd-L64 described in Example XV;

FIG. 11B is a graphical representation of the results of HSA binding experiments with Gd-L64 described in Example XV;

FIG. 12A is a graphical representation of the results of radiotherapy experiments described in Example XVII; and FIG. 12B is a graphical representation of the results of other radiotherapy experiments described in Example XVII.

Figure 13A:
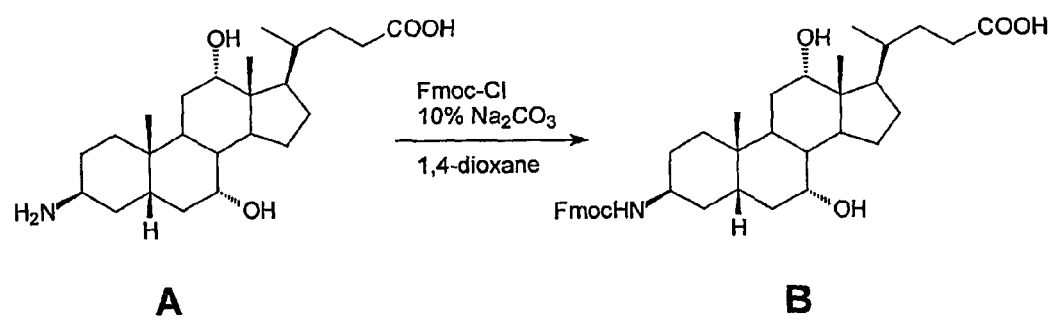

FIG. 13A is a graphical representation of a reaction for the synthesis of (3β,5β,7α,12α)-3-(9H-Fluoren-9-ylmethoxy)amino-7,12-dihydroxycholan-24-oic acid (B) as described in Example XX.

Figure 13B:
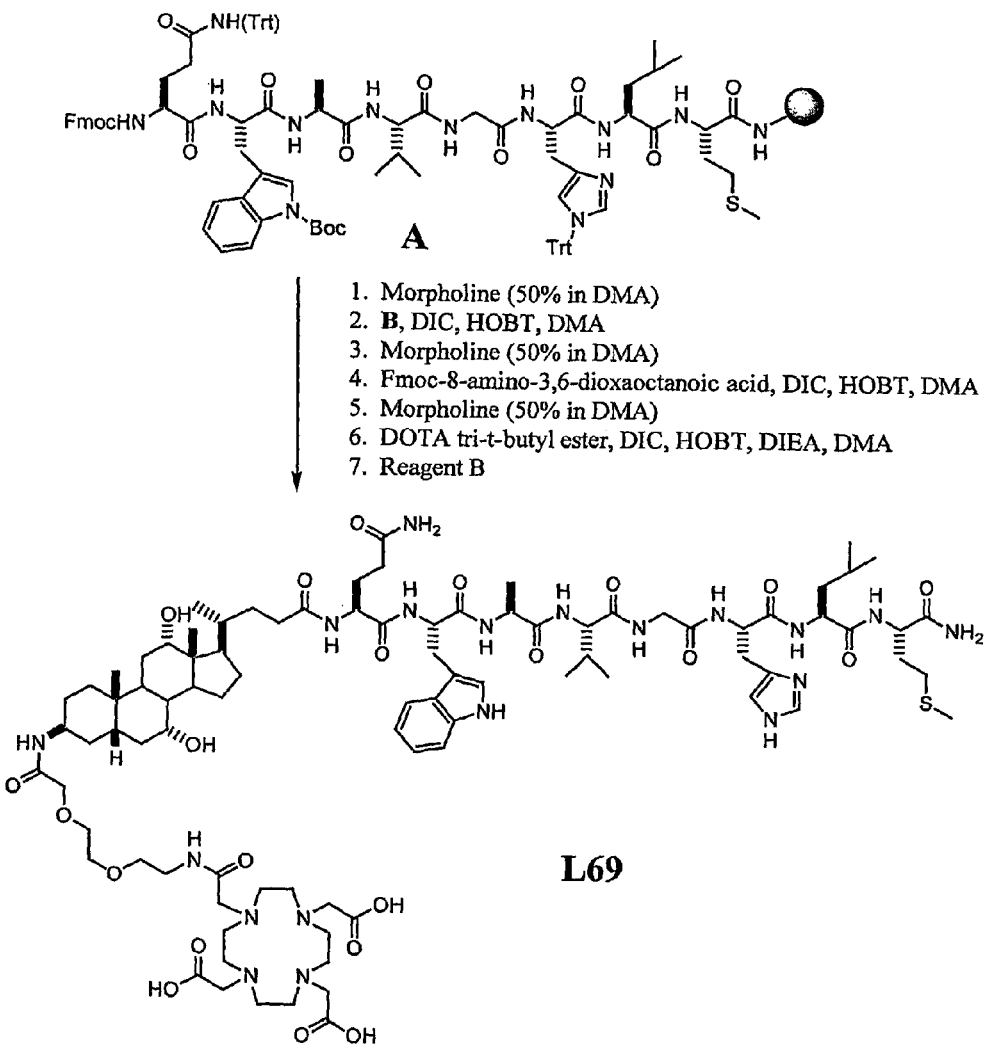

FIG. 13B is a graphical representation of a reaction for the synthesis of N-[(3β,5β,7α,12α)-3-[[[2-[2-[[[4,7,10-Tris(carboxymethyl)-1,4,7,10-tetraazacyclododec-1-yl]acetyl]amino]ethoxy]ethoxy]acetyl]amino]-7,12-dihydroxy-24-oxocholan-24-yl]-L-glutaminyl-L-tryptophyl-L-alanyl-L-valyl-glycyl-L-histidyl-L-leucyl-L-methioninamide, (L69), as described in Example XX.

DETAILED DESCRIPTION OF THE INVENTION

In the following description, various aspects of the present invention will be further elaborated. For purposes of explanation, specific configurations and details are set forth in order to provide a thorough understanding of the present invention. However, it will also be apparent to one skilled in the art that the present invention may be practiced without the specific details. Furthermore, well known features may be omitted or simplified in order not to obscure the present invention.

In an embodiment of the present invention, there is provided a new and improved method for improving the half life of a pharmaceutical compound for use in diagnosis or therapy, as well as compounds exhibiting such improved half life. In these embodiments, a diagnostic or therapeutic agent (such as a metal chelator, a radioactive halogen, or an optical label) is attached to a targeting peptide by a linker or spacer group of the present invention.

In general, compounds of the invention comprise compounds of the formula:

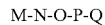

wherein M is the diagnostic or therapeutic agent, N-O-P is the linker, and Q is the targeting moiety. As explained in more detail infra, M and Q may be attached at either end of the linker (e.g. at an amino or a carboxylic acid group of a cholic acid derivative of the invention) or M and Q may both be attached to the same end of the linker (e.g. both to an amino or both to a carboxylic acid group of a cholic acid derivative linker of the invention).

In an alternative embodiment, a diagnostic or therapeutic agent is attached to a second diagnostic or therapeutic agent by a linker or spacer group of the present invention. Compounds of this embodiment may generally have the formula:

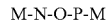

wherein M is a diagnostic or therapeutic agent, as defined above, and N-O-P is the linker as defined above. As explained in more detail infra, each M may be attached at either end of the linker (e.g. at an amino or a carboxtlic acid group of a cholic acid derivative linker of the invention) or both M may be attached to the same end of the linker (e.g. both attached to an amino or carboxylic acid groups of a cholic acid derivative linker of the invention).

Each of the diagnostic or therapeutic agent, linker, and targeting moiety is described in the discussion that follows. When M is a metal chelator, it may be in the form complexed with a metal radionuclide or not. Alternatively, M may be a radioactive halogen instead of a metal chelator. In another preferred embodiment, M is an optical label (e.g. a photolabel or other label detectable by light imaging, optoacoustical imaging or photoluminescence or useful in phototherapy).

In another embodiment of the present invention, there is provided a new and improved linker or spacer group which is capable of improving the half life of a pharmaceutical compound when used to link a diagnostic or therapeutic agent to a targeting moiety or to link a diagnostic or therapeutic agent to a second diagnostic or therapeutic agent. In general, linkers of the present invention may have the formula:

wherein each of N, O and P are defined throughout the specification.

Compounds meeting these criteria have improved pharmacokinetic properties compared to other radiolabeled targeting peptide conjugates known in the art. For example, compounds prepared with the linkers of the present invention appear to be retained in the bloodstream longer (consistent with binding to human serum albumin (HSA)), and thus will have a longer half life than prior known compounds. The longer half life is medically beneficial because it permits longer diagnostic imaging time, or for therapeutic uses, longer exposure to of the targeted cells and tumors to radioactive treatment.

1A. Metal Chelator

The term "metal chelator" refers to a molecule that forms a complex with a metal atom, wherein said complex is stable under physiological conditions. That is, the metal will remain complexed to the chelator backbone in vivo. More particularly, a metal chelator is a molecule that complexes to a radionuclide metal to form a metal complex that is stable under physiological conditions and which also has at least one reactive functional group for conjugation with the linker N-O-P. The metal chelator M may be any of the metal chelators known in the art for complexing a medically useful metal ion or radionuclide. The metal chelator may or may not be complexed with a metal radionuclide. Furthermore, the metal chelator can include an optional spacer such as, for example, a single amino acid (e.g., Gly) which does not complex with the metal, but which creates a physical separation between the metal chelator and the linker.

The metal chelators of the invention may include, for example, linear, macrocyclic, terpyridine, and $N_3S$, $N_2S_2$, or $N_4$ chelators (see also, U.S. Pat. Nos. 5,367,080, 5,364,613, 5,021,556, 5,075,099, 5,886,142, the disclosures of which are incorporated by reference herein in their entirety), and other chelators known in the art including, but not limited to, HYNIC, DTPA, EDTA, DOTA, TETA, and bisamino bisthiol (BAT) chelators (see also U.S. Pat. No. 5,720,934). For example, $N_4$ chelators are described in U.S. Pat. Nos. 6,143,274; 6,093,382; 5,608,110; 5,665,329; 5,656,254; and 5,688,487, the disclosures of which are incorporated by reference herein in their entirety. Certain $N_3S$ chelators are described in PCT/CA94/00395, PCT/CA94/00479, PCT/CA95/00249 and in U.S. Pat. Nos. 5,662,885; 5,976,495; and 5,780,006, the disclosures of which are incorporated by reference herein in their entirety. The chelator may also include derivatives of the chelating ligand mercapto-acetyl-glycyl-glycyl-glycine (MAG3), which contains an $N_3S$, and $N_2S_2$ systems such as MAMA (monoamidemonoaminedithiols), DADS ($N_2S$ diaminedithiols), CODADS and the like. These ligand systems and a variety of others are described in Liu and Edwards, Chem Rev. 1999, 99, 2235-2268 and references therein, the disclosures of which are incorporated by reference herein in their entirety.

The metal chelator may also include complexes containing ligand atoms that are not donated to the metal in a tetradentate array. These include the boronic acid adducts of technetium and rhenium dioximes, such as those described in U.S. Pat. Nos. 5,183,653; 5,387,409; and 5,118,797, the disclosures of which are incorporated by reference herein, in their entirety.

Examples of preferred chelators include, but are not limited to, diethylenetriamine pentaacetic acid (DTPA), 1,4,7,10-tetraazacyclotetradecane-1,4,7,10-tetraacetic acid (DOTA), 1-substituted 1,4,7,-tricarboxymethyl 1,4,7,10 tetraazacyclododecane triacetic acid (DO3A), ethylenediaminetetraacetic acid (EDTA), and 1,4,8,11-tetraazacyclotetradecane-1,4,8,11-tetraacetic acid (TETA). Additional chelating ligands are ethylenebis-(2-hydroxy-phenylglycine) (EHPG), and derivatives thereof, including 5-Cl-EHPG, 5-Br-EBPG, 5-Me-EHPG, 5-t-Bu-EHPG, and 5-sec-Bu-EHPG; benzodiethylenetriamine pentaacetic acid (benzo-DTPA) and derivatives thereof, including dibenzo-DTPA, phenyl-DTPA, diphenyl-DTPA, benzyl-DTPA, and dibenzyl-DTPA; bis-2 (hydroxybenzyl)-ethylene-diaminediacetic acid (HBED) and derivatives thereof; the class of macrocyclic compounds which contain at least 3 carbon atoms, more preferably at least 6, and at least two heteroatoms (O and/or N), which macrocyclic compounds can consist of one ring, or two or three rings joined together at the hetero ring elements, e.g., benzo-DOTA, dibenzo-DOTA, and benzo-NOTA, where NOTA is 1,4,7-triazacyclononane N,N',N''-triacetic acid, benzo-TETA, benzo-DOTMA, where DOTMA is 1,4,7,10-tetraazacyclotetradecane-1,4,7,10-tetra(methyl tetraacetic acid), and benzo-TETMA, where TETMA is 1,4,8,11-tetraazacyclotetradecane-1,4,8,11-(methyl tetraacetic acid); derivatives of 1,3-propylenediaminetetraacetic acid (PDTA) and triethylenetetraaminehexaacetic acid (TTHA); derivatives of 1,5,10-N,N',N''-tris(2,3-dihydroxybenzoyl)-tricatecholate (LICAM) and 1,3,5-N,N',N''-tris(2,3-dihydroxybenzoyl) aminomethylbenzene (MECAM). Examples of representative chelators and chelating groups contemplated by the present invention are described in WO 98/18496, WO 86/06605, WO 91/03200, WO 95/28179, WO 96/23526, WO 97/36619, PCT/US98/01473, PCT/US98/20182, and U.S. Pat. Nos. 4,899,755, 5,474,756, U.S 5,846,519, 6,143,274, co-pending application U.S. Provisional Ser. No. 60/532,842, each of which is hereby incorporated by reference in its entirety.

Particularly preferred metal chelators include those of Formula 1, 2 and 3 (for $^{111}$In and radioactive lanthanides, such as, for example $^{177}$Lu, $^{90}$Y, [153]Sm, and [166]Ho) and those of Formula 4, 5 and 6 (for radioactive $^{99m}$Tc, [186]Re, and [188]Re) set forth below. These and other metal chelating groups are described in U.S. Pat. Nos. 6,093,382 and 5,608,110, which are incorporated by reference herein in their entirety. Additionally, the chelating group of Formula 3 is described in, for example, U.S. Pat. No. 6,143,274; the chelating group of Formula 5 is described in, for example, U.S. Pat. Nos. 5,627,286 and 6,093,382, and the chelating group of Formula 6 is described in, for example, U.S. Pat. Nos. 5,662,885; 5,780,006; and 5,976,495. Specific metal chelators of Formula 6 include N,N-dimethyl-Gly-Ser-Cys; N,N-dimethyl-Gly-Thr-Cys; N,N-diethyl-Gly-Ser-Cys; N,N-dibenzyl-Gly-Ser-Cys; and other variations thereof. For example, spacers which do not actually complex with the metal radionuclide such as an extra single amino acid Gly, may be attached to these metal chelators (e.g., N,N-dimethyl-Gly-Ser-Cys-Gly; N,N-dimethyl-Gly-Thr-Cys-Gly; N,N-diethyl-Gly-Ser-Cys-Gly; N,N-dibenzyl-Gly-Ser-Cys-Gly). Other useful metal chelators such as all of those disclosed in U.S. Pat. No. 6,334,996, also incorporated by reference (e.g., Dimethyl-Gly-L-t-Butyl-Gly-L-Cys-Gly; Dimethyl-Gly-D-t-Butyl-Gly-L-Cys-Gly; Dimethyl-Gly-L-t-Butyl-Gly-L-Cys, etc.)

Furthermore, sulfur protecting groups such as Acm (acetamidomethyl), trityl or other known alkyl, aryl, acyl, alkanoyl, aryloyl, mercaptoacyl and organothiol groups may be attached to the cysteine amino acid of these metal chelators.

Additionally, other useful metal chelators include:

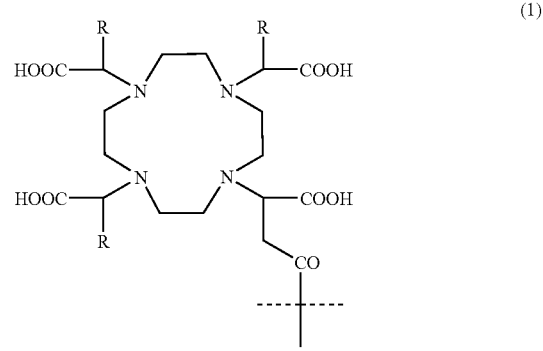

(2)
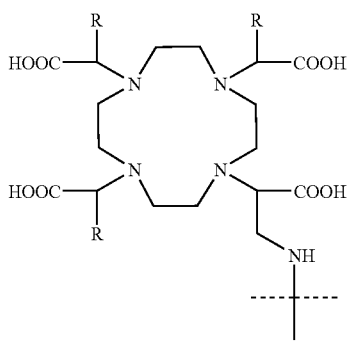

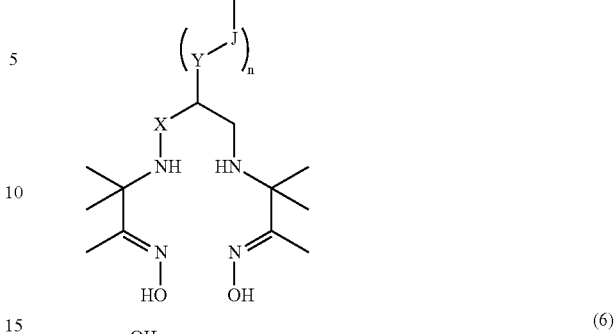
(5b)

(3)
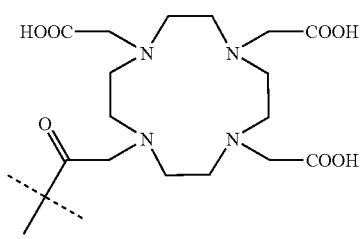

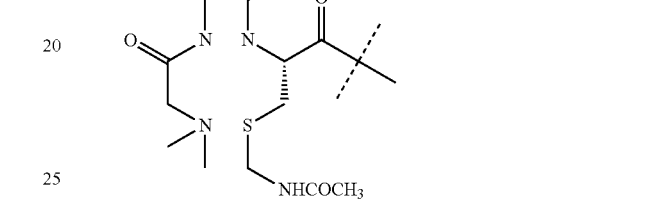
(6)

(4a)
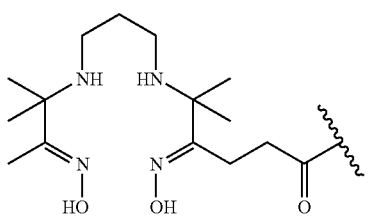

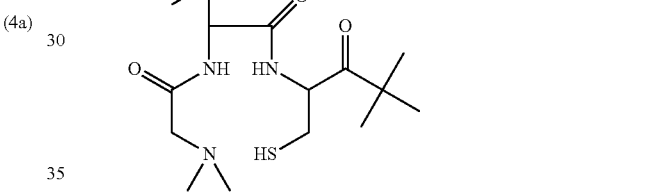
(7)

(4b)
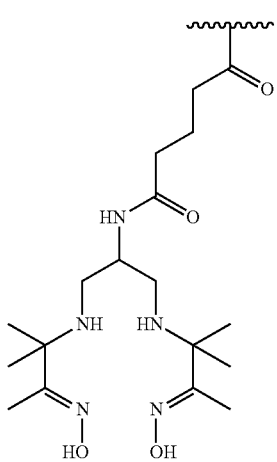

In the above Formulas 1 and 2, R is alkyl, preferably methyl. In the above Formulas 5a and 5b, X is either $CH_2$ or O; Y is $C_1$-$C_{10}$ branched or unbranched alkyl; aryl, aryloxy, arylamino, arylaminoacyl; arylalkyl—where the alkyl group or groups attached to the aryl group are $C_1$-$C_{10}$ branched or unbranched alkyl groups, $C_1$-$C_{10}$ branched or unbranched hydroxy or polyhydroxyalkyl groups or polyalkoxyalkyl or polyhydroxy-polyalkoxyalkyl groups, J is optional, but if present is C(=O)—, OC(=O)—, $SO_2$—, NC(=O)—, NC(=S)—, N(Y), NC(=$NCH_3$)—, NC(=NH)—, N=N—, homopolyamides or heteropolyamines derived from synthetic or naturally occurring amino acids; all where n is 1-100. Other variants of these structures are described, for example, in U.S. Pat. No. 6,093,382. In Formula 6, the group S—$NHCOCH_3$ may be replaced with SH or S-Z wherein Z is any of the known sulfur protecting groups such as those described above. Formula 7 illustrates one embodiment of t-butyl compounds useful as a metal chelator. The disclosures of each of the foregoing patents, applications and references are incorporated by reference herein, in their entirety.

In a preferred embodiment, the metal chelator includes cyclic or acyclic polyaminocarboxylic acids such as DOTA (1,4,7,10-tetraazacyclododecane-1,4,7,10tetraacetic acid), DTPA (diethylenetriaminepentaacetic acid), DTPA-bismethylamide, DTPA-bismorpholineamide, DO3A N-[[4,7,10-Tris(carboxymethyl)-1,4,7,10-tetraazacyclododec-1-yl] acetyl, HP-DO3A, DO3A-monoamide and derivatives thereof.

Preferred metal radionuclides for scintigraphy or radiotherapy include $^{99m}$Tc, $^{51}$Cr, $^{67}$Ga, $^{68}$Ga, $^{47}$SC, $^{51}$Cr, $^{167}$Tm, (5a)
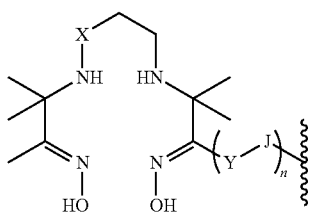

$^{141}$Ce, $^{111}$In, $^{168}$Yb, $^{175}$Yb, $^{140}$La, $^{90}$Y, $^{88}$Y, $^{153}$Sm, $^{166}$Ho, $^{165}$Dy, $^{166}$Dy, $^{62}$Cu, $^{64}$Cu, $^{67}$Cu, $^{97}$Ru, $^{103}$Ru, $^{186}$Re, $^{188}$Re, $^{203}$Pb, $^{211}$Bi, $^{212}$Bi, $^{213}$Bi, $^{214}$Bi, $^{105}$Rh, $^{109}$Pd, $^{117m}$Sn, $^{149}$Pm, $^{161}$Th, $^{177}$Lu, $^{198}$Au and $^{199}$Au and oxides or nitrides thereof. The choice of metal will be determined based on the desired therapeutic or diagnostic application. For example, for diagnostic purposes (e.g., to diagnose and monitor therapeutic progress in primary tumors and metastases), the preferred radionuclides include $^{64}$Cu, $^{67}$Ga, $^{68}$Ga, $^{99m}$Tc, and $^{111}$In, with $^{99m}$Tc and $^{111}$In being especially preferred. For therapeutic purposes (e.g., to provide radiotherapy for primary tumors and metastasis related to cancers of the prostate, breast, lung, etc.), the preferred radionuclides include $^{64}$Cu, $^{90}$Y, $^{105}$Rh, $^{111}$In, $^{117m}$Sn, $^{149}$Pm, $^{153}$Sm, $^{161}$Tb, $^{166}$Dy, $^{166}$Ho, $^{175}$Yb, $^{177}$Lu, $^{186}$Re, $^{188}$Re, and $^{199}$Au, with $^{177}$Lu, $^{90}$Y, $^{186}$Re and $^{188}$Re being particularly preferred. $^{99m}$Tc is particularly useful and is a preferred diagnostic radionuclide because of its low cost, availability, imaging properties, and high specific activity. The nuclear and radioactive properties of $^{99m}$Tc make this isotope an ideal scintigraphic imaging agent. This isotope has a single photon energy of 140 keV and a radioactive half-life of about 6 hours, and is readily available from a $^{99}$Mo-$^{99m}$Tc generator. For example, the $^{99m}$Tc labeled peptide can be used to diagnose and monitor therapeutic progress in primary tumors and metastases. Peptides labeled with $^{177}$Lu, $^{90}$Y or other therapeutic radionuclides can be used to provide radiotherapy for primary tumors and metastases related to cancers of the prostate, breast, lung, etc.

1B. Radioactive Halogens

In an alternative embodiment, the compounds of the present invention can be labeled by halogenation using radionuclides, such as $^{18}$F, $^{124}$I, $^{125}$I, $^{131}$I, $^{123}$I, $^{77}$Br, and $^{76}$Br instead of using a metal chelator to attach a metal radionuclide. The choice of metal or halogen radionuclides will be determined based on the desired therapeutic or diagnostic application.

2A. Other Diagnostic Moieties

In alternative embodiments, compounds of the present invention can incorporate other diagnostic moieties, such as agents which enable detection of the compounds by such techniques as x-ray, magnetic resonance imaging, ultrasound, fluorescence and other optical imaging methodologies, as described in more detail below. The choice of diagnostic moiety will be determined based on the desired application. In one embodiment, the compounds of the invention may be conjugated with photolabels, such as optical dyes, including organic chromophores or fluorophores, having extensive delocalized ring systems and having absorption or emission maxima in the range of 400-1500 nm. The compounds of the invention may alternatively be derivatized with a bioluminescent molecule. The preferred range of absorption maxima for photolabels is between 600 and 1000 nm to minimize interference with the signal from hemoglobin. Preferably, photo-absorption labels have large molar absorptivities, e.g.>$10^5$ cm$^{-1}$M$^{-1}$, while fluorescent optical dyes will have high quantum yields. Examples of optical dyes include, but are not limited to those described in WO 98/18497, WO 98/18496, WO 98/18495, WO 98/18498, WO 98/53857, WO 96/17628, WO 97/18841, WO 96/23524, WO 98/47538, and references cited therein. For example, the photolabels may be covalently linked directly to compounds of the invention, such as, for example, compounds comprised of targeting peptides or diagnostic or therapeutic moieties and linkers of the invention. Several dyes that absorb and emit light in the visible and near-infrared region of electromagnetic spectrum are currently being used for various biomedical applications due to their biocompatibility, high molar absorptivity, and/or high fluorescence quantum yields. The high sensitivity of the optical modality in conjunction with dyes as contrast agents parallels that of nuclear medicine, and permits visualization of organs and tissues without the undesirable effect of ionizing radiation. Cyanine dyes with intense absorption and emission in the near-infrared (NIR) region are particularly useful, because biological tissues are optically transparent in this region. For example, indocyanine green, which absorbs and emits in the NIR region has been used for monitoring cardiac output, hepatic functions, and liver blood flow and its functionalized derivatives have been used to conjugate biomolecules for diagnostic purposes (R. B. Mujumdar, L. A. Ernst, S. R. Mujumdar, et al., Cyanine dye labeling reagents: Sulfoindocyanine succinimidyl esters. Bioconjugate Chemistry, 1993, 4(2), 105-111; Linda G. Lee and Sam L. Woo. "N-Heteroaromatic ion and iminiun ion substituted cyanine dyes for use as fluorescent labels", U.S. Pat. No. 5,453,505; Eric Hohenschuh, et al. "Light imaging contrast agents", WO 98/48846; Jonathan Turner, et al. "Optical diagnostic agents for the diagnosis of neurodegenerative diseases by means of near infra-red radiation", WO 98/22146; Kai Licha, et al. "In-vivo diagnostic process by near infrared radiation", WO 96/17628; Robert A. Snow, et al., Compounds, WO 98/48838. Various imaging techniques and reagents are described in U.S. Pat. Nos. 6,663,847, 6,656,451, 6,641,798, 6,485,704, 6,423,547, 6,395,257, 6,280,703, 6,277,841, 6,264,920, 6,264,919, 6,228,344, 6,217,848, 6,190,641, 6,183,726, 6,180,087, 6,180,086, 6,180,085, 6,013,243, and published U.S. Patent Applications 2003185756, 20031656432, 2003158127, 2003152577, 2003143159, 2003105300, 2003105299, 2003072763, 2003036538, 2003031627, 2003017164, 2002169107, 2002164287, and 2002156117.

2B. Other Therapeutic Moieties

In alternative embodiments, compounds of the present invention can incorporate other therapeutic moieties such as antibiotics, hormones, enzymes, antibodies, growth factors, as described in more detail below. Alternatively, compounds of the invention may be administered in combination with a therapeutic moiety. The choice of therapeutic moiety will be determined based on the desired application. Suitable therapeutic moieties include, but are not limited to: antineoplastic agents, such as platinum compounds (e.g., spiroplatin, cisplatin, and carboplatin), methotrexate, adriamycin, mitomycin, ansamitocin, bleomycin, cytosine, arabinoside, arabinosyl adenine, mercaptopolylysine, vincristine, busulfan, chlorambucil, melphalan (e.g., PAM, a, L-PAM or phennylalanine mustard), mercaptopurine, mitotane. procarbazine hydrochloride, dactinomycin (actinomycin D), daunorubcin hydrochloride, doxorubicin hydrochloride, taxol, mitomycin, plicamycin (mithramycin), aminoglutethimide, estramustine phosphate sodium, flutamide, leuprolide acetate, megestrol acetate, tamoxifen citrate, testolactone, trilostane, amsacrine (m-AMSA), asparaginase (L-asparaginase) *Erwina aparaginase*, etoposide (VP-16), interferon α-2a, interferon α-2b, teniposide (VM-26), vinblastine sulfate (VLB), and arabinosyl; blood products such as parenteral iron, hemin, hematoporphyrins and their derivatives; biological response modifiers such as muramyldipeptide, muramyltripeptide; microbial cell wall components; lymphokines (e.g., bacterial endotoxin such as lipopolysaccharide, macrophage activation factor);

sub-units of bacteria (such as Mycobacteria, Corynebacteria); the synthetic dipeptide N-acetyl-muramyl-1-alanyl-I)-isoglutamine; anti-fungal agents such as ketoconazole, nystatin, griseofulvin, flucytosine (5-fc), miconazole, amphotericin B, ricin, and β-lactam antibiotics (e.g., sulfazecin); hormones such as growth hormone, melanocyte stimulating hormone, estradiol, beclomethasone, dipropionate, betamethasone, betamethasone acetate and betamethasone sodium phosphate, vetamethsone disodium phosphate, vetemthsone sodium phosphate, cortisoneacetate, dexamethasone, dexamethasone acetate, dexamethasone sodium phosphate, flunisolide, hydrocortisone, hydrocortisone acetate, hydrocortisone cupionate, hydrocortisone sodium phosphate, hydrocortisone sodium succinate, methylprednisolone, methylprednisolone acetate, methylprednisolone sodium succinate, paramethasone acetate, prednisolone, prednisotone acetate, prednisolone sodium phosphate, prednisolone tebutate, prednisone, triamcinolone, triamcinolone acetonide, triamcinolone diacetate, triameinolone hexacetonide and fludrocortisone acetate; vitamins such as cyanocobalamin neinoic acid, retinoids and derivatives such as retinol palmitate, and α-tocpherol; enzymes such as manganese super oxide dismutase or alkaline phosphatase; antiallergice agents such as amelexanox; anti-coagulation agents such as phenprocoumon and heparin; circulatory drugs such as propranolol; metabolic potentiators such as glutathione; antituberculars such as para-aminosalicylic acid, isoniazid, capreomycin sulfate cycloscrine, ethambutol hydrochloride ethionamide, pyrazinamide, rifampin, and streptomycin sulfate; antivirals such as acyclovir, amantadine azidothymidine (AZT or Zidovudine), ribavirin and vidarabine monohydrate (adenine arahinoside, ara-A); antianginals such as diltiazem, nifedipine, verapamil, erythritol tetranitrate, isosorbide dinitrate, nitroglycerin (glyceryl trinitrate) and pentaerythritol tetranitrate; antibiotics, anti-inflammatories such as diflunisal, ibuprofen, indomethacin, meclofenamate, mefenamic acid, naproxen, oxyphenbutazone, phenylbutazone, piroxicam, sulindac, tolmetin, aspirin and salicylates; anti-protozoans such as chloroquine, hydroxychloroquine, metroidazole, quinine and meglumine antimonate; antirheumatics such as penicillamine; narcotics such as paregoric; opiates such as codeine, heroin, methadone, morphine and opium; cardiac glycosides such as deslanoside, digitoxin, digoxin, digitalin and digitalis; neuromuscular blockers such as atracutrium mesylate, gallamice triethiodide, hexafluorenium bromide, metocurine iodide, pancuronium bromide, succinylcholine chloride (suxamethonium chloride), tubocurarine chloride and vecuronium bromide; sedatives (hypnotics) such as amobarbital, amobarbital sodium, aprobarbital, butabarbital sodium, chloral hydrate, ethchlorvynol, ethinamate, flurazepam hydrochloride, glutethimide, methotrimeprazine hydrochloride, methyprylon, midazolam hydrochloride, paraldehyde, pentobarbital, pentobarbital sodium, phenobarbital sodium, secobarbital sodium, talbutal, temazepam and triazolam; local anesthetics such as bupivacaine hydrochloride, chloroprocaine hydrochloride, etidocaine hydrochloride, lidocaine hydrochloride, mepivacaine hydrochloride, procaine hydrochloride and tetracaine hydrochloride; and general anesthetics such as droperidol, etomidate, fentanyl citrate with droperidol, ketamine hydrochloride, methohexital sodium and thiopental sodium. In certain embodiments, the therapeutic may be monoclonal antibody, such as a monoclonal antibody capable of binding to melanoma antigen.

3. Linkers Containing at Least One Substituted Bile Acid

In an exemplary embodiment of the present invention, the linker N-O-P contains at least one substituted bile acid. Thus, in this embodiment of the linker N-O-P, N is 0 (where 0 means it is absent), an alpha amino acid, a substituted bile acid or other linking group;

O is an alpha amino acid or a substituted bile acid; and

P is 0, an alpha amino acid, a substituted bile acid or other linking group, wherein at least one of N, O or P is a substituted bile acid.

Alpha amino acids are well known in the art and include naturally occurring and synthetic amino acids.

Bile acids are found in bile (a secretion of the liver) and are steroids having a hydroxyl group and a five carbon atom side chain terminating in a carboxyl group. In substituted bile acids, at least one atom such as a hydrogen atom of the bile acid is substituted with another atom, molecule or chemical group. For example, substituted bile acids include those having a 3-amino, 24-carboxyl function optionally substituted at positions 7 and 12 with hydrogen, hydroxyl or keto functionality.

Other useful substituted bile acids in the present invention include substituted cholic acids and derivatives thereof. Specific substituted cholic acid derivatives include:

(3β,5β)-3-aminocholan-24-oic acid;

(3β,5β,12α)-3-amino-12-hydroxycholan-24-oic acid;

(3β,5β,7α,12α)-3-amino-7,12-dihydroxycholan-24-oic acid;

Lys-(3,6,9)-trioxaundecane-1,11-dicarbonyl-3,7-dideoxy-3-aminocholic acid);

(3β,5β,7α)-3-amino-7-hydroxy-12-oxocholan-24-oic acid; and (3β,5β,7α)-3-amino-7-hydroxycholan-24-oic acid.

3A. Other Linking Groups

Other linking groups which may be used within the linker N-O-P include a chemical group that serves to couple the diagnostic or therapeutic moiety to the targeting peptide or the other diagnostic or therapeutic moiety while not adversely affecting either the targeting function of the targeting peptide or the diagnostic or therapeutic function of the diagnostic or therapeutic moiety. Suitable other linking groups include peptides (i.e., amino acids linked together) alone, a non-peptide group (e.g., hydrocarbon chain) or a combination of an amino acid sequence and a non-peptide spacer.

In one embodiment, other linking groups for use within the linker N-O-P include L-glutamine and hydrocarbon chains, or a combination thereof.

In another embodiment, other linking groups for use within the linker N-O-P include a pure peptide linking group consisting of a series of amino acids (e.g.; diglycine, triglycine, gly-gly-glu, gly-ser-gly, etc.).

In yet a further embodiment, other linking groups for use within the linker N-O-P can also include a hydrocarbon chain [i.e., $R_1$—$(CH_2)_n$—$R_2$] wherein n is 0-10, preferably n=3 to 9, $R_1$ is a group (e.g., $H_2N$—, HS—, —COOH) that can be used as a site for covalently linking the ligand backbone or the preformed metal chelator or metal complexing backbone or other diagnostic or therapeutic moiety; and $R_2$ is a group that is used for covalent coupling to the N-terminal $NH_2$-group of a given targeting peptide (e.g., $R_2$ is an activated COOH group) or other diagnostic or therapeutic moiety. Several chemical methods for conjugating ligands (i.e., chelators) or chelates (chelators/ligands complexed with a radionuclide) to biomolecules (such as targeting peptides) have been well described in the literature [Wilbur, 1992; Parker, 1990; Hermanson, 1996; Frizberg et al., 1995]. One or more of these methods could be used to link either the uncomplexed ligand (chelator) or the radiometal chelate or other diagnostic or therapeutic moiety to the linker or to link the linker to the targeting peptides or other diagnostic or therapeutic moiety. These methods include the formation of acid anhydrides, aldehydes, arylisothiocyanates, activated esters, or N-hydroxysuccinimides [Wilbur, 1992; Parker, 1990; Hermanson, 1996; Frizberg et al., 1995].

In a preferred embodiment, other linking groups for use within the linker N-O-P may be formed from linker precursors having electrophiles or nucleophiles as set forth below:

LP1: a linker precursor having on at least two locations of the linker the same electrophile E1 or the same nucleophile Nu1;

LP2: a linker precursor having an electrophile E1 and on another location of the linker a different electrophile E2;

LP3: a linker precursor having a nucleophile Nu1 and on another location of the linker a different nucleophile Nu2; or LP4: a linker precursor having one end functionalized with an electrophile E1 and the other with a nucleophile Nu1.

The preferred nucleophiles Nu1/Nu2 include —OH, —NH, —NR, —SH, —HN—NH$_2$, —RN—NH$_2$, and —RN—NHR', in which R' and R are independently selected from the definitions for R given above, but for R' is not H.

The preferred electrophiles E1/E2 include —COOH, —CH=O (aldehyde), —CR=OR' (ketone), —RN=C=S, —RN=C=O, —S-S-2-pyridyl, —SO$_2$—Y, —CH$_2$C(=O)Y, and

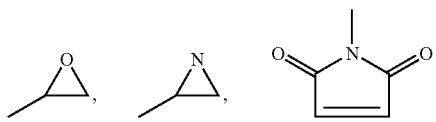

wherein Y can be selected from the following groups:

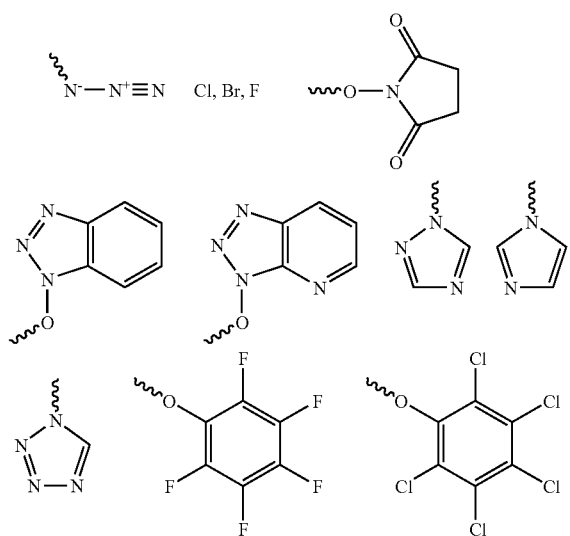

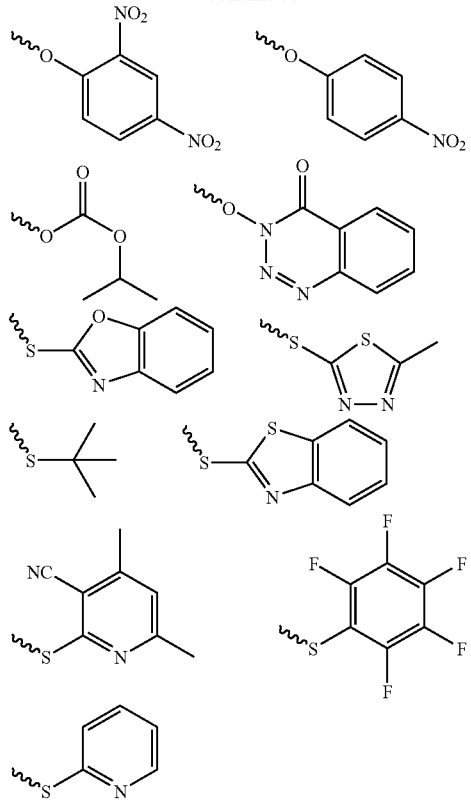

4. Targeting Moiety

The targeting moiety (i.e. Q in the formula M-N-O-P-Q) is any molecule that has a binding affinity for particular site or a specific metabolic function. The targeting moiety directs the compounds of the invention to the appropriate site, or involves the compounds in a reaction, where the desired diagnostic or therapeutic activity will occur. In an exemplary embodiment, the targeting moiety may be a peptide, equivalent, derivative or analog thereof which functions as a ligand that binds to a particular site. In another exemplary embodiment, the targeting moiety may be an enzyme, or a molecule that binds to an enzyme. In another exemplary embodiment, the targeting moiety may be an antibiotic.

In a preferred embodiment, the targeting peptide is a peptide that binds to a receptor or enzyme of interest. For example, the targeting peptide Q may be a peptide hormone such as, for example, luetinising hormone releasing hormone (LHRH) such as that described in the literature [e.g., Radiometal-Binding Analogues of Leutenizing Hormone Releasing Hormone PCT/US96/08695; PCT/US97/12084 (WO 98/02192)]; insulin; oxytosin; somatostatin; Neuro kinin-1 (NK-1); Vasoactive Intestinal Peptide (VIP) including both linear and cyclic versions as delineated in the literature, [e.g., Comparison of Cyclic and Linear Analogs of Vasoactive Intestinal Peptide. D. R. Bolin, J. M. Cottrell, R. Garippa, N. Rinaldi, R. Senda, B. Simkio, M. O'Donnell. Peptides: Chemistry, Structure and Biology Pravin T. P. Kaumaya, and Roberts S. Hodges (Eds). Mayflower Scientific LTD., 1996, pgs 174-175]; gastrin releasing peptide (GRP); bombesin and other known hormone peptides, as well as analogues and derivatives thereof.

Other useful targeting peptides include analogues of somatostatin which, for example, are Lanreotide (Nal-Cys-Thr-DTrp-Lys-Val-Cys-Thr-NH$_2$), Octreotide (Nal-Cys-Thr-DTrp-Lys-Val-Cys-Thr-ol), and Maltose (Phe-Cys-Thr-DTrp-Lys-Val-Cys-Thr-ol). These analogues are described in the literature [e.g., Potent Somatostatin Analogs Containing N-terminal Modifications, S. H. Kim, J. Z. Dong, T. D. Gordon, H. L. Kimball, S. C. Moreau, J.-P. Moreau, B. A. Morgan, W. A. Murphy and J. E. Taylor; Peptides: Chemistry, Structure and Biology Pravin T. P. Kaumaya, and Roberts S. Hodges (Eds), Mayflower Scientific LTD., 1996, pgs 241-243.]

Still other useful targeting peptides include Substance P agonists [e.g., G. Bitan, G. Byk, Y. Mahriki, M. Hanani, D. Halle, Z. Selinger, C. Gilon, Peptides: Chemistry, Structure and Biology, Pravin T. P. Kaumaya, and Roberts S. Hodges (Eds), Mayflower Scientific LTD., 1996, pgs 697-698; G Protein Antagonists A novel hydrophobic peptide competes with receptor for G protein binding, Hidehito Mukai, Eisuke Munekata, Tsutomu Higashijima, J. Biol. Chem. 1992, 267, 16237-16243]; NPY(Y1) [e.g., Novel Analogues of Neuropeptide Y with a Preference for the Y1-receptor, Richard M. Soll, Michaela, C. Dinger, Ingrid Lundell, Dan Larhammer, Annette G. Beck-Sickinger, Eur. J. Biochem. 2001, 268, 2828-2837; 99mTc-Labeled Neuropeptide Y Analogues as Potential Tumor Imaging Agents, Michael Langer, Roberto La Bella, Elisa Garcia-Garayoa, Annette G. Beck-Sickinger, Bioconjugate Chem. 2001, 12, 1028-1034; Novel Peptide Conjugates for Tumor-Specific Chemotherapy, Michael Langer, Felix Kratz, Barbara Rothen-Rutishauser, Heidi Wnderli-Allenspach, Annette G. Beck-Sickinger, J. Med. Chem. 2001, 44, 1341-1348]; oxytocin; endothelin A and endothelin B; bradykinin; Epidural Growth Factor (EGF); Interleukin-1 [Anti-IL-1 Activity of Peptide Fragments of IL-1 Family Proteins, I. Z. Siemion, A. Kluczyk, Zbigtniew Wieczorek, Peptides 1998, 19, 373-382]; and cholecystokinin (CCK-B) [Cholecystokinin Receptor Imaging Using an Octapeptide DTPA-CCK Analogue in Patients with Medullary Thryroid Carcinoma, Eur. J. Nucl Med. 200, 27, 1312-1317].

Literature which gives a general review of targeting peptides, can be found, for example, in the following: The Role of Peptides and Their Receptors as Tumor Markers, Jean-Claude Reubi, Gastrointestinal Hormones in Medicine, Pg 899-939; Peptide Radiopharmaceutical in Nuclear Medicine, D. Blok, R. I. J. Feitsma, P. Vermeij, E. J. K. Pauwels, Eur. J. Nucl Med. 1999, 26, 1511-1519; and Radiolabeled Peptides and Other Ligands for Receptors Overexpressed in Tumor Cells for Imaging Neoplasms, John G. McAfee, Ronald D. Neumann, Nuclear Medicine and Biology, 1996, 23, 673-676 (somatostatin, VIP, CCK, GRP, Substance P, Galanan, MSH, LHRH, Arginine-vasopressin, endothelin). All of the aforementioned literature in the preceding paragraphs are herein incorporated by reference in their entirety.

Other targeting peptide references include the following: Co-expressed peptide receptors in breast cancer as a molecular basis of in vivo multireceptor tumour targeting. Jean Claude Reubi, Mathias Gugger, Beatrice Waser. Eur. J. Nucl Med. 2002, 29, 855-862, (includes NPY, GRP); Radiometal-Binding Analogues of Leutenizing Hormone Releasing Hormone PCT/US96/08695 (LHRH); PCT/US97/12084 (WO 98/02192) (LHRH); PCT/EP90/01169 (radiotherapy of peptides); WO 91/01144 (radiotherapy of peptides); and PCT/EP00/01553 (molecules for the treatment and diagnosis of tumours), all of which are herein incorporated by reference in their entirety.

Additionally, analogues of a targeting peptide can be used. These analogues include molecules that target a desired site receptor with avidity that is greater than or equal to the targeting peptide itself, as well as muteins, retropeptides and retro-inverso-peptides of the targeting peptide. One of ordinary skill will appreciate that these analogues may also contain modifications which include substitutions, and/or deletions and/or additions of one or several amino acids, insofar that these modifications do not negatively alter the biological activity of the peptides described therein. These substitutions may be carried out by replacing one or more amino acids by their synonymous amino acids. Synonymous amino acids within a group are defined as amino acids that have sufficiently similar physicochemical properties to allow substitution between members of a group in order to preserve the biological function of the molecule. Synonymous amino acids as used herein include synthetic derivatives of these amino acids (such as for example the D-forms of amino acids and other synthetic derivatives).

Deletions or insertions of amino acids may also be introduced into the defined sequences provided they do not alter the biological functions of said sequences. Preferentially such insertions or deletions should be limited to 1, 2, 3, 4 or 5 amino acids and should not remove or physically disturb or displace amino acids which are critical to the functional conformation. Muteins of the peptides or polypeptides described herein may have a sequence homologous to the sequence disclosed in the present specification in which amino acid substitutions, deletions, or insertions are present at one or more amino acid positions. Muteins may have a biological activity that is at least 40%, preferably at least 50%, more preferably 60-70%, most preferably 80-90% of the peptides described herein. However, they may also have a biological activity greater than the peptides specifically exemplified, and thus do not necessarily have to be identical to the biological function of the exemplified peptides. Analogues of targeting peptides also include peptidomimetics or pseudopeptides incorporating changes to the amide bonds of the peptide backbone, including thioamides, methylene amines, and E-olefins. Also peptides based on the structure of a targeting peptide or its peptide analogues with amino acids replaced by N-substituted hydrazine carbonyl compounds (also known as aza amino acids) are included in the term analogues as used herein.

The targeting peptide may be attached to the linker via the N or C terminus or via attachment to the epsilon nitrogen of lysine, the gamma nitrogen or ornithine or the second carboxyl group of aspartic or glutamic acid.

In an exemplary embodiment, the targeting peptide Q is LHRH or an analogue or derivative thereof. For example, it is well known in the art that position 6 of LHRH agonists may be substituted with different functional groups, such as, for example DLysine. In a preferred embodiment the targeting peptide Q is an LHRH analogue of the formula PGlu-His-Trp-W-Tyr-DLys-X-Y-Pro-Z, wherein W=Ser, NMeSer, or Thr.

X=Leu, NMeLeu, t-ButylGly.

Y=Arg, Arg(Et2), Cit, Lys(isopropyl).
Z=Gly-NH$_2$, NHEthyl, Azagly-NH$_2$.
Linkers of the invention coupled to glycine and DLysine can be attached to the LHRH analogue at position 6. This embodiment includes compounds of the formula:

PGlu-His-Trp-W-Tyr-DLys(M-N-O-P)-X-Y-Pro-Z,
wherein

W=Ser, NMeSer, or Thr.
X=Leu, NMeLeu, t-ButylGly.
Y=Arg, Arg(Et2), Cit, Lys(isopropyl).
Z=Gly-NH$_2$, NHEthyl, Azagly-NH$_2$.
M is a metal chelator as defined herein, and
N-O-P is a linker of the invention In a particular preferred embodiment, the invention includes compounds of the formula:

PGlu-His-Trp-W-Tyr-DLys(DOTA-Gly-Cholic acid derivative)-X-Y-Pro-Z,

Here, DOTA-Gly is M (the metal chelator and a Gly spacer), N-O-P is a linker of the present invention (e.g., a cholic acid derivative), and Q is an LHRH incorporating DLys6 and the other substitutions listed above.

In a preferred embodiment, the W, X, Y or Z components in the above formulas are W=Ser, X=Leu, Y=Arg and Z=Gly-NH$_2$.

In another preferred embodiment, Q is a peptide which targets a receptor in the GRP receptor family, such as an analogue or derivative of GRP or bombesin. Such targeting peptides are discussed in co-pending U.S. Ser. No. 10/341,577 filed Jan. 13, 2003, as well as in U.S. Pat. No. 6,200,546, US 2002/0054855, US2003/0224998, and WO 02/87637 which are incorporated by reference in their entirety.

Examples of compounds having the formula M-N-O-P-Q which contain linkers with at least one substituted bile acid which are attached to a targeting peptide such as BBN(7-14) are listed in Table 1. These compounds may be prepared using the methods disclosed herein, particularly in the Examples, as well as by similar methods known to those skilled in the art.

TABLE 1

Compounds Containing Linkers With At Least One Substituted Bile Acid

| Compound | HPLC method[1] | HPLC RT[2] | MS[3] | IC50[5] | M | N | O | P | G* |
|---|---|---|---|---|---|---|---|---|---|
| L62 | 20-80% B | 3.79 | 1741.2 | >50 | DO3A-monoamide | Gly | (3β,5β)-3-aminocholan-24-oic acid | none | BBN(7-14) |
| L63 | 20-80% B | 3.47 | 1757.0 | 23 | DO3A-monoamide | Gly | (3β,5β,12α)-3-amino-12-hydroxycholan-24-oic acid | none | BBN(7-14) |
| L64 | 20-50% B | 5.31 | 1773.7 | 8.5 | DO3A-monoamide | Gly | (3β,5β,7α,12α)-3-amino-7,12-dihydroxycholan-24-oic acid | none | BBN(7-14) |
| L65 | 20-80% B | 3.57 | 2246.2 | >50 | DO3A-monoamide | Gly | Lys-(3,6,9-trioxaundecane-1,11-dicarbonyl-3,7-dideoxy-3-aminocholic acid) | Arg | BBN(7-14) |
| L66 | 20-80% | 3.79 | 2245.8 | >50 | (3β,5β,7α,12α)-3-amino-7,12-dihydroxycholan-24-oic acid-3,6,9-trioxaundecane-1,11-dicarbonyl | | Lys(DO3A-monoamide-Gly) | Arg | BBN(7-14) |
| L67 | 20-80% | 3.25 | 1756.9 | 4.5 | DO3A-monoamide | Gly | (3β,5β,7α,12α)-3-amino-12-oxacholan-24-oic acid | none | BBN(7-14) |
| L69 | 20-80% | 3.25 | 1861.27 | 8 | DO3A-monoamide | 1-amino-3,6-dioxaoctanoic acid | (3β,5β,7α,12α)-3-amino-7,12-dihydroxycholan-24-oic acid | none | BBN(7-14) |

*BBN(7-14) is [SEQ ID NO: 1]
[1]HPLC method refers to the 10 minute time for the HPLC gradient.
[2]HPLC RT refers to the retention time of the compound in the HPLC.
[3]MS refers to mass spectra where molecular weight is calculated from mass/unit charge (m/e).
[4]IC$_{50}$ refers to the concentration of compound to inhibit 50% binding of iodinated bombesin to a GRP receptor on cells.

wherein
W=Ser, NMeSer, or Thr.
X=Leu, NMeLeu, t-ButylGly.
Y=Arg, Arg(Et2), Cit, Lys(isopropyl).
Z=Gly-NH$_2$, NHEthyl, Azagly-NH$_2$.

As explained in more detail infra, compounds containing linkers of the invention and GRP-R targeting peptides demonstrated unexpectedly superior pharmacokinetics and tumor uptake in an animal model.

The targeting peptide can be prepared by various methods depending upon the selected chelator. The peptide can generally be most conveniently prepared by techniques generally established and known in the art of peptide synthesis, such as the solid-phase peptide synthesis (SPPS) approach. Solid-phase peptide synthesis (SPPS) involves the stepwise addition of amino acid residues to a growing peptide chain that is linked to an insoluble support or matrix, such as polystyrene. The C-terminal residue of the peptide is first anchored to a commercially available support with its amino group protected with an N-protecting agent such as a t-butyloxycarbonyl group (Boc) or a fluorenylmethoxycarbonyl (Fmoc) group. The amino protecting group is removed with suitable deprotecting agents such as TFA in the case of Boc or piperidine for Fmoc and the next amino acid residue (in N-protected form) is added with a coupling agent such as N,N'-dicyclohexylcarbodiimide (DCC), or N,N'-diisopropylcarbodiimide or 2-(1H-benzotriazol-1-yl)-1,1,3,3-tetraethyluronium hexafluorophosphate (HBTU). Upon formation of a peptide bond, the reagents are washed from the support After addition of the final residue, the peptide is cleaved from the support with a suitable reagent such as trifluoroacetic acid (TFA) or hydrogen fluoride (HF).

The linker may then be coupled to form a conjugate by reacting the free amino group of a selected residue of the targeting peptide with an appropriate functional group of the linker. The entire construct of chelator, linker and targeting moiety discussed above may also be assembled on resin and then cleaved by agency of suitable reagents such as trifluoroacetic acid or HF, as well.

5. Labeling And Administration Of Radiopharmaceutical Compounds

Incorporation of the metal within radiopharmaceutical conjugates of the invention can be achieved by various methods commonly known in the art of coordination chemistry. When the metal is $^{99m}$Tc, a preferred radionuclide for diagnostic imaging, the following general procedure can be used to form a technetium complex. A peptide-chelator conjugate solution is formed by initially dissolving the conjugate in water, dilute acid, or in an aqueous solution of an alcohol such as ethanol. The solution is then optionally degassed to remove dissolved oxygen. When an —SH group is present in the peptide, a thiol protecting group such as Acm (acetamidomethyl), trityl or other thiol protecting group may optionally be used to protect the thiol from oxidation. The thiol protecting group(s) are removed with a suitable reagent, for example with sodium hydroxide, and are then neutralized with an organic acid such as acetic acid (pH 6.0-6.5). Alternatively, the thiol protecting group can be removed in situ during technetium chelation. In the labeling step, sodium pertechnetate obtained from a molybdenum generator is added to a solution of the conjugate with a sufficient amount of a reducing agent, such as stannous chloride, to reduce technetium and is either allowed to stand at room temperature or is heated. The labeled conjugate can be separated from the contaminants $^{99m}$TcO$_4^-$ and colloidal $^{99m}$TcO$_2$ chromatographically, for example with a C-18 Sep Pak cartridge [Millipore Corporation, Waters Chromatography Division, 34 Maple Street, Milford, Mass. 01757] or by HPLC using methods known to those skilled in the art.

In an alternative method, the labeling can be accomplished by a transchelation reaction. In this method, the technetium source is a solution of technetium complexed with labile ligands prior to reaction with the selected chelator, thus facilitating ligand exchange with the selected chelator. Examples of suitable ligands for transchelation includes tartrate, citrate, gluconate, and heptagluconate. It will be appreciated that the conjugate can be labeled using the techniques described above, or alternatively, the chelator itself may be labeled and subsequently coupled to the peptide to form the conjugate; a process referred to as the "prelabeled chelate" method. Re and Tc are both in row VIIB of the Periodic Table and they are chemical congeners. Thus, for the most part, the complexation chemistry of these two metals with ligand frameworks that exhibit high in vitro and in vivo stabilities are the same [Eckelman, 1995] and similar chelators and procedures can be used to label with Re. Many $^{99m}$Tc or $^{186/188}$Re complexes, which are employed to form stable radiometal complexes with peptides and proteins, chelate these metals in their +5 oxidation state [Lister-James et al., 1997]. This oxidation state makes it possible to selectively place $^{99m}$Tc- or $^{186/188}$Re into ligand frameworks already conjugated to the biomolecule, constructed from a variety of $^{99m}$Tc(V) and/or $^{186/188}$Re(V) weak chelates (e.g., $^{99m}$Tc-glucoheptonate, citrate, gluconate, etc.) [Eckelman, 1995; Lister-James et al., 1997; Pollak et-al., 1996].

Labelling of a targeting peptide or other peptide-linker conjugate of the invention with radioactive halogens can be done using any method known in the art. The Examples describe several methods which may be used.

A conjugate labeled with a radionuclide metal, such as $^{99m}$Tc, can be administered to a mammal, including human patients or subjects, by intravenous, subcutaneous or intraperitoneal injection in a pharmaceutically acceptable carrier and/or solution such as salt solutions like isotonic saline. Radiolabeled scintigraphic imaging agents provided by the present invention are provided having a suitable amount of radioactivity. In forming $^{99m}$Tc radioactive complexes, it is generally preferred to form radioactive complexes in solutions containing radioactivity at concentrations of from about 0.01 millicurie (mCi) to 100 mCi per mL. Generally, the unit dose to be administered has a radioactivity of about 0.01 mCi to about 100 mCi, preferably 1 mCi to 30 mCi. The solution to be injected at unit dosage is from about 0.01 mL to about 10 mL. The amount of labeled conjugate appropriate for administration is dependent upon the distribution profile of the chosen conjugate in the sense that a rapidly cleared conjugate may need to be administered in higher doses than one that clears less rapidly. In vivo distribution and localization can be tracked by standard scintigraphic techniques at an appropriate time subsequent to administration; typically between thirty minutes and 180 minutes depending upon the rate of accumulation at the target site with respect to the rate of clearance at non-target tissue. For example, after injection of the diagnostic radionuclide-labeled compounds of the invention into the patient, a gamma camera calibrated for the gamma ray energy of the nuclide incorporated in the imaging agent can be used to image areas of uptake of the agent and quantify the amount of radioactivity present in the site. Imaging of the site in vivo can take place in a few minutes. However, imaging can take place, if desired, hours or even longer, after the radiolabeled peptide is injected into a patient. In most instances, a sufficient amount of the administered dose will accumulate in the area to be imaged within about 0.1 hour to permit the taking of scintiphotos.

The compounds of the present invention can be administered to a patient alone or as part of a composition that contains other components such as excipients, diluents, radical scavengers, stabilizers, and carriers, all of which are well-known in the art. The compounds can be administered to patients either intravenously or intraperitoneally.

There are numerous advantages associated with the present invention. The compounds made in accordance with the present invention form stable, well-defined $^{99m}$Tc or $^{186/188}$Re labeled compounds. Similar compounds of the invention can also be made by using appropriate chelator frameworks for the respective radiometals, to form stable, well-defined products labeled with $^{153}$Sm, $^{90}$Y, $^{166}$Ho, $^{105}$Rh, $^{199}$Au, $^{149}$Pm, $^{177}$LU, $^{111}$In or other radiometal. The radioactive material that does not reach (i.e., does not bind) the cancer cells is preferentially excreted efficiently into the urine with minimal retention of the radiometal in the kidneys.

6. Alternative Embodiments

As explained in more detail in the Examples, compounds containing the novel linkers of the present invention exhibit increased affinity for serum albumin, which decreases the rate of excretion for the compounds. These compounds thus exhibit longer half lives than compounds without linkers of the invention. Surprisingly, this property is exhibited both by compounds in which a targeting peptide is attached to an amino group of a cholic acid derivative linker of the invention, and also by compounds in which the targeting peptide is attached via a carboxylic acid group of the cholic acid derivative linker.

In an exemplary embodiment of the invention, the targeting peptide may be attached to a cholic acid derivative linker of the invention via an amino group at the 3-position. A diagnostic or therapeutic moiety is attached via a carboxylic acid group at the 24-position.

In another exemplary embodiment, the targeting peptide may be attached to a carboxylic acid group at the 24-position of the cholic acid derivative linker of the invention. A diagnostic or therapeutic moiety may be attached via an amino group at the 3-position of the linker. For example, in L62 (FIG. 6B) and L69 (FIG. 10B), the diagnostic moiety (a metal chelator) is attached at the 3-position and the targeting peptide (BBN[7-14] is attached at the 24-position of the cholic acid derivative linker.

Figure 4:
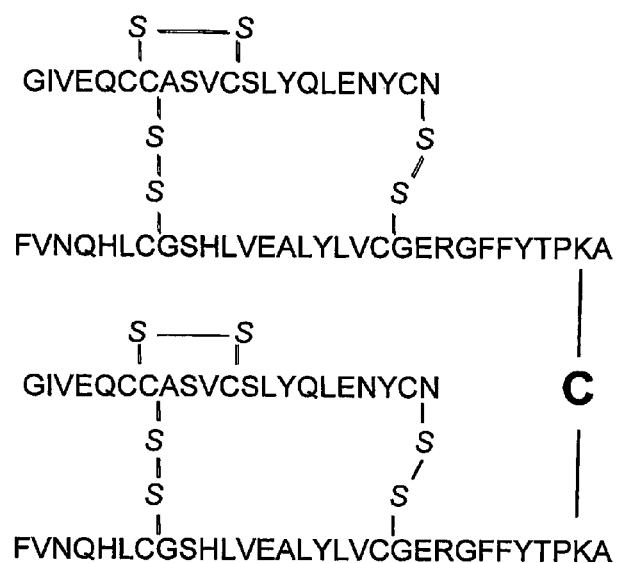
FIG. 4 is a chemical structure of bovine 1-[[(3β,5β,12α)-23-[(1,1-dimethyl)ethoxycarbonyl]-12-hydroxy-24-norcholan-3-yl]amino]carbonyl-3,5-bis[[4-(insulin-N$^{εB29}$-yl)-1,4-dioxobutyl]amino]benzene (Compound D), as described in Example III.
Figure 5A:
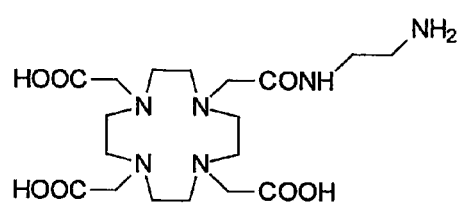
FIG. 5A is a chemical structure of N$^1$,N$^4$,N$^7$-triacetato-1, 4,7,10-tetraazacyclododecan-N$^{10}$-(2-acetamido ethylamine) (Compound E), as described in Example VII.
Figure 5B:
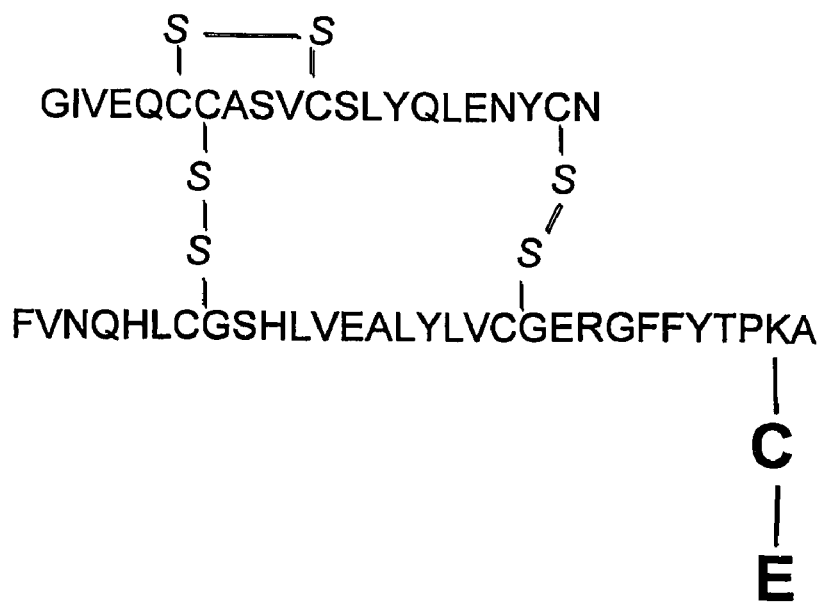
FIG. 5B is a chemical structure of Compound F, as described in Example VII.

In another exemplary embodiment, a diagnostic or therapeutic moiety may be attached to each of the amino and carboxyl groups of a cholic acid derivative linker. In a preferred exemplary embodiment, a compound has a therapeutic moiety (an insulin molecule) attached to the 3-amino group and another therapeutic moiety (an insulin molecule) attached to the 24-carboxyl group of a cholic acid derivative linker. See e.g. Compound D. (FIG. 4). In another preferred exemplary embodiment, a compound has a therapeutic moiety (an insulin molecule) attached to the 3-amino group and a diagnostic moiety (a metal chelator) attached to the 24-carboxyl group of a cholic acid derivative linker (or vice versa). See, e.g. Compound F (FIG. 5B).

The invention also includes an embodiment in which a targeting peptide and a diagnostic or therapeutic moiety (or two diagnostic and/or therapeutic moieties) may both be attached via an amino group at the 3-position of the cholic acid derivative linker. For example, in L65 (FIG. 9) and L66 (FIG. 10A) the diagnostic moiety (a metal chelator) and the targeting peptide (BBN[7-14]) are both attached at the 3-position of the cholic acid derivative linker of the invention.

7A. Diagnostic and Therapeutic Uses

When labeled with diagnostic and/or therapeutic moieties (such as, for example, diagnostically or therapeutically useful metals), compounds of the present invention can be used to treat and/or detect diseases such as cancers, including tumors, by procedures established in the arts of diagnostic imaging, radiodiagnostics and radiotherapeutics. [Bushbaum, 1995; Fischman et al., 1993; Schubiger et al., 1996; Lowbertz et al., 1994; Krenning et al., 1994].

Compounds of the invention, which, as explained in more detail in the Examples, show higher uptake in tumors in vivo than compounds without the novel linkers disclosed herein, exhibit an improved ability to target the desired receptor-expressing tissue (e.g. receptor expressing tumors). Thus, compounds of the invention are better able to image or deliver radiotherapy to these desired tissues. Indeed, as shown in the Examples, radiotherapy is more effective (and survival time increased) using compounds of the invention.

The diagnostic application of these compounds can be as a first line diagnostic screen for the presence of targeted cells using diagnostic imaging (such as, for example, scintigraphic, magnetic resonance, ultrasound, optical, photoacoustic or sonoluminescent imaging), as an agent for targeting selected tissue using hand-held radiation detection instrumentation in the field of radioimmuno guided surgery (RIGS), as a means to obtain dosimetry data prior to administration of the matched pair radiotherapeutic compound, and as a means to assess a targeted receptor population as a function of treatment over time.

The therapeutic application of these compounds can be defined either as an agent that will be used as a first line therapy in the treatment of a disease such as cancer, as a combination therapy where the therapeutic agents of the invention could be utilized in conjunction with adjuvant chemotherapy (e.g, with one of the other therapeutic agents disclosed herein), or as the therapeutic part of a matched pair therapeutic agent. The matched pair concept refers to a single unmetallated compound which can serve as both a diagnostic and a therapeutic agent depending on the radiometal that has been selected for binding to the appropriate chelate. If the chelator cannot accommodate the desired metals appropriate substitutions can be made to accommodate the different metal while maintaining the pharmacology such that the behaviour of the diagnostic compound in vivo can be used to predict the behaviour of the radiotherapeutic compound.

7B. Optical Imaging, Sonoluminescence, Photoacoustic Imaging and Phototherapy In accordance with the present invention, a number of optical parameters may be employed to determine the location of a target with in vivo light imaging after injection of the subject with an optically-labeled compound of the invention. Optical parameters to be detected in the preparation of an image may include transmitted radiation, absorption, fluorescent or phosphorescent emission, light reflection, changes in absorbance amplitude or maxima, and elastically scattered radiation. For example, biological tissue is relatively translucent to light in the near infrared (NIR) wavelength range of 650-1000 nm. NIR radiation can penetrate tissue up to several centimeters, permitting the use of compounds of the present invention to image target-containing tissue in vivo. The use of visible and near-infrared (NIR) light in clinical practice is growing rapidly. Compounds absorbing or emitting in the visible, NIR, or long-wavelength (UV-A, >350 nm) region of the electromagnetic spectrum are potentially useful for optical tomographic imaging, endoscopic visualization, and phototherapy.

A major advantage of biomedical optics lies in its therapeutic potential. Phototherapy has been demonstrated to be a safe and effective procedure for the treatment of various surface lesions, both external and internal. Dyes are important to enhance signal detection and/or photosensitizing of tissues in optical imaging and phototherapy. Previous studies have shown that certain dyes can localize in tumors and serve as a powerful probe for the detection and treatment of small cancers (D). A. Bellnier et al., Murine pharmacokinetics and antitumor efficacy of the photodynamic sensitizer 2-[1-hexyloxyethyl]-2-devinyl pyropheophorbide-a, J. Photochem. Photobiol., 1993, 20, pp. 55-61; G. A. Wagnieres et al., In vivo fluorescence spectroscopy and imaging for oncological applications, Photochem. Photobiol., 1998, 68, pp. 603-632; J. S. Reynolds et al., Imaging of spontaneous canine mammary tumors using fluorescent contrast agents, Photochem. Photobiol., 1999, 70, pp. 87-94). However, these dyes do not localize preferentially in malignant tissues.

In an exemplary embodiment, the compounds of the invention may be conjugated with photolabels, such as optical dyes, including organic chromophores or fluorophores, having extensive delocalized ring systems and having absorption or emission maxima in the range of 400-1500 nm. The compounds of the invention may alternatively be derivatized with a bioluminescent molecule. The preferred range of absorption maxima for photolabels is between 600 and 1000 nm to minimize interference with the signal from hemoglobin. Preferably, photoabsorption labels have large molar absorptivities, e.g. >105 cm$^{-1}$M$^{-1}$, while fluorescent optical dyes will have high quantum yields. Examples of optical dyes include, but are not limited to those described in WO 98/18497, WO 98/18496, WO 98/18495, WO 98/18498, WO 98/53857, WO 96/17628, WO 97/18841, WO 96/23524, WO 98/47538, and references cited therein. For example, the photolabels may be covalently linked directly to compounds of the invention, such as, for example, compounds comprised of targeting moieties and linkers of the invention or compounds comprised of diagnostic and/or therapeutic moieties and linkers of the invention.

Several dyes that absorb and emit light in the visible and near-infrared region of electromagnetic spectrum are currently being used for various biomedical applications due to their biocompatibility, high molar absorptivity, and/or high fluorescence quantum yields. The high sensitivity of the optical modality in conjunction with dyes as contrast agents parallels that of nuclear medicine, and permits visualization of organs and tissues without the undesirable effect of ionizing radiation. Cyanine dyes with intense absorption and emission in the near-infrared (NIR) region are particularly useful because biological tissues are optically transparent in this region (B. C. Wilson, Optical properties of tissues. Encyclopedia of Human Biology, 1991, 5, 587-597). For example, indocyanine green, which absorbs and emits in the NIR region has been used for monitoring cardiac output, hepatic functions, and liver blood flow (Y-L. He, H. Tanigami, H. Ueyama, T. Mashimo, and I. Yoshiya, Measurement of blood volume using indocyanine green measured with pulse-spectrometry: Its reproducibility and reliability. Critical Care Medicine, 1998, 26(8), 1446-1451; J. Caesar, S. Shaldon, L. Chiandussi, et al., The use of Indocyanine green in the measurement of hepatic blood flow and as a test of hepatic function. Clin. Sci. 1961, 21, 43-57) and its functionalized derivatives have been used to conjugate biomolecules for diagnostic purposes (R. B. Mujumdar, L. A. Ernst, S. R. Mujumdar, et al., Cyanine dye labeling reagents: Sulfoindocyanine succinimidyl esters. Bioconjugate Chemistry, 1993, 4(2), 105-111; Linda G. Lee and Sam L. Woo. "N-Heteroaromatic ion and iminium ion substituted: cyanine dyes for use as fluorescent labels", U.S. Pat. No. 5,453,505; Eric Hohenschuh, et al. "Light imaging contrast agents", WO 98/48846; Jonathan Turner, et al. "Optical diagnostic agents for the diagnosis of neurodegenerative diseases by means of near infra-red radiation", WO 98/22146; Kai Licha, et al. "In-vivo diagnostic process by near infrared radiation", WO 96/17628; Robert A. Snow, et al., Compounds, WO 98/48838.

After injection of the optically-labeled compound, the patient is scanned with one or more light sources (e.g., a laser) in the wavelength range appropriate for the photolabel employed in the agent. The light used may be monochromatic or polychromatic and continuous or pulsed. Transmitted, scattered, or reflected light is detected via a photodetector tuned to one or multiple wavelengths to determine the location of target-containing tissue in the subject. Changes in the optical parameter may be monitored over time to detect accumulation of the optically-labeled reagent at the target site. Standard image processing and detecting devices may be used in conjunction with the optical imaging reagents of the present invention.

The optical imaging reagents described above may also be used for acousto-optical or sonoluminescent imaging performed with optically-labeled imaging agents (see, U.S. Pat. No. 5,171,298, WO 98/57666, and references therein). In acousto-optical imaging, ultrasound radiation is applied to the subject and affects the optical parameters of the transmitted, emitted, or reflected light. In sonoluminescent imaging, the applied ultrasound actually generates the light detected. Suitable imaging methods using such techniques are described in WO 98/57666.

Various imaging techniques and reagents are described in U.S. Pat. Nos. 6,663,847, 6,656,451, 6,641,798, 6,485,704, 6,423,547, 6,395,257, 6,280,703, 6,277,841, 6,264,920, 6,264,919, 6,228,344, 6,217,848, 6,190,641, 6,183,726, 6,180,087, 6,180,086, 6,180,085, 6,013,243, and published U.S. Patent Applications 2003185756, 20031656432, 2003158127, 2003152577, 2003143159, 2003105300, 2003105299, 2003072763, 2003036538, 2003031627, 2003017164, 2002169107, 2002164287, and 2002156117.

7C. Magnetic Resonance Imaging

The compounds of the present invention may advantageously be conjugated with one or more paramagnetic metal chelates in order to form a contrast agent for use in MRI. Preferred paramagnetic metal ions have atomic numbers 21-29, 42, 44, or 57-83. This includes ions of the transition metal or lanthanide series which have one, and more preferably five or more, unpaired electrons and a magnetic moment of at least 1.7 Bohr magneton. Preferred paramagnetic metals include, but are not limited to, chromium (III), manganese (II), manganese (III), iron (II), iron (III), cobalt (II), nickel (II), copper (II), praseodymium (III), neodymium (III), samarium (III), gadolinium (III), terbium (III), dysprosium (III), holmium (III), erbium (III), europium (III) and ytterbium (III). Additionally, compounds of the present invention may also be conjugated with one or more superparamagnetic particles.

Gd(III) is particularly preferred for MRI due to its high relaxivity and low toxicity, and the availability of only one biologically accessible oxidation state. Gd(III) chelates have been used for clinical and radiologic MR applications since 1988, and approximately 30% of MR exams currently employ a gadolinium-based contrast agent.

One skilled in the art will select a metal according to dose required to detect target containing tisssue and considering other factors such as toxicity of the metal to the subject. See, Tweedle et al., *Magnetic Resonance Imaging* (2nd ed.), vol. 1, Partain et al., eds. (W.B. Saunders Co. 1988), pp. 796-7. Generally, the desired dose for an individual metal will be proportional to its relaxivity, modified by the biodistribution, pharmacokinetics and metabolism of the metal. The trivalent cation, $Gd^{3+}$ is particularly preferred for MRI contrast agents, due to its high relaxivity and low toxicity, with the further advantage that it exists in only one biologically accessible oxidation state, which minimnizes undesired metabolization of the metal by a patient. Another useful metal is $Cr^{3+}$, which is relatively inexpensive.

The paramagnetic metal chelator is a molecule having one or more polar groups that act as a ligand for, and complex with, a paramagnetic metal. Suitable chelators are known in the art and include acids with methylene phosphonic-acid groups, methylene carbohydroxamine acid groups, carboxyethylidene groups, or carboxymethylene groups. Examples of chelators include, but are not limited to, diethylenetriamine pentaacetic acid (DTPA), 1,4,7,10-tetraazacyclotetradecane-1,4,7,10-tetraacetic acid (DOTA), 1-substituted 1,4,7,-tricarboxymethyl 1,4,7,10 teraazacyclododecane triacetic acid (DO3A), ethylenediaminetetraacetic acid (EDTA), and 1,4,8,11-tetraazacyclotetradecane-1,4,8,11-tetraacetic acid (TETA). Additional chelating ligands are ethylenebis-(2-hydroxy-phenylglycine) (EHPG), and derivatives thereof, including 5-Cl-EHPG, 5Br-EHPG, 5-Me-EHPG, 5t-Bu-EHPG, and 5sec-Bu-EHPG; benzodiethylenetriamine pentaacetic acid (benzo-DTPA) and derivatives thereof, including dibenzo-DTPA, phenyl-DTPA, diphenyl-DTPA, benzyl-DTPA, and dibenzyl DTPA; bis-2 (hydroxybenzyl)-ethylenediaminediacetic acid (HBED) and derivatives thereof; the class of macrocyclic compounds which contain at least 3 carbon atoms, more preferably at least 6, and at least two heteroatoms (O and/or N), which macrocyclic compounds can consist of one ring, or two or three rings joined together at the hetero ring elements, e.g., benzo-DOTA, dibenzo-DOTA, and benzo-NOTA, where NOTA is 1,4,7-triazacyclononane N,N',N"-triacetic acid, benzo-TETA, benzo-DOTMA, where DOTMA is 1,4,7,10-tetraazacyclotetradecane-1,4,7,10-tetra (methyl tetraacetic acid), and benzo-TETMA, where TETMA is 1,4,8,11-tetraazacyclotetradecane-1,4,8,11-(methyl tetraacetic acid); derivatives of 1,3-propylenediaminetetraacetic acid (PDTA) and triethylenetetraaminehexaacetic acid (TTHA); derivatives of 1,5,10-N,N',N"-tris(2,3-dihydroxybenzoyl)-tricatecholate (LICAM) and 1,3,5-N,N',N"-tris(2,3-dihydroxybenzoyl) aminomethylbenzene (MECAM). A preferred chelator for use in the present invention is DTPA. Examples of representative chelators and chelating groups contemplated by the present invention are described in WO 98/18496, WO 86/06605, WO 91/03200, WO 95/28179, WO 96/23526, WO 97/36619, PCT/US98/01473, PCT/US98/20182, and U.S. Pat. Nos. 4,899,755, 5,474,756, 5,846,519 and 6,143,274, each of which is hereby incorporated by reference in its entirety. Use of the chelate DO3A is particularly preferred.

As with chelators for radionuclides, chelators for paramagnetic metals may include a spacer group as defined supra.

In general, methods disclosed herein as well as other known methods can be used to couple the metal chelate and a compound comprising a linker of the invention. See, e.g., WO 95/28967, WO 98/18496, WO 98/18497 and discussion therein. The present invention contemplates linking of the chelate(s) on any position, provided the metal chelate retains the ability to bind the metal tightly in order to minimize toxicity. Similarly, a component of a compound of this invention may be modified or elongated in order to generate a locus for attachment to a metal chelate, provided such modification or elongation does not eliminate its ability to bind the target.

MRI contrast reagents prepared according to the disclosures herein may be used in the same manner as conventional MRI contrast reagents. When imaging target containing tissue such as, for example, a site of angiogenesis, certain MR techniques and pulse sequences may be preferred to enhance the contrast of the site to the background blood and tissues. These techniques include (but are not limited to), for example, black blood angiography sequences that seek to make blood dark, such as fast spin echo sequences (see, e.g., Alexander et al., *Magnetic Resonance in Medicine*, 40(2): 298-310 (1998))- and flow-spoiled gradient echo sequences (see, e.g., Edelman et al., *Radiology*, 177(1): 45-50 (1990)). These methods also include flow independent techniques that enhance the difference in contrast, such as inversion-recovery prepared or saturation-recovery prepared sequences that will increase the contrast between target containing tissue, such as an angiogenic tumor, and background tissues. Finally, magnetization transfer preparations may also improve contrast with these agents (see, e.g., Goodrich et al, *Investigative Radiology*, 31(6): 323-32 (1996)).

The labeled reagent is administered to the patient in the form of an injectable composition. The method of administering the MRI contrast agent is preferably parenterally, meaning intravenously, intraarterially, intrathecally, interstitially, or intracavitarilly. For imaging active angiogenesis, intravenous or intraarterial administration is preferred.

For MRI, it is contemplated that the subject will receive a dosage of contrast agent sufficient to enhance the MR signal at the target (e.g. a site of angiogenesis) at least 10%. After injection of the compound construct including the MRI reagent, the patient is scanned in the MRI machine to determine the location of any sites containing the target. In therapeutic settings, upon target localization, a cytotoxic or therapeutic agent can be immediately administered, if necessary, and the patient can be subsequently scanned to visualize the therapeutic effect.

In a preferred embodiment, compounds including linkers of the invention and targeting peptides or therapeutic moieties are conjugated to one or more paramagnetic metal chelates or one or more superparamagnetic particles. Such compound constructs are complexed with one or more paramagnetic metals and administered in a dose sufficient to enhance the MR signal at the site at least 10%. After injection, the patient is scanned to determine the location of any targeted sites.

7D. Ultrasound Imaging

When ultrasound is transmitted through a substance, the acoustic properties of the substance will depend upon the velocity of the transmissions and the density of the substance. Changes in the acoustic properties will be most prominent at the interface of different substances (solids, liquids, gases). Ultrasound contrast agents are intense sound wave reflectors because of the acoustic differences between the agent and the surrounding tissue. Gas containing or gas generating ultrasound contrast agents are particularly useful because of the acoustic difference between liquid (e.g., blood) and the gas-containing or gas generating ultrasound contrast agent. Because of their size, ultrasound contrast agents comprising microbubbles, microballoons, and the like may remain for a longer time in the blood stream after injection than other detectable moieties; thus a targeted ultrasound agent may demonsrate superior imaging of tissue expressing or containing the target.

In this aspect of the invention, the compound constructs of the invention may include as the diagnostic moiety a material that is useful for ultrasound imaging. For example, compounds comprising linkers of the invention and a targeting moiety, another diagnostic moiety or a therapeutic moiety, may be linked to materials employed to form vesicles (e.g., microbubbles, microballoons, microspheres, etc.), or emulsions containing a liquid or gas which functions as the detectable label (e.g., an echogenic gas or material capable of generating an echogenic gas). Materials for the preparation of such vesicles include surfactants, lipids, sphingolipids, oligolipids, phospholipids, proteins, polypeptides, carbohydrates, and synthetic or natural polymeric materials. See e.g. WO 98/53857, WO 98/18498, WO 98/18495, WO 98/18497, WO 98/18496, and WO 98/18501 incorporated herein by reference in their entirety.

For contrast agents comprising suspensions of stabilized microbubbles (a preferred embodiment), phospholipids, and particularly saturated phospholipids are preferred. The preferred gas-filled microbubbles can be prepared by means known in the art, such as, for example, by a method described in any one of the following patents: EP 554213, U.S. Pat. Nos. 5,413,774, 5,578,292, EP 744962, EP 682530, U.S. Pat. Nos. 5,556,610, 5,846,518, 6,183,725, EP 474833, U.S. Pat. Nos. 5,271,928, 5,380,519, 5,531,980, 5,567,414, 5,658,551, 5,643,553, 5,911,972, 6,110,443, 6,136,293, EP 619743, U.S. Pat. Nos. 5,445,813, 5,597,549, 5,686,060, 6,187,288, and 5,908,610, each of which is incorporated by reference herein in its entirety. In a preferred embodiment, at least one of the phospholipid moieties has the structure described in U.S. Pat. No. 5,686,060, which is herein incorporated by reference in its entirety.

Examples of suitable phospholipids include esters of glycerol with one or two molecules of fatty acids (the same or different) and phosphoric acid, wherein the phosphoric acid residue is in turn bonded to a hydrophilic group, such as choline, serine, inositol, glycerol, ethanolamine, and the like groups. Fatty acids present in the phospholipids are in general long chain aliphatic acids, typically containing from 12 to 24 carbon atoms, preferably from 14 to 22, that may be saturated or may contain one or more unsaturations. Examples of suitable fatty acids are lauric acid, myristic acid, palmitic acid, stearic acid, arachidic acid, behenic acid, oleic acid, linoleic acid, and linolenic acid. Mono esters of phospholipid are also known in the art as the "lyso" forms of the phospholipids.

Further examples of phospholipids are phosphatidic acids, i.e. the diesters of glycerol-phosphoric acid with fatty acids, sphingomyelins, i.e. those phosphatidylcholine analogs where the residue of glycerol diester with fatty acids is replaced by a ceramide chain, cardiolipins, i.e. the esters of 1,3-diphosphatidylglycerol with a fatty acid, gangliosides, cerebrosides, etc.

As used herein, the term phospholipids includes either naturally occurring, semisynthetic or synthetically prepared products that can be employed either singularly or as mixtures. Examples of naturally occurring phospholipids are natural lecithins (phosphatidylcholine (PC) derivatives) such as, typically, soya bean or egg yolk lecithins. Examples of semisynthetic phospholipids are the partially or fully hydrogenated derivatives of the naturally occurring lecithins. Examples of synthetic phospholipids are e.g., dilauryloyl-phosphatidylcholine ("DLPC"), dimyristoylphosphatidylcholine ("DMPC"), dipalmitoyl-phosphatidylcholine ("DPPC"), diarachidoylphosphatidylcholine ("DAPC"), distearoyl-phosphatidylcholine ("DSPC"), 1-myristoyl-2-palmitoylphosphatidylcholine ("MPPC"), 1-palmitoyl-2-myristoylphosphatidylcholine ("PMPC"), 1-palmitoyl-2-stearoylphosphatid-ylcholine ("PSPC"), 1-stearoyl-2-palmitoylphosphatidylcholine ("SPPC"), dioleoylphosphatidylycholine ("DOPC"), 1,2 Distearoyl-sn-glycero-3-Ethylphosphocholine (Ethyl-DSPC), dilauryloyl-phosphatidylglycerol ("DLPG") and its alkali metal salts, diarachidoylphosphatidylglycerol ("DAPG") and its alkali metal salts, dimyristoylphosphatidylglycerol ("DMPG") and its alkali metal salts, dipalmitoyl-phosphatidylglycerol ("DPPG") and its alkali metal salts, distearolyphosphatidylglycerol ("DSPG") and its alkali metal salts, dioleoylphosphatidylglycerol ("DOPG") and its alkali metal salts, dimyristoyl phosphatidic acid ("DMPA") and its alkali metal salts, dipalmitoyl phosphatidic acid ("DPPA") and its alkali metal salts, distearoyl phosphatidic acid ("DSPA"), diarachidoyl phosphatidic acid ("DAPA") and its alkali metal salts, dimyristoyl phosphatidyl-ethanolamine ("DMPE"), dipalmitoyl phosphatidylethanolamine ("DPPE"), distearoyl phosphatidyl-ethanolamine ("DSPE"), dimyristoyl phosphatidylserine ("DMPS"), diarachidoyl phosphatidylserine ("DAPS"), dipalmitoyl phosphatidylserine ("DPPS"), distearoylphosphatidylserine ("DSPS"), dioleoylphosphatidylserine ("DOPS"), dipalmitoyl sphingomyelin ("DPSP"), and distearoyl sphingomyelin ("DSSP").

Other preferred phospholipids include dipalmitoylphosphatidylcholine, dipalmitoylphosphatidic acid and dipalmitoylphosphatidylserine. The compositions may also contain PEG4000 and/or palmitic acid. Any of the gases disclosed herein or known to the skilled artisan may be employed; however, inert gases, such as $SF_6$, or fluorocarbons, such as $CF_4$, $C_3F_8$ and $C_4F_{10}$, are preferred.

The preferred microbubble suspensions may be prepared from phospholipids using known processes such as a freeze-drying or spray-drying solutions of the crude phospholipids in a suitable solvent or using the processes set forth in EP 554213, U.S. Pat. Nos. 5,413,774, 5,578,292, EP 744962, EP 682530, U.S. Pat. Nos. 5,556,610, 5,846,518, 6,183,725, EP 474833, U.S. Pat. Nos. 5,271,928, 5,380,519, 5,531,980, 5,567,414, 5,658,551, 5,643,553, 5,911,972, 6,110,443, 6,136,293, EP 619743, U.S. Pat. Nos. 5,445,813, 5,597,549, 5,686,060, 6,187,288, and 5,908,610, each of which is incorporated by reference herein in its entirety. Most preferably, the phospholipids are dissolved in an organic solvent and the solution is dried without going through a liposome formation stage. This can be done by dissolving the phospholipids in a suitable organic solvent together with a hydrophilic stabilizer substance or a compound soluble both in the organic solvent and water and freeze-drying or spray-drying the solution. In this embodiment the criteria used for selection of the hydrophilic stabilizer is its solubility in the organic solvent of choice. Examples of hydrophilic stabilizer compounds soluble in water and the organic solvent are e.g. a polymer, like polyvinyl pyrrolidone (PVP), polyvinyl alcohol (PVA), polyethylene glycol (PEG), etc., malic acid, glycolic acid, maltol and the like. Such hydrophilic compounds also aid in homogenizing the microbubbles size distribution and enhance stability under storage. Any suitable organic solvent may be used as long as its boiling point is sufficiently low and its melting point is sufficiently high to facilitate subsequent drying. Typical organic solvents include, for example, dioxane, cyclohexanol, tertiary butanol, tetrachlorodifluoro ethylene ($C_2Cl_4F_2$) or 2-methyl-2-butanol however, 2-methyl-2-butanol and $C_2Cl_4F_2$ are preferred.

Prior to formation of the suspension of microbubbles by dispersion in an aqueous carrier, the freeze-dried or spray-dried phospholipid powders are contacted with air or another gas. When contacted with the aqueous carrier the powdered phospholipids whose structure has been disrupted will form lamellarized or laminarized segments that will stabilize the microbubbles of the gas dispersed therein. This method permits production of suspensions of microbubbles that are stable even when stored for prolonged periods and are obtained by simple dissolution of the dried laminarized phospholipids (which have been stored under a desired gas) without shaking or any violent agitation.

Alternatively, microbubbles can be prepared by suspending a gas into an aqueous solution at high agitation speed, as disclosed e.g. in WO 97/29783. A further process for preparing microbubbles is disclosed in co-pending European patent application no. 03002373, herein incorporated by reference, which comprises preparing an emulsion of an organic solvent in an aqueous medium in the presence of a phospholipid andsubsequently lyophilizing said emulsion, after optional washing and/or filtration steps.

Additives known to those of ordinary skill in the art can be included in the suspensions of stabilized microbubbles. For instance, non-film forming surfactants, including polyoxypropylene glycol and polyoxyethylene glycol and similar compounds, as well as various copolymers thereof; fatty acids such as myristic acid, palmitic acid, stearic acid, arachidic acid or their derivatives, ergosterol, phytosterol, sitosterol, lanosterol, tocopherol, propyl gallate, ascorbyl palmitate and butylated hydroxytoluene may be added. The amount of these non-film forming surfactants is usually up to 50% by weight of the total amount of surfactants but preferably between 0 and 30% by weight.

Other gas containing suspensions include those disclosed in, for example, U.S. Pat. No. 5,798,091 and WO 97/29783, incorporated herein by reference in their entirety. These agents may be prepared as described in U.S. Pat. No. 5,798, 091 or WO97/29783, each of which is incorporated by reference in its entirety.

Another preferred ultrasound contrast agent comprises microballoons. The term "microballoon" refers to gas filled bodies with a material boundary or envelope. More on microballoon formulations and methods of preparation may be found in EP-A-0 324 938 U.S. Pat. Nos. 4,844,882; 5,711, 933; 5,840,275; 5,863,520; 6,123,922; 6,200,548; 4,900,540; 5,123,414; 5,230,882; 5,469,854; 5,585,112; 4,718,433; 4,774,958; WO 9501187; U.S. Pat. Nos. 5,529,766; 5,536, 490 and 5,990,263, each of which is incorporated herein by reference in its entirety.

The preferred microballoons have an envelope including a biodegradable physiologically compatible polymer or, a biodegradable solid lipid. The polymers useful for the preparation of the microballoons of the present invention can be selected from the biodegradable physiologically compatible polymers, such as any of those described in any of the following patents: EP 458745, U.S. Pat. Nos. 5,711,933, 5,840, 275, EP 554213, U.S. Pat. Nos. 5,413,774 and 5,578,292, the entire contents of which are incorporated herein by reference. In particular, the polymer can be selected from biodegradable physiologically compatible polymers, such as polysaccharides of low water solubility, polylactides and polyglycolides and their copolymers, copolymers of lactides and lactones such as $\epsilon$-caprolactone, $\gamma$-valerolactone and polypeptides. Other suitable polymers include poly(ortho)esters (see e.g., U.S. Pat. Nos. 4,093,709; 4,131,648; 4,138,344; 4,180,646); polylactic and polyglycolic acid and their copolymers, for instance DEXON (see J. Heller, Biomaterials 1 (1980), 51; poly(DL-lactide-co-$\epsilon$-caprolactone), poly(DL-lactide-co-$\gamma$-valerolactone), poly(DL-lactide-co-$\gamma$-butyrolactone), polyalkylcyanoacrylates; polyamides, polyhydroxybutyrate; polydioxanone; poly-$\beta$-aminoketones (A. S. Angeloni, P. Ferruti, M. Tramontini and M. Casolaro, The Mannich bases in polymer synthesis: 3. Reduction of poly(beta-aminoketone)s to poly(gamma-aminoalcohol)s and their N-alkylation to poly(gamma-hydroxyquaternary ammonium salt)s, Polymer 23, pp 1693-1697, 1982.); polyphosphazenes (Allcock, Harry R. Polyphosphazenes: new polymers with inorganic backbone atoms (Science 193(4259), 1214-19 (1976)) and polyanhydries. The microballoons of the present invention can also be prepared according to the methods of WO-A-96/15815, incorporated herein by reference, where the microballoons are made from a biodegradable membrane comprising biodegradable lipids, preferably selected from mono-di-, triglycerides, fatty acids, sterols, waxes and mixtures thereof. Preferred lipids are di- or tri-glycerides, e.g. di- or tri-myristin, -palmityn or -stearin, in particular tripalmitin or tristearin.

The microballoons may employ any of the gases disclosed herein or known to the skilled artisan; however, inert gases such as fluorinated gases are preferred. The microballoons may be suspended in a pharmaceutically acceptable liquid carrier with optional additives known to those of ordinary skill in the art and stabilizers.

Other gas-containing contrast agent formulations include microparticles (especially aggregates of microparticles) having gas contained therein or otherwise associated therewith (for example being adsorbed on the surface thereof and/or contained within voids, cavities or pores therein). Methods for the preparation of these agents are as described in EP 0122624, EP 0123235, EP 0365467, U.S. Pat. Nos. 5,558, 857, 5,607,661, 5,637,289, 5,558,856, 5,137,928, WO 9521631 and WO 9313809, each of which is incorporated herein by reference in its entirety.

Any of these ultrasound compositions should also be, as far as possible, isotonic with blood. Hence, before injection, small amounts of isotonic agents may be added to any of above ultrasound contrast agent suspensions. The isotonic agents are physiological solutions commonly used in medicine and they comprise aqueous saline solution (0.9% NaCl), 2.6% glycerol solution, 5% dextrose solution, etc. Additionally, the ultrasound compositions may include standard pharmaceutically acceptable additives, including, for example, emulsifying agents, viscosity modifiers, cryoprotectants, lyoprotectants, bulking agents etc.

Any biocompatible gas may be used in the ultrasound contrast agents useful in the invention. The term "gas" as used herein includes any substances (including mixtures) substantially in gaseous form at the normal human body temperature. The gas may thus include, for example, air; nitrogen; oxygen; $CO_2$; argon; xenon or krypton, fluorinated gases (including for example, perfluorocarbons, $SF_6$, $SeF_6$) a low molecular weight hydrocarbon (e.g. containing from 1 to 7 carbon atoms), for example, an alkane such as methane, ethane, a propane, a butane or a pentane, a cycloalkane such as cyclopropane, cyclobutane or cyclopentene, an alkene such as ethylene, propene, propadiene or a butene, or an alkyne such as acetylene or propyne and/or mixtures thereof. However, fluorinated gases are preferred. Fluorinated gases include materials which contain at least one fluorine atom such as $SF_6$, freons (organic compounds containing one or more carbon atoms and fluorine, i.e. $CF_4$, $C_2F_6$, $C_3F_8$, $C_4F_8$, $C_4F_{10}$, $CBrF_3$, $CCl_2F_2$, $C_2ClF_5$, and $CBrClF_2$) and perfluorocarbons. The term perfluorocarbon refers to compounds containing only carbon and fluorine atoms and includes, in particular, saturated, unsaturated, and cyclic perfluorocarbons. The saturated perfluorocarbons, which are usually preferred, have the formula $C_nF_{n+2}$, where n is from 1 to 12, preferably from 2 to 10, most preferably from 3 to 8 and even more preferably from 3 to 6. Suitable perfluorocarbons include, for example, $CF_4$, $C_2F_6$, $C_3F_8$, $C_4F_8$, $C_4F_{10}$, $C_5F_{12}$, $C_6F_{12}$, $C_7F_{14}$, $C_8F_{18}$, and $C_9F_{20}$. Most preferably the gas or gas mixture comprises $SF_6$ or a perfluorocarbon selected from the group consisting of $C_3F_8$ $C_4F_8$, $C_4F_{10}$, $C_5F_{12}$, $C_6F_{12}$, $C_7F_{14}$, $C_8F_{18}$, with $C_4F_{10}$ being particularly preferred. See also WO 97/29783, WO 98/53857, WO 98/18498, WO 98/18495, WO 98/18496, WO098/18497, WO 98/18501, WO 98/05364, and WO 98/17324.

In certain circumstances it may be desirable to include a precursor to a gaseous substance (e.g. a material that is capable of being converted to a gas in vivo, often referred to as a "gas precursor"). Preferably the gas precursor and the gas it produces are physiologically acceptable. The gas precursor may be pH-activated, photo-activated, temperature activated, etc. For example, certain perfluorocarbons may be used as temperature activated gas precursors. These perfluorocarbons, such as perfluoropentane, have a liquid/gas phase transition temperature above room temperature (or the temperature at which the agents are produced and/or stored) but below body temperature; thus, they undergo a phase shift and are converted to a gas within the human body.

As discussed, the gas can include a mixture of gases. The following combinations are particularly preferred gas mixtures: a mixture of gases (A) and (B) in which, at least one of the gases (B), present in an amount of between 0.5-41% by vol., has a molecular weight greater than 80 daltons and is a fluorinated gas and (A) is selected from the group consisting of air, oxygen, nitrogen, carbon dioxide and mixtures thereof, the balance of the mixture being gas A.

Since ultrasound vesicles may be larger than the other detectable labels described herein, they may be conjugated to a plurality of compound constructs in order to increase the targeting efficiency of the agent. Attachment to the ultrasound contrast agents described above (or known to those skilled in the art) may be via a covalent bond between a linkler of the invention and the material used to make the vesicle or via a linker, as described previously.

A number of methods may be used to prepare suspensions of microbubbles conjugated to compounds. For example, one may prepare maleimide-derivatized microbubbles by incorporating 5% (w/w) of N-MPB-PE (1,2-dipalmitoyl-sn-glycero-3-phosphoethanolamine-4-(p-maleimido-phenyl butyramide), (Avanti Polar-Lipids, Inc) in the phospholipid formulation. Then, solutions of mercaptoacetylated compounds of the invention (10 mg/mL in DMF), which have been incubated in deacetylation solution (50 mM sodium phosphate, 25 mM EDTA, 0.5 M hydroxylamine HCl, pH 7.5) are added to the maleimide-activated microbubble suspension. After incubation in the dark, under gentle agitation, the compound conjugated microbubbles may be purified by centrifugation.

Compounds that can be used for derivatization of microbubbles typically include the following components: (a) a hydrophobic portion, compatible with the material forming the envelope of the microbubble or of the microballoon, in order to allow an effective incorporation of the compound in the envelope of the vesicle; said portion is represented typically by a lipid moiety (dipalmitin, distearoyl); and (b) a spacer (typically PEGs of different molecular weights), which may be optional in some cases (microbubbles may for instance present difficulties to be freeze dried if the spacer is too long e.g) or preferred in some others (e.g. peptides may be less active when conjugated to a microballoon with short spacers); and (c) a reactive group capable of reacting with a corresponding reacting moiety on the peptide to be conjugated (e.g. maleimido with the —SH group of cysteine).

Alternatively, compounds conjugated to microbubbles may be prepared using biotin/avidin. For example, avidin-conjugated microbubbles may be prepared using a maleimide-activated phospholipid microbubble suspension, prepared as described above, which is added to mercaptoacetylated-avidin (which has been incubated with deacetylation solution). Biotinylated compounds of the invention are then added to the suspension of avidin-conjugated microbubbles, yielding a suspension of microbubbles conjugated to the compounds.

Unless it contains a hyperpolarized gas, known to require special storage conditions, the lyophilized residue may be stored and transported without need of temperature control of its environment and in particular it may be supplied to hospitals and physicians for on site formulation into a ready-to-use administrable suspension without requiring such users to have special storage facilities. Preferably in such a case it can be supplied in the form of a two-component kit which can include two separate containers or a dual-chamber container. In the former case preferably the container is a conventional septum-sealed vial, wherein the vial containing the lyophilized residue of step b) is sealed with a septum through which the carrier liquid may be injected using an optionally prefilled syringe. In such a case the syringe used as the container of the second component is also used then for injecting the contrast agent. In the latter case, preferably the dual-chamber container is a dual-chamber syringe and once the lyophilizate has been reconstituted and then suitably mixed or gently shaken, the container can be used directly for injecting the contrast agent. In both cases means for directing or permitting application of sufficient bubble forming energy into the contents of the container are provided. However, as noted above, in the stabilised contrast agents according to the invention the size of the gas microbubbles is substantially independent of the amount of agitation energy applied to the reconstituted dried product. Accordingly, no more than gentle hand shaking is generally required to give reproducible products with consistent microbubble size.

It can be appreciated by one of ordinary skill in the art that other two-chamber reconstitution systems capable of combining the dried powder with the aqueous solution in a sterile manner are also within the scope of the present invention. In such systems, it is particularly advantageous if the aqueous phase can be interposed between the water-insoluble gas and the environment, to increase shelf life of the product. Where a material necessary for forming the contrast agent is not already present in the container (e.g. a targeting ligand to be linked to the phospholipid during reconstitution), it can be packaged with the other components of the kit, preferably in a form or container adapted to facilitate ready combination with the other components of the kit.

No specific containers, vial or connection systems are required; the present invention may use conventional containers, vials and adapters. The only requirement is a good seal between the stopper and the container. The quality of the seal, therefore, becomes a matter of primary concern; any degradation of seal integrity could allow undesirable substances to enter the vial. In addition to assuring sterility, vacuum retention is essential for products stoppered at ambient or reduced pressures to assure safe and proper reconstitution. As to the stopper, it may be a compound or multicomponent formulation based on an elastomer, such as poly(isobutylene) or butyl rubber.

Ultrasound imaging techniques which may be used in accordance with the present invention include known techniques, such as color Doppler, power Doppler, Doppler amplitude, stimulated acoustic imaging, and two- or three-dimensional imaging techniques. Imaging may be done in harmonic (resonant frequency) or fundamental modes, with the second harmonic preferred.

In ultrasound applications the contrast agents formed by phospholipid stabilized microbubbles may, for example, be administered in doses such that the amount of phospholipid injected is in the range 0.1 to 200 µg/kg body weight, preferably from about 0.1 to 30 µg/kg. Microballoon-containing contrast agents are typically administered in doses such that the amount of wall-forming polymer or lipid is from about 10 µg/kg to about 20 mg/kg of body weight.

In a preferred embodiment, the ultrasound contrast agents described herein are conjugated to one or more compounds comprised of compounds of the invention (e.g., linkers of the invention) and targeting peptides, or other diagnostic moieties or therapeutic moieties. The targeted ultrasound contrast agents will localize at sites of tissue expressing the target and may be used to image and/or treat such tissue.

7E. Radiotherapy

Radioisotope therapy involves the administration of a radiolabeled compound in sufficient quantity to damage or destroy the targeted tissue. After administration of the compound (by e.g. intravenous, subcutaneous, or intraperitonal injection), the radiolabeled pharmaceutical localizes preferentially at the disease site (in this instance, tumor or other tissue that expresses the target). Once localized, the radiolabeled compound then damages or destroys the diseased tissue with the energy that is released during the radioactive decay of the isotope that is administered.

The design of a successful radiotherapeutic involves several critical factors:

1. selection of an appropriate targeting group to deliver the radioactivity to the disease site;
2. selection of an appropriate radionuclide that releases sufficient energy to damage that disease site, without substantially damaging adjacent normal tissues; and
3. selection of an appropriate combination of the targeting group and the radionuclide without adversely affecting the ability of this conjugate to localize at the disease site. For radiometals, this often involves a chelating group that coordinates tightly to the radionuclide, combined with a linker that couples said chelate to the targeting group, and that affects the overall biodistribution of the compound to maximize uptake in target tissues and minimizes uptake in normal, non-target organs.

The present invention provides radiotherapeutic agents that satisfy all three of the above criteria, through proper selection of targeting group, radionuclide, metal chelate and linker.

Radiotherapeutic agents may contain a chelated 3+metal ion from the class of elements known as the lanthanides (elements of atomic number 57-71) and their analogs (i.e. $M^{3+}$ metals such as yttrium and indium). Typical radioactive metals in this class include the isotopes 90-Yttrium, 111-Indium, 149-Promethium, 153-Samarium, 166-Dysprosium, 166-Holmium, 175-Ytterbium, and 177-Lutetium. All of these metals (and others in the lanthanide series) have very similar chemistries, in that they remain in the +3 oxidation state, and prefer to chelate to ligands that bear hard (oxygen/nitrogen) donor atoms, as typified by derivatives of the well known chelate DTPA (diethylenetriaminepentaacetic acid) and polyaza-polycarboxylate macrocycles such as DOTA (1,4,7,10-tetraazacyclododecane-N,N',N'',N'''-tetraacetic acid and its close analogs. The structures of these chelating ligands, in their fully deprotonated form are shown below.

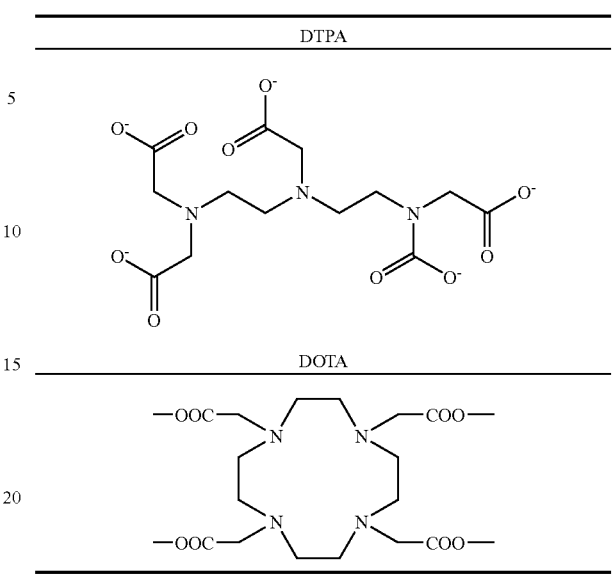

These chelating ligands encapsulate the radiometal by binding to it via multiple nitrogen and oxygen atoms, thus preventing the release of free (unbound) radiometal into the body. This is important, as in vivo dissociation of 3+ radiometals from their chelate can result in uptake of the radiometal in the liver, bone and spleen [Brechbiel M W, Gansow O A, "Backbone-substituted DTPA ligands for $^{90}$Y radioimmunotherapy", Bioconj. Chem. 1991; 2: 187-194; Li, WP, Ma D S, Higginbotham C, Hoffman T, Ketring A R, Cutler C S, Jurisson, S S, "Development of an in vitro model for assessing the in vivo stability of lanthanide chelates." Nucl. Med. Biol. 2001; 28(2): 145-154; Kasokat T, Urich K. Arzneim.-Forsch, "Quantification of dechelation of gadopentetate dimeglumine in rats". 1992; 42(6): 869-76]. Unless one is specifically targeting these organs, such non-specific uptake is highly undesirable, as it leads to non-specific irradiation of non-target tissues, which can lead to such problems as hematopoietic suppression due to irradiation of bone marrow.

For radiotherapy applications, any of the chelators for therapeutic radionuclides disclosed herein may be used. However, forms of the DOTA chelate [Tweedle M F, Gaughan G T, Hagan J T, "1-Substituted-1,4,7-triscarboxymethyl-1,4,7,10-tetraazacyclododecane and analogs." U.S. Pat. No. 4,885,363, Dec. 5, 1989] are particularly preferred, as the DOTA chelate is expected to de-chelate less in the body than DTPA or other linear chelates.

General methods for coupling DOTA-type macrocycles to targeting groups through a linker (e.g. by activation of one of the carboxylates of the DOTA to form an active ester, which is then reacted with an amino group on the linker to form a stable amide bond), are known to those skilled in the art. (See e.g. Tweedle et al. U.S. Pat. No. 4,885,363). Coupling can also be performed on DOTA-type macrocycles that are modified on the backbone of the polyaza ring.

The selection of a proper nuclide for use in a particular radiotherapeutic application depends on many factors, including:

a. Physical half-life—This should be long enough to allow synthesis and purification of the radiotherapeutic construct from radiometal and conjugate, and delivery of said construct to the site of injection, without significant radioactive decay prior to injection. Preferably, the radionuclide should have a physical half-life between about 0.5 and 8 days.

b. Energy of the emission(s) from the radionuclide—Radionuclides that are particle emitters (such as alpha emitters, beta emitters and Auger electron emitters) are particularly useful, as they emit highly energetic particles that deposit their energy over short distances, thereby producing highly localized damage. Beta emitting radionuclides are particularly preferred, as the energy from beta particle emissions from these isotopes is deposited within 5 to about 150 cell diameters. Radiotherapeutic agents prepared from these nuclides are capable of killing diseased cells that are relatively close to their site of localization, but cannot travel long distances to damage adjacent normal tissue such as bone marrow.

c. Specific activity (i.e. radioactivity per mass of the radionuclide)—Radionuclides that have high specific activity (e.g. generator produced 90-Y, 111-In, 177-Lu) are particularly preferred. The specific activity of a radionuclide is determined by its method of production, the particular target that is used to produce it, and the properties of the isotope in question.

Many of the lanthanides and lanthanoids include radioisotopes that have nuclear properties that make them suitable for use as radiotherapeutic agents, as they emit beta particles. Some of these are listed in the table below.

| Isotope | Half-Life (days) | Max b-energy (MeV) | Gamma energy (keV) | Approximate range of b-particle (cell diameters) |
|---|---|---|---|---|
| $^{149}$-Pm | 2.21 | 1.1 | 286 | 60 |
| $^{153}$-Sm | 1.93 | 0.69 | 103 | 30 |
| $^{166}$-Dy | 3.40 | 0.40 | 82.5 | 15 |
| $^{166}$-Ho | 1.12 | 1.8 | 80.6 | 117 |
| $^{175}$-Yb | 4.19 | 0.47 | 396 | 17 |
| $^{177}$-Lu | 6.71 | 0.50 | 208 | 20 |
| $^{90}$-Y | 2.67 | 2.28 | — | 150 |
| $^{111}$-In | 2.810 | Auger electron emitter | 173, 247 | <5μm |

Pm: Promethium,
Sm: Samarium,
Dy: Dysprosium,
Ho: Holmium,
Yb: Ytterbium,
Lu: Lutetium,
Y: Yttrium, In: Indium Methods for the preparation of radiometals such as beta-emitting lanthanide radioisotopes are known to those skilled in the art, and have been described elsewhere [e.g., Cutler C S, Smith C J, Ehrhardt G J.; Tyler T T, Jurisson S S, Deutsch E. "Current and potential therapeutic uses of lanthanide radioisotopes." Cancer Biother. Radiopharm. 2000; 15(6): 531-545]. Many of these isotopes can be produced in high yield for relatively low cost, and many (e.g. $^{90}$-Y, $^{149}$-Pm, $^{177}$-Lu) can be produced at close to carrier-free specific activities (i.e. the vast majority of atoms are radioactive). Since non-radioactive atoms can compete with their radioactive analogs for binding to receptors on the target tissue, the use of high specific activity radioisotope is important, to allow delivery of as high a dose of radioactivity to the target tissue as possible.

Radiotherapeutic derivatives of the invention containing beta-emitting isotopes of rhenium ($^{186}$-Re and $^{188}$-Re) are also particularly preferred.

8. Dosages And Additives

Proper dose schedules for the compounds of the present invention are known to those skilled in the art. The compounds can be administered using many methods which include, but are not limited to, a single or multiple IV or IP injections. For radiopharmaceuticals of the invention, one administers a quantity of radioactivity that is sufficient to permit imaging, or in the case of radiotherapy, to cause damage or ablation of the targeted GRP-R bearing tissue, but not so much that substantive damage is caused to non-target (normal tissue). The quantity and dose required for scintigraphic imaging is discussed supra. The quantity and dose required for radiotherapy is also different for different constructs, depending on the energy and half-life of the isotope used, the degree of uptake and clearance of the agent from the body and the mass of the tumor. In general, doses can range from a single dose of about 30-50 mCi to a cumulative dose of up to about 3 Curies.

The optical imaging compounds of the present invention can be administered to a patient alone or as part of a composition that contains other components such as excipients, diluents, radical scavengers, stabilizers, and carriers, all of which are well-known in the art. The optical imaging compounds can be administered to patients either intravenously or intraperitoneally. The amount of compound administered will typically be in the range of approximately 0.01 mg/kg to 10.0 mg/kg of body weight of the patient.

In ultrasound applications the contrast agents formed by phospholipid stabilized microbubbles may, for example, be administered in doses such that the amount of phospholipid injected is in the range 0.1 to 200 μg/kg body weight, preferably from about 0.1 to 30 μg/kg. Microballoon-containing contrast agents are typically administered in doses such that the amount of wall-forming polymer or lipid is from about 10 μg/kg to about 20 mg/kg of body weight.

For MRI, it is contemplated that the subject will receive a dosage of contrast agent sufficient to enhance the MR signal at the target at least 10%. After injection of the compound including the MRI reagent, the patient is scanned in the MRI machine to determine the location of any sites containing the target. In therapeutic settings, upon target localization, a cytotoxic or therapeutic agent can be immediately administered, if necessary, and the patient can be subsequently scanned to visualize the therapeutic effect.

The pharmaceutical compositions of the invention can include physiologically acceptable buffers, and typical additives, excipients, etc. In the case of radiopharmaceuticals, compositions of the invention can require radiation stabilizers to prevent radiolytic damage to the compound prior to injection. Radiation stabilizers are known to those skilled in the art, and may include, for example, para-aminobenzoic acid, ascorbic acid, gentistic acid and the like. Particularly preferred stabilizers and formulations are discussed in copending provisional application U.S. Ser. No. 60/489,850.

A single or multi-vial kit that contains all of the components needed to prepare the diagnostic or therapeutic agents of this invention is an integral part of this invention. In the case of radiopharmaceuticals of the invention, such kits will generally include all of the components needed to prepare the radiopharmaceutical except the radionuclide.

For example, a single-vial kit for preparing a radiopharmaceutical of the invention preferably contains a chelator/linker/targeting peptide conjugate of the formula M-N-O-P-Q, a source of stannous salt (if reduction is required, e.g., when using technetium), or other pharmaceutically acceptable reducing agent, and is appropriately buffered with pharmaceutically acceptable acid or base to adjust the pH to a value of about 3 to about 9. The quantity and type of reducing agent used will depend highly on the nature of the exchange complex to be formed. The proper conditions are well known to those that are skilled in the art. It is preferred that the kit contents be in lyophilized form. Such a single vial kit may optionally contain labile or exchange ligands such as glucoheptonate, gluconate, mannitol, malate, citric or tartaric acid and can also contain reaction modifiers: such as diethylenetriamine-pentaacetic acid (DPTA), ethylenediamine tetraacetic acid (EDTA), or α, β, or γ-cyclodextrin that serve to improve the radiochemical purity and stability of the final product. The kit may also contain stabilizers, bulking agents such as mannitol, that are designed to aid in the freeze-drying process, and other additives known to those skilled in the art.

A multi-vial kit preferably contains the same general components but employs more than one vial in reconstituting the radiopharmaceutical. For example, one vial may contain all of the ingredients that are required to form a labile Tc(V) complex on addition of pertechnetate (e.g. the stannous source or other reducing agent). Pertechnetate is added to this vial, and after waiting an appropriate period of time, the contents of this vial are added to a second vial that contains the chelator and targeting peptide, as well as buffers' appropriate to adjust the pH to its optimal value. After a reaction time of about 5 to 60 minutes, the complexes of the present invention are formed. It is advantageous that the contents of both vials of this multi-vial kit be lyophilized. As above, reaction modifiers, exchange ligands, stabilizers, bulking agents, etc. may be present in either or both vials.

General Preparation of Compounds

The compounds of the present invention can be prepared by various methods depending upon the selected diagnostic or therapeutic moiety. The peptide portion of the compound can be most conveniently prepared by techniques generally established and known in the art of peptide synthesis, such as the solid-phase peptide synthesis (SPPS) approach. Because it is amenable to solid phase synthesis, employing alternating FMOC protection and deprotection is the preferred method of making short peptides. Recombinant DNA technology is preferred for producing proteins and long fragments thereof.

Solid-phase peptide synthesis (SPPS) involves the stepwise addition of amino acid residues to a growing peptide chain that is linked to an insoluble support or matrix, such as polystyrene. The C-terminal residue of the peptide is first anchored to a commercially available support with its amino group protected with an N-protecting agent such as a t-butyloxycarbonyl group (Boc) or a fluorenylmethoxycarbonyl (Fmoc) group. The amino protecting group is removed with suitable deprotecting agents such as TPA in the case of Boc or piperidine for Fmoc and the next amino acid residue (in N-protected form) is added with a coupling agent such as dicyclocarbodiimide (DCC). Upon formation of a peptide bond, the reagents are washed from the support. After addition of the final residue, the peptide is cleaved from the support with a suitable reagent such as trifluoroacetic acid (TFA) or hydrogen fluoride (HF).

EXAMPLES

The following examples are provided as examples of different methods which can be used to prepare various compounds of the present invention. Within each example, there are compounds identified in single bold capital letter (e.g., A, B, C), which correlate to the same labeled corresponding compounds in the drawings identified. Examples I to VII are prophetic.

General Experimental Description

A. Definitions of Abbreviations Used
The following common abbreviations are used throughout this specification:
1,1-dimethylethoxycarbonyl (Boc or Boc);
9-fluorenylmethyloxycarbonyl (Fmoc);
1-hydroxybenozotriazole (HOBT);
N,N'-diisopropylcarbodiimide (DIC);
N-methylpyrrolidinone (NNT);
acetic anhydride ($Ac_2O$);
(4,4-dimethyl-2,6-dioxocyclohex-1-ylidene)-3-methylbutyl (iv-Dde);
trifluoroacetic acid (TFA);
Reagent B (TFA:$H_2O$:phenol:triisopropylsilane, 88:5:5:2);
diisopropylethylamine (DIEA);
O-(1H-benzotriazole-1-yl)-N,N,N',N'-tetramethyluronium hexafluorophosphate (HBTU);
O-(7-azabenzotriazol-1-yl)-1,1,3,3-tetramethyluronium hexafluorphosphate (TU);
N-hydroxysuccinimide (NHS);
solid phase peptide synthesis (SPPS);
dimethylsulfoxide (DMSO);
dichloromethane (DCM);
dimethylformamide (DMF);
dimethylacetamide (DMA);
isobutylchloroformate (IBCF)
1,4,7,10-tetraazacyclotetradecane-1,4,7,10-tetraacetic acid (DOTA);
Triisopropylsilane (TIPS);
1,4,7,10-tetraazacyclotetradecane-1,4,7,10-tetraacetic acid (DOTA)
(1R)-1-[1,4,7,10-tetraaza-4,7, 10-tris(carboxymethyl)cyclododecyl] ethane-1,2-dicarboxylic acid (CMDOTA);
fetal bovine serum (FBS);
human serum albumin (HSA);
human prostate cancer cell line (PC3);
radiochemical purity (RCP);
high performance liquid chromatography (HPLC), and
magnetic resonance imaging (MRI).

B. Materials
The Fmoc-protected amino acids used were purchased from Nova-Biochem (San Diego, Calif., USA), Advanced Chem Tech (Louisville, Ky., USA), Chem-Impex International (Wood Dale Ill., USA), and Multiple Peptide Systems (San Diego, Calif., USA). Other chemicals, reagents and adsorbents required for the syntheses were procured from Aldrich Chemical Co. (Milwaukee, Wis., USA) and VWR Scientific Products (Bridgeport, N.J., USA). Solvents for peptide synthesis were obtained from Pharmco Co. (Brookfield Conn., USA). Columns for HPLC analysis and purification were obtained from Waters Co. (Milford, Mass., USA). Experimental details are given below for those that were not commercially available.

C. Instrumentation for Peptide Synthesis
Peptides were prepared using an Advanced ChemTech 496Ω MOS synthesizer, an Advanced ChemTech 357 FBS synthesizer and/or by manual peptide synthesis. However the protocols for iterative deprotection and chain extension employed were the same for all.

D. Instrumentation Employed for Analysis and Purification
Analytical HPLC was performed using a Shimadzu-LC-10A dual pump gradient analytical LC system employing Shimadzu-ClassVP software version 4.1 for system control, data acquisition, and post run processing. Mass spectra were acquired on a Hewlett-Packard Series 1100 MSD mass spectrometer interfaced with a Hewlett-Packard Series 1100 dual pump gradient HPLC system fitted with an Agilent Technologies 1100 series autosampler fitted for either direct flow injection or injection onto a Waters Associates XMerra MS C18 column (4.6 mm×50 mm, 5 μ particle, 120Å pore). The instrument was driven by a HP Kayak workstation using 'MSD Anyone' software for sample submission and HP Chemstation software for instrument control and data acquisition. In most-cases the samples were introduced via direct injection using a 5 μL injection of sample solution at a concentration of 1 mg/mL and analyzed using positive ion electrospray to obtain m/e and m/z (multiply charged) ions for confirmation of structure. $^1$H-NMR spectra were obtained on a Varian Innova spectrometer at 500 MHz. $^{13}$C-NMR spectra were obtained on the same instrument at 125.73 MHz. Generally the residual $^1$H absorption, or in the case of $^{13}$C-NMR, the $^{13}$C absorption of the solvent employed, was used as an internal reference; in other cases tetramethylsilane (δ=0.00 ppm) was employed. Resonance values are given in δ units. Microanalysis data was obtained from Quantitative Technologies Inc. Whitehouse N.J. Preparative HPLC was performed on a Shimadzu-LC-8A dual pump gradient preparative HPLC system employing Shimadzu-ClassVP software version 4.3 for system control, data acquisition, fraction collection and post run processing E. Solid Support for Peptide Synthesis:

Rink Amide-Novagel HL resin (0.6 mmol/g) was used as the solid support.

F. Coupling Procedure:

In a typical experiment, the first amino acid was loaded onto 0.1 g of the resin (0.06 mmol). The appropriate Fmoc-amino acid in NMo (0.25M solution; 0.960 mL was added to the resin followed by N-hydroxybenzotriazole (0.5M in NMP; 0.48 mL)) and the reaction block (in the case of automated peptide synthesis) or individual reaction vessel (in the case of manual peptide synthesis) was shaken for about 2 min. To the above mixture, diisopropylcarbodiimide (0.5M in NMP; 0.48 mL) was added and the reaction mixture was shaken for 4 h at ambient temperature. Then the reaction block or the individual reaction vessel was purged of reactants by application of a positive pressure of dry nitrogen.

G. Washing Procedure:

Each well of the reaction block was filled with 1.2 mL of NMP and the block was shaken for 5 min. The solution was drained under positive pressure of nitrogen. This procedure was repeated three times. The same procedure was used, with an appropriate volume of NMP, in the case of manual synthesis using individual vessels.

H. Removal of Fmoc Group:

The resin containing the Fmoc-protected amino acid was treated with 1.5 mL of 20% piperidine in DMF (v/v) and the reaction block or individual manual synthesis vessel was shaken for 15 min. The solution was drained from the resin. This procedure was repeated once and the resin was washed employing the washing procedure described above.

I. Final Coupling of Ligand (DOTA and CMDOTA):

The N-terminal amino group of the resin bound peptide linker construct was deblocked and the resin was washed. A 0.25M solution of the desired ligand and HBTU in NMP was made, and was treated with a two-fold equivalency of DIEA. The resulting solution of activated ligand was added to the resin (1.972 mL; 0.48 mmol) and the reaction mixture was shaken at ambient temperature for 24-30 h. The solution was drained and the resin was washed. The final wash of the resin was conducted with 1.5 mL dichloromethane (3×).

J. Deprotection and Purification of the Final Peptide:

A solution of reagent B (2 mL; 88:5:5:2-TFA:Phenol:Water:TIPS) was added to the resin and the reaction block or individual vessel was shaken for 4.5 h at ambient temperature. The resulting solution containing the deprotected peptide was drained into a vial. This procedure was repeated two more times with 1 mL of reagent B. The combined filtrate was concentrated under reduced pressure using a Genevac HT-12 series II centrifugal concentrator. The residue in each vial was then triturated with 2 mL of Et$_2$O and the supernatant was decanted. This procedure was repeated twice to provide the peptides as colorless solids. The crude peptides were dissolved in water/acetonitrile and purified using either a Waters XTerra MS C18 column (50 mm×19 mm, 5 micron particle size, 120Å pore size) or a Waters-YMC C18 ODS column (250 mm×30 mm i.d., 10 micron particle size. 120 Å pore size). The fractions with the products were collected and analyzed by HPLC. The fractions with >95% purity were pooled and the peptides isolated by lyophilization.

Conditions for Preparative HPLC (Waters XTerra Column):

Elution rate: 50 mL/min

Detection: UV, λ=220 nm

Eluent A: 0.1% aq. TFA; Solvent B: Acetonitrile (0.1% TFA).

Conditions for HPLC Analysis:

Column: Waters XTerra (Waters Co.; 4.6×50 mm; MS C18; 5 micron particle, 120 Å pore).

Elution rate: 3 mL/min; Detection: UV, λ=220 nm.

Eluent A:0.1% aq. TFA; Solvent B: Acetonitrile (0.1% TFA).

Example I

FIG. 1

Synthesis of 4-[[(3β,5β,12α)-23-[1,1-dimethylethane-1-(oxycarbonyl)]-12-hydroxy-24-norcholan-3-yl]amino]-4-oxobutanoic acid N-hydroxysuccinimidyl ester (Compound A-OSu)

Deoxycholic acid is converted into the corresponding t-butyl ester 1 according to the procedure for the esterification of cholic acid reported by R. P. Bonar-Law et al. (*J. Chem. Soc. Perkin Trans.* 1, 2245, 1990). Compound 1 is transformed into the 3-amino derivative 2 applying the one pot Mitsunobu-Staudinger procedure developed by P. L. Anelli et al. (Synth. Commun. 1998, 28, 109-117) to prepare methyl 3 β-aminodeoxycholate.

Amino ester 2 is reacted with an equimolar amount of succinic anhydride in THF in the presence of triethylamine. After acidic (aq HCl) work up the mixture is extracted with EtOAc. The organic phase is evaporated to dryness and the residue purified by flash chromatography to give derivative 3. Yield 55%.

Acid 3 is reacted with N-hydroxysuccinimide and dicyclohexylcarbodiimide in a mixture of THF and acetonitrile at room temperature. After precipitation of dicyclohexylurea the mixture is filtered and evaporated to afford crude compound A-OSu which is used in the following step without any further purification.

Example II

FIG. 2

Synthesis of Bovine $N^{\varepsilon B29}$-[4-[[(3β,5β,12α)-23-carboxy-12-hydroxy-24-norcholan-3-yl]amino]-4-oxobutanoyl]-insulin (Compound B)

$N^{\alpha A1}$,$N^{\alpha A2}$-dicitraconyl-insulin (bovine) is prepared according to Naithani V. K. & Gattner H.-G.: *Hoppe-Seyler's Z. Physiol. Chem.* 349, 373-384, 1968. To a solution of $N^{\alpha A1}$, $N^{\alpha A2}$-dicitraconyl-insulin (14 μmol) in 24 mL of dimethylformamide is added triethylamine (92.7 μmol) in 1.2 mL dimethylformamide. Compound A-OSu (79 mmol) in 1 mL dimethylformamide is added and the reaction mixture allowed to proceed for 30 min at room temperature. The reaction mixture is acidified with 1 M acetic acid and chromatographed on Sephadex G-25 (2×70 cm) in 1 M acetic acid. The protein peak fractions are pooled and lyophilized. Decitraconylation is achieved in formic acid pH 3.5 for 72 h, followed by renewed lyophilization. The material is fractionated by preparative isoelectric focusing in flat-bed gel-stabilized layers according to Radola: *Biochim. Biophys. Acta* 295, 412-428, 1973, except that Ultradex™ (Amersham Biosciences Inc.), as washed gel medium, is used. The gel is suspended in 5 M urea (purified over mixed bed resin) and carrier ampholytes (2%), pH 4 to 6, were added. The slurry (210 mL) is placed in a flat plate (Desaga/Brhikmann) (20×20 cm), the sample applied 2 cm from the cathode, and focusing is achieved at 25 to 30 V/cm for 18 to 24 h on a 1-4° C. cooling plate (Hormuth/Brinkmann). Visibile (refractive) bands are formed, and the pH in the bands is determined after dilution of a gel sample in water. The major band corresponds to a pH of 5.1, the expected pH for insulin with a selective modification of $Lys^{\epsilon B29}$ with compound A. The material from the major band is recovered from the gel by elution with three bed volumes of 1 M acetic acid. Urea is removed by chromatography on Sephadex G-25 (2.5×70 cm) in 1 M-acetic acid and protein fractions are lyophilized. The protein is dissolved in and loaded onto a chromatography column of DEAE-cellulose DE52 (0.9×25 cm) in 7 M urea, 0.01 M Tris/HCl, pH 8.3, at room temperature. The column is eluted with the same buffer forming a linear gradient of NaCl (0 to 0.15 M). Fractions of 6.1 mL are collected. The major peak is collected and desalted on a column of Sephadex G-25 (2.5×70 cm) in 1 M acetic acid and protein fractions are lyophilized. The t-butyl ester is cleaved by dissolution in trifluoroacetic acid. After evaporation of the trifluoroacetic acid, the protein (Compound B) is dissolved in 1 M acetic acid and lyophilized. Analytical polyacrylamide disc gel electrophoresis according to Davis B. J.: *Ann. N.Y. Acad. Sci.* 121, 404-427, 1964, demonstrates the homogeneity of the material. Ion-spray mass spectrometry shows the correct molecular weight for the expected Compound B. Compound B comprises a therapeutic moiety (an insulin molecule) attached to a cholic acid derivative linker of the invention.

Example III

Figure 1:
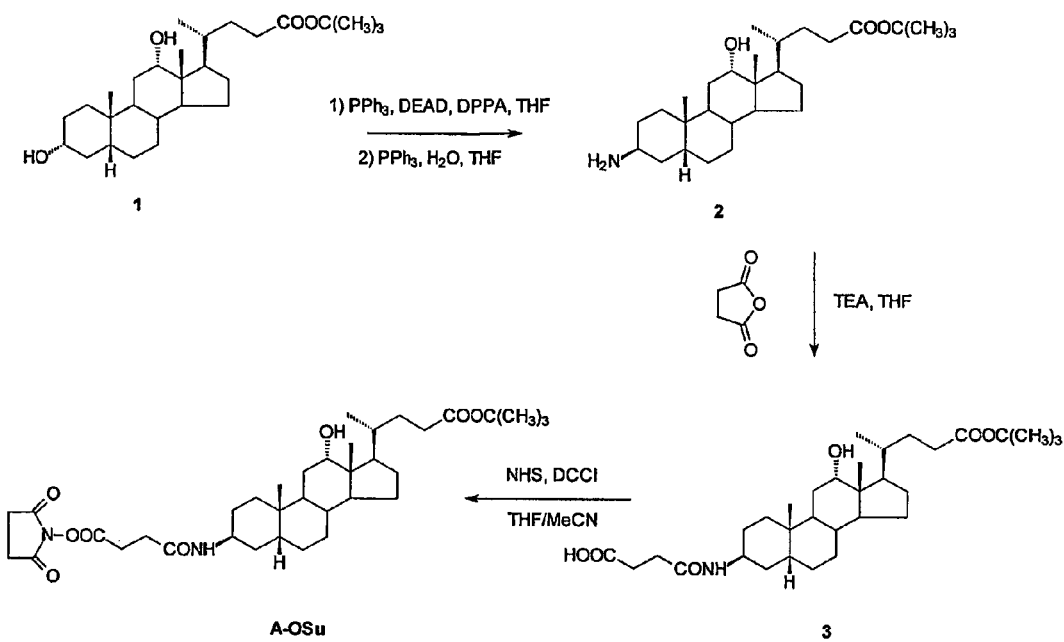
FIG. 1 is a graphical representation of the synthesis of 4-[[(3β,5β, 12α)-23-carboxy-12-hydroxy-24-norcholan-3-yl]amino]-4-oxobutanoic acid N-hydroxysuccinimidyl ester (Compound A-OSu) as described in Example I.
Figure 2:
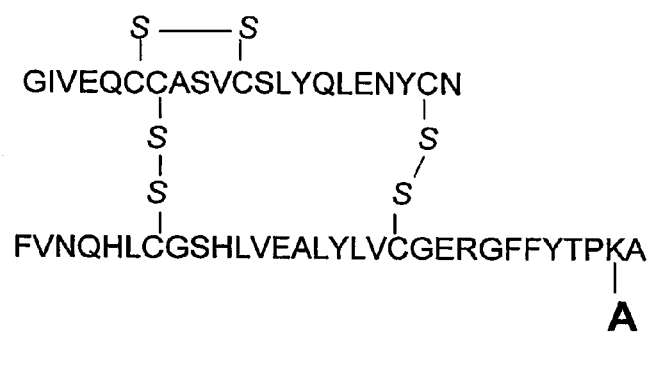
FIG. 2 is a chemical structure of Compound B as described in Example II.
Figure 3:
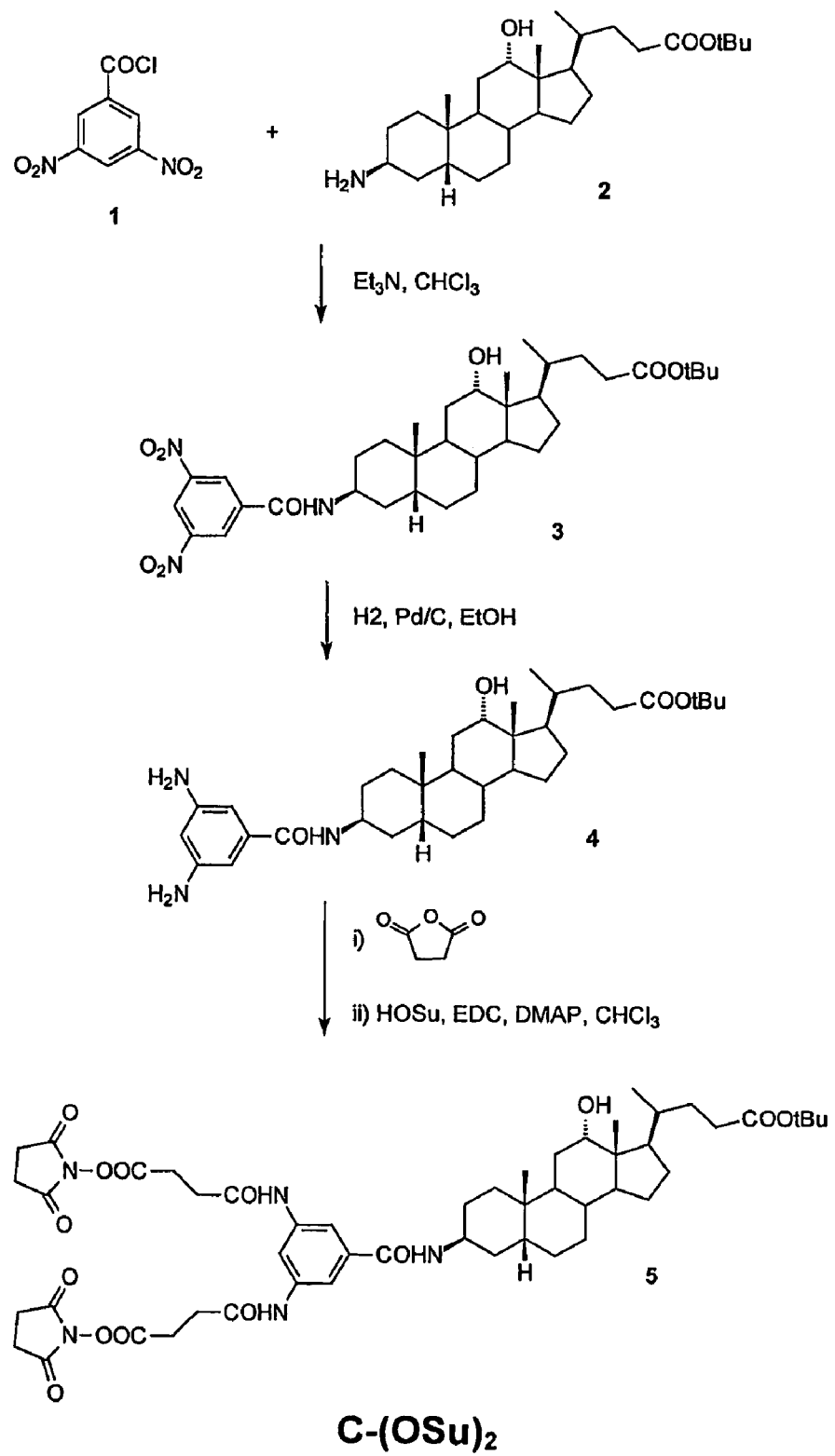
FIG. 3 is a graphical representation of a series of chemical reactions for the synthesis of (3β,5β,12α)-3-[[3,5-Bis[[4-[(2,5-dioxo-1-pyrrolidinyl)oxy]-1,4-dioxobutyl]amino]benzoyl]amino]-12-hydroxycholan-24-oic acid 1,1-dimethylethyl ester (Compound C—(OSu)$_2$), as described in Example III.

FIGS. 3 and 4

A. Syntheis of (3β,5β,12α)-3-[[3,5-Bis[[4-[(2,5-dioxo-1-pyrrolidinyl)oxy]-1,4-dioxobutyl]amino]benzoyl]amino]-12-hydroxycholan-24-oic acid 1,1-dimethylethyl ester (Compound C—(OSu)₂)

A solution of 3,5-dinitrobenzoyl chloride 1 (commercial product) in ethanol free chloroform is added dropwise to a solution of (3β,5β,12α)-3-amino-12-hydroxycholanoic acid t-butyl ester 2 in ethanol free chloroform and triethylamine. After completion of the reaction the mixture is washed with water, dried ($Na_2SO_4$), filtered and evaporated. The crude filtrate is purified by flash chromatography on silica gel to give pure compound 3 which is hydrogenated with palladium (10% on activated carbon) in ethanol to give compound 4. Compound 4 is dissolved in dichloromethane and reacted with two molar equivalents of succinic anhydride. The intermediate diacid is then reacted in ethanol free chloroform with N-hydroxysuccinimide (HOSu) in the presence of 1-[3-(dimethylamino)propyl]-3-ethylcarbodiimide hydrochloride (EDC) and 4-dimethylaminopyridine (DMAP). After completion of the reaction the mixture is washed with water, dried with $Na_2SO_4$, filtered and evaporated to give compound 5=C—(OSu)₂.

B. Synthesis of Bovine 1-[[(3β,5β,12α)-23-[(1,1-dimethyl)ethoxycarbonyl]-12-hydroxy-24-norcholan-3-yl]amino]carbonyl-3,5-bis[[4-(insulin-$N^{\epsilon B29}$-yl)-1,4-dioxobutyl]amino]benzene (Compound D) (FIG. 4)

$N^{\alpha A1, N \alpha A2}$-dicitraconyl-insulin (bovine) is prepared according to Naithani V. K. & Gattner H.-G.: *Hoppe-Seyler's Z Physiol. Chem.* 349, 373-384, 1968. To a solution of $N^{\alpha A1}$, $N^{\alpha A2}$-dicitraconyl-insulin (28 μmol) in 48 mL of dimethylformamide is added triethylamine (185 μmol) in 2.4 mL dimethylformamide. Compound C—(OSu)₂ (14 μmol) in 2 mL dimethylformamide is added and the reaction mixture is allowed to proceed for 30 min at room temperature. The reaction mixture is acidified with 1 M acetic acid and chromatographed on Sephadex G-25 (2×70 cm) in 1 M acetic acid. The protein peak fractions are pooled and lyophilized. Decitraconylation is achieved in formic acid pH 3.5 for 72 h, followed by renewed lyophilization. The t-butyl ester is cleaved by dissolution in trifluoroacetic acid. After evaporation of the trifluoroacetic acid, the protein is dissolved in 1 M acetic acid and fractionated by chromatography on Sephadex G-50 in 1 M acetic acid. The protein peak of the molecule with the largest size is collected and lyophilized. The material is once more fractionated on the same column. The fractionated protein is lyophilized. Ion-spray mass spectrometry shows the correct molecular weight for the expected Compound D. Compound D comprises a therapeutic moiety (an insulin molecule) attached to a linker of the invention, which is attached to another therapeutic moiety (an insulin molecule).

Example IV

Labeling of Compounds B and D with $^{125}I$

Labeling of Compounds B and D with $^{125}I$ is achieved by the method described in Lipkin E. W., Teller D. C. & de Haen C.: *J. Biol. Chem.* 261, 1694-1701, 1986 or as described herein.

Example V

Binding of Compounds B and D to Human Serum Albumin

Binding to human serum albumin is determined by ultrafiltration according to Whitlam J. B. & Brown K. F.: *J. Pharm. Sci.* 70, 146-150, 1981, applying 1 nM bovine insulin solution in 0.6 mM human serum albumin, spiked with $^{125}I$-labeled insulin. 95% of the insulin is bound. It is evident that such binding to albumin will reduce the renal elimination of the modified insulin (Compounds B and D) relative to that of native insulin.

Example VI

Biological Activity of Compounds B and D

It is known that $N^{\epsilon B29}$-biotinylinsulin bound to a 1:1 conjugate of avidin and ferritin with three of the four biotin binding sites occupied by biotin has the same dose-response curve as insulin for the activation of glucose oxidation in rat epididymal fat cells (May J. M., Williams R. H. & de Haën C.: *J. Biol. Chem.* 253, 686-690, 1978). Using the fat cell assay described therein, which involves incubation in buffers containing serum albumin, compounds B and D are also shown to have identical activity to native insulin. Combined with the reduced renal elimination, this property renders Compounds B and D forms of insulin with prolonged plasma half-life, providing improved pharmacokinetic properties compared to compounds which do not contain linkers of the invention.

Example VII

FIGS. 5A-B

Synthesis of $^{111}$In-Labeled Insulin Deoxycholic Acid Conjugate (Compound $^{111}$In—F)

A. Synthesis of Bovine 1-[[(3β,5β,12α)-23-[(1,1-dimethyl)ethoxycarbonyl]-12-hydroxy-24-norcholan-3-yl]amino]carbonyl-3-[[4-(insulin-N$^{εB29}$-yl)-1,4-dioxobutyl]amino]-5-[[[[2-[[[4,7,10-tris(carboxymethyl)-1,4,7,10-tetraazacyclododecyl]acetyl]amino]ethyl]amino]-1,4-dioxobutyl]amino]benzene. (Compound F)

N$^1$,N$^4$, N$^7$-triacetato-1,4,7,10-tetraazacyclododecan-N$^{10}$-2-acetamidoethylamine) (Compound E) (FIG. 5A) is synthesized according to Margerum, L.; Campion, B.; Fellmann, J. D.; Garrithy, M.; Varadarajan, J. PCT Int. Appl. WO9528967). N$^{α41}$,N$^{α42}$-dicitraconyl-insulin (bovine) is prepared according to Naithani V. K. & Gattner H.-G.: *Hoppe-Seyler's Z Physiol. Chem.* 349, 373-384, 1968. To a solution of N$^{α41}$,N$^{α42}$-dicitraconyl-insulin (28 µmol) in 48 mL of dimethylformamide is added triethylamine (185 µmol) in 2.4 mL dimethylformamide. Compound C—(OSu)$_2$ (see Example E) (140 µmol) in 2 mL of dimethylformamide is added and the reaction is allowed to proceed for 30 min. at room temperature. Then compound E (280 µmol) in 2 mL of dimethylformamide is added and the reaction is allowed to proceed for 30 min. at room temperature. The reaction mixture is acidified with 1 M acetic acid exhaustively dialyzed against 1 M acetic acid using a dialysis membrane with a nominal cut-off molecular weight of 1000. The retentate is lyophilized. Decitraconylation is achieved in formic acid pH 3.5 for 72 h, followed by renewed lyophilization. The t-butyl ester is cleaved by dissolution in trifluoroacetic acid. After evaporation of the trifluoroacetic acid, the protein is dissolved in 1 M acetic acid and fractionated by chromatography on Sephadex G-50 in 1 M acetic acid. The major protein peak is collected and lyophilized. Then the material is once more fractionated on the same column. The fractionated protein is lyophilized. Ion-spray mass spectrometry shows the correct molecular weight for the expected Compound F. (FIG. 5B). Compound F comprises a therapeutic moiety (an insulin molecule) attached to a cholic acid derivative linker, which is attached to a diagnostic moiety (a metal chelator).

B. Synthesis of $^{111}$In-labelled Compound F (Compound $^{111}$In—F)

To a 5-mL glass vial fitted with a 400 µL autosampler insert is added 100 µL of a 1 mg/mL solution of Compound F dissolved in a 9:1 mixture of 0.2 M NaOAc buffer (pH 4.8) and DMF. $^{111}$InCl$_3$ [1.5 mCi] in 0.05N HCl is added, the reaction vial is crimp-sealed, and the solution is heated at 45° C. for 30 minutes. After being cooled to room temperature, an aliquot of labeling mixture is purified by reversed phase UPLC on a Vydac C-18 Peptide and Protein column [4.6×250 mm; pore size: 5 micron; flow rate: 1.5 mL/min at 30° C.] using an aqueous/organic gradient of 0.1% trifluoroacetic acid in H$_2$O/0.085% trifluoroacetic acid in acetonitrile. The peak corresponding to $^{111}$In-labeled Compound F is collected into 0.5 mL of 50 mM citrate buffer, pH 5.7 containing 0.2% Human Serum Albumin, followed by removal of acetonitrile at reduced pressure using a Savant Speed Vacuum apparatus.

Example VIII

FIGS. 6A-B

Synthesis of L62

Figure 6A:
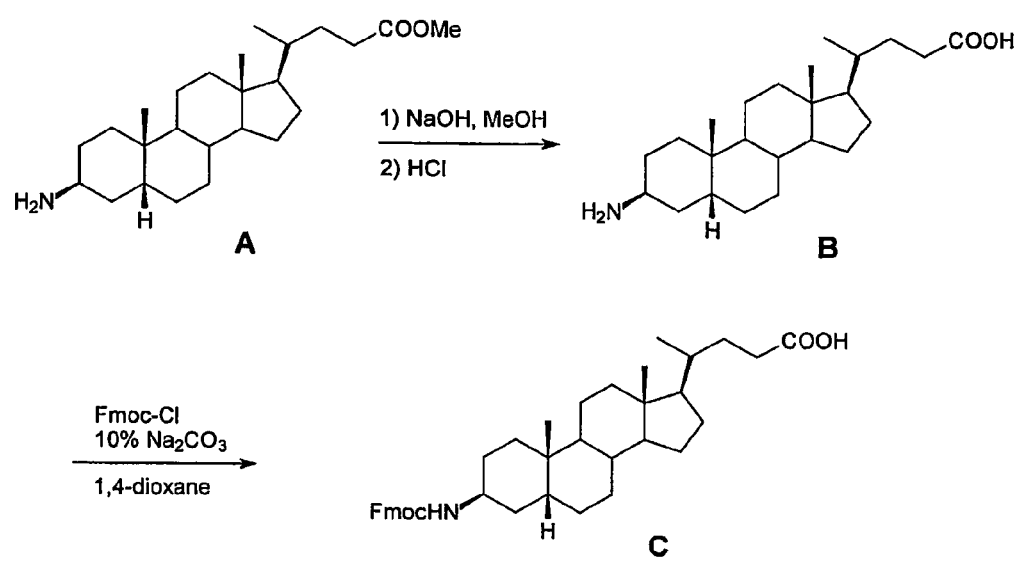
FIG. 6A is a graphical representation of a series of chemical reactions for the synthesis of intermediate C ((3β, 5β)-3-(9H-Fluoren-9-ylmethoxy)aminocholan-24-oic acid), from A (Methyl-(3β, 5β)-3-aminocholan-24-ate) and B ((3β, 5β)-3-aminocholan-24-oic acid), as described in Example VIII.
Figure 6B:
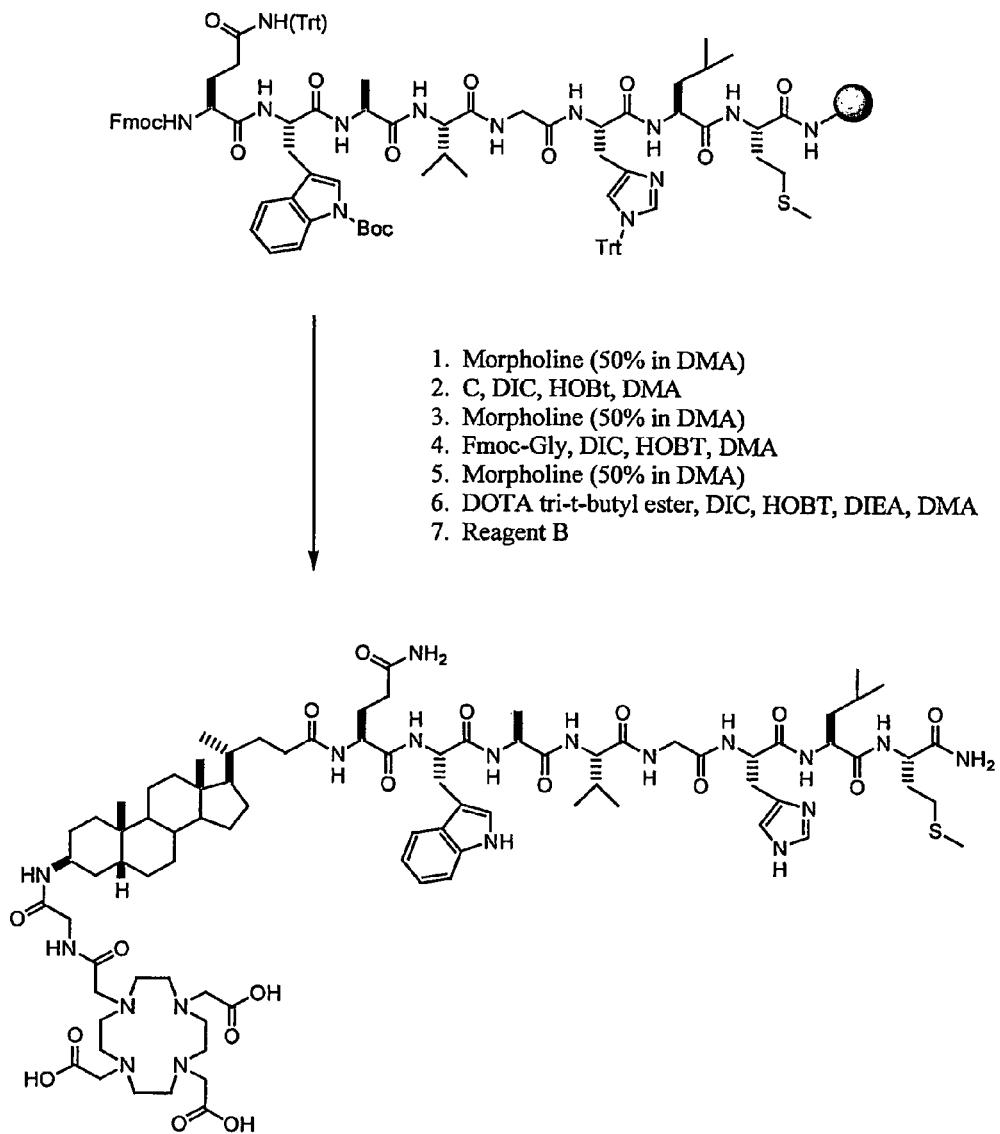
FIG. 6B is a graphical representation of the sequential reaction for the synthesis of N-[(3β,5β)-3-[[[[4,7,10-Tris (carboxymethyl)-1,4,7,10-tetraazacyclododec-1-yl]acetyl]amino]acetyl]amino]cholan-24-yl]-L-glutaminyl-L-tryptophyl-L-alanyl-L-valyl-glycyl-L-histidyl-L-leucyl-L-methioninamide (L62), as described in Example VIII.

Summary: As shown in FIGS. 6A-B, L62 was prepared using the following steps: Hydrolysis of (3β,5β)-3-aminocholan-24-oic acid methyl ester A with NaOH gave the corresponding acid B, which was then reacted with Fmoc-Cl to give intermediate C. Rink amide resin functionalised with the octapeptide Gln-Trp-Ala-Val-Gly-His-Leu-Met-NH$_2$ (BBN[7-14] [SEQ ID NO:1]) was sequentially reacted with C, Fmoc-glycine and DOTA tri-t-butyl ester. After cleavage and deprotection with reagent B the crude was purified by preparative HPLC to give L62. Overall yield: 2.5%. More details are provided below:

A. Rink Amide Resin Functionalised with Bombesin[7-14], (A)

In a solid phase peptide synthesis vessel (see enclosure No. 1) Fmoc-aminoacid (24 mmol), N-hydroxybenzotriazole (HOBt) (3.67 g; 24 mmol), and N,N'-diisopropylcarbodiimide (DIC) (3.75 mL; 24 mmol) were added sequentially to a suspension of Rink amide NovaGel™ resin (10 g; 6.0 mmol) A in DMF (45 mL). The mixture was shaken for 3 h at room temperature using a bench top shaker, then the solution was emptied and the resin was washed with DMF (5×45 mL). The resin was shaken with 25% piperidine in DMF (45 mL) for 4 min, the solution was emptied and fresh 25% piperidine in DMF (45 mL) was added. The suspension was shaken for 10 min, then the solution was emptied and the resin was washed with DMF (5×45 mL).

This procedure was applied sequentially for the following amino acids: N-α-Fmoc-L-methionine, N-α-Fmoc-L-leucine, N-α-Fmoc-N-im-trityl-L-histidine, N-α-Fmoc-glycine, N-α-Fmoc-L-valine, N-α-Fmoc-L-alanine, N-α-Fmoc-N-in-Boc-L-tryptophan.

In the last coupling reaction N-α-Fmoc-N-γ-trityl-L-glutamine (14.6 g; 24 mmol), HOBt (3.67 g; 24 mmol), and DIC (3.75 mL; 24 mmol) were added to the resin in DMF (45 mL). The mixture was shaken for 3 h at room temperature, the solution was emptied and the resin was washed with DMF (5×45 mL), CH$_2$Cl$_2$ (5×45 mL) and vacuum dried.

B. Preparation of Intermediates B and C:

1. Synthesis of (3β,5β)-3-Aminocholan-24-oic acid (B)

A 1 M solution of NaOH (16.6 mL; 16.6 mmol) was added dropwise to a solution of (3β,5β)-3-aminocholan-24-oic acid methyl ester (5.0 g; 12.8 mmol) in MeOH (65 mL) at 45° C. After 3 h stirring at 45° C., the mixture was concentrated to 25 mL and H$_2$O (40 mL) and 1 M HCl (22 mL) were added. The precipitated solid was filtered, washed with H₂O (2×50 mL) and vacuum dried to give B as a white solid (5.0 g; 13.3 mmol). Yield 80%.

2. Synthesis of (3β,5β)-3-(9H-Fluoren-9-ylmethoxy) aminocholan-24-oic Acid (C)

A solution of 9-fluorenylmethoxycarbonyl chloride (0.76 g; 2.93 mmol) in 1,4-dioxane (9 mL) was added dropwise to a suspension of (3β,5β)-3-aminocholan-24-oic acid B (1.0 g; 2.66 mmol) in 10% aq. $Na_2CO_3$ (16 mL) and 1,4-dioxane (9 mL) stirred at 0° C. After 6 h stirring at room temperature H₂O (90 mL) was added, the aqueous phase washed with Et₂O (2×90 mL) and then 2 M HCl (15 mL) was added (final pH: 1.5). The aqueous phase was extracted with EtOAc (2×100 mL), the organic phase dried over $Na_2SO_4$ and evaporated. The crude was purified by flash chromatography to give C as a white solid (1.2 g; 2.0 mmol). Yield 69%.

C. Synthesis of L62 (N-[(3β,5β)-3-[[[[[4,7,10-Tris (carboxymethyl)-1,4,7,10-tetraazacyclododec-1-yl] acetyl]amino] acetyl]amino]-cholan-24-yl]-L-glutaminyl-L-tryptophyl-L-alanyl-L-valyl-glycyl-L-histidyl-L-leucyl-L-methioninamide)

Resin A (0.5 g; 0.3 mmol) was shaken in a solid phase peptide synthesis vessel with 50% morpholine in DMA (7 mL) for 10 min, the solution was emptied and fresh 50% morpholine in DMA (7 mL) was added. The suspension was shaken for 20 min then the solution was emptied and the resin washed with DMA (5×7 mL). (3β,5β)-3-(9H-Fluoren-9-ylmethoxy)aminocholan-24-oic acid C (0.72 g; 1.2 mmol), N-hydroxybenzotriazole (HOBT) (0.18 g; 1.2 mmol), N,N'-diisopropylcarbodiimide (DIC) (0.19 mL; 1.2 mmol) and DMA (7 mL) were added to the resin, the mixture shaken for 24 h at room temperature, and the solution was emptied and the resin washed with DMA (5×7 mL). The resin was then shaken with 50% morpholine in DMA (7 mL) for 10 min, the solution was emptied, fresh 50% morpholine in DMA (7 mL) was added and the mixture shaken for another 20 min. The solution was emptied and the resin washed with DMA (5×7 mL). N-α-Fmoc-glycine (0.79 g; 1.2 mmol), HOBT (0.18 g; 1.2 mmol), DIC (0.19 mL: 1.2 mmol) and DMA (7 mL) were added to the resin. The mixture was shaken for 3 h at room temperature, the solution was emptied and the resin washed with DMA (5×7 mL). The resin was then shaken with 50% morpholine in DMA (7 mL) for 10 min, the solution was emptied, fresh 50% morpholine in DMA (7 mL) was added and the mixture shaken for another 20 min. The solution was emptied and the resin washed with DMA (5×7 mL) followed by addition of 1,4,7,10-Tetraazacyclododecane-1,4,7,10-tetraacetic acid tris(1,1-dimethylethyl) ester adduct with NaCl (0.79 g; 1.2 mmol), HOBT (0.18 g; 1.2 mmol), DIC (0.19 mL: 1.2 mmol), DIEA (0.40 mL; 2.4 mmol) and DMA (7 mL) to the resin. The mixture was shaken for 24 h at room temperature, the solution was emptied and the resin washed with DMA (5×7 mL), $CH_2Cl_2$ (5×7 mL) and vacuum dried. The resin was shaken in a flask with reagent B (25 mL) for 4.5 h. The resin was filtered and the solution was evaporated under reduced pressure to afford an oily crude that was triturated with Et₂O (20 mL). The precipitate was collected by centrifugation and washed with Et₂O (3×20 mL), then analysed by HPLC and purified by preparative HPLC. The fractions containing the product were lyophilised to give L62 (6.6 mg; 3.8×10⁻³ mmol) as a white solid. Yield 4.5%.

Example IX

FIGS. 7A-E

Synthesis of L67

Summary: Hydrolysis of (3β,5β)-3-amino-12-oxocholan-24-oic acid methyl ester A with NaOH gave the corresponding acid B, which was then reacted with Fmoc-Glycine to give intermediate C. Rink amide resin functionalised with the octapeptide Gln-Trp-Ala-Val-Gly-His-Leu-Met-NH₂ (BBN [7-14] [SEQ ID NO:1]) was sequentially reacted with C, and DOTA tri-t-butyl ester. After cleavage and deprotection with reagent B the crude was purified by preparative HPLC to give L67. Overall yield: 5.2%.

Figure 7A:
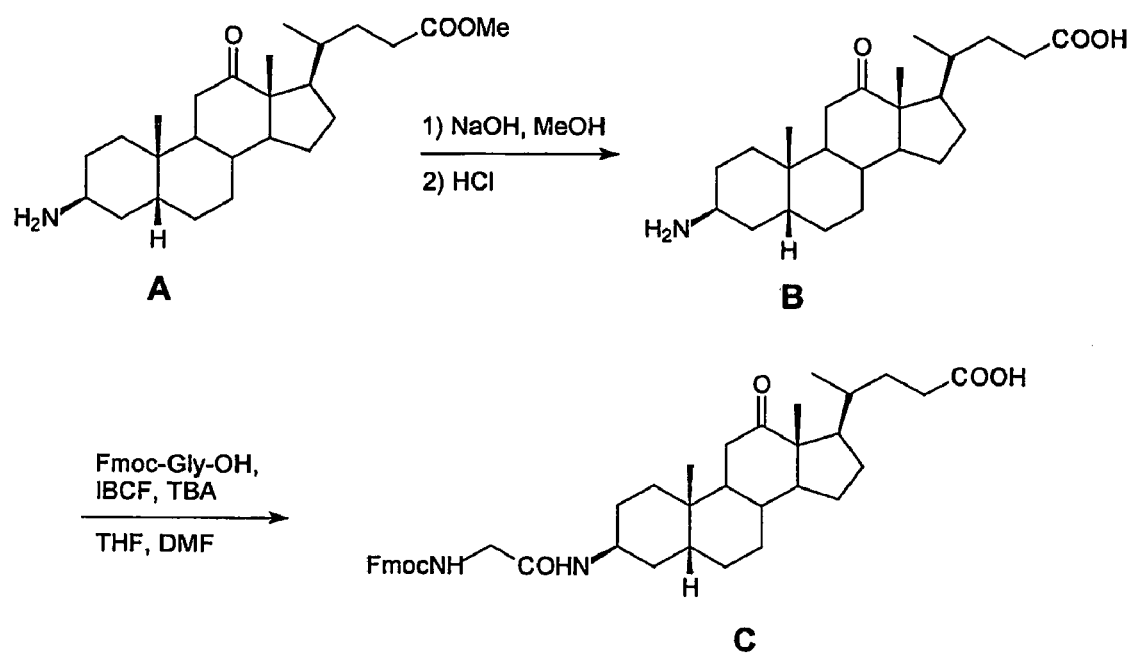
FIG. 7A is a graphical representation of a series of chemical reactions for the synthesis of intermediate (3β,5β)-3-[[(9H-Fluoren-9-ylmethoxy)amino]acetyl]amino-12-oxocholan-24-oic acid (C), as described in Example IX.

A. Synthesis (3β,5β-3-Amino-12-oxocholan-24-oic acid, (B)(FIG. 7A)

A 1 M solution of NaOH (6.6 mL; 6.6 mmol) was added dropwise to a solution of (3β,5β)-3-amino-12-oxocholan-24-oic acid methyl ester A (2.1 g; 5.1 mmol) in MeOH (15 mL) at 45° C. After 3 h stirring at 45° C., the mixture was concentrated to 25 mL then H₂O (25 mL) and 1 M HCl (8 mL) were added. The precipitated solid was filtered, washed with H₂O (2×30 mL) and vacuum dried to give B as a white solid (1.7 g; 4.4 mmol). Yield 88%.

B. Synthesis of (3β,5β)-3-[[(9H-Fluoren-9-ylmethoxy)amino]acetyl]amino-12-oxocholan-24-oic acid (C)(FIG. 7A)

Tributylamine (0.7 mL; 3.1 mmol) was added dropwise to a solution of N-α-Fmoc-glycine (0.9 g; 3.1 mmol) in THF (25 mL) stirred at 0° C. Isobutyl chloroformate (0.4 mL; 3.1 mmol) was subsequently added and, after 10 min, a suspension of tributylamine (0.6 mL; 2.6 mmol) and (3β,5β)-3-amino-12-oxocholan-24-oic acid B (1.0 g; 2.6 mmol) in DMF (30 mL) was added dropwise, over 1 h, into the cooled solution. The mixture was allowed to warm up and after 6 h the solution was concentrated to 40 mL, then H₂O (50 mL) and 1 N HCl (10 mL) were added (final pH: 1.5). The precipitated solid was filtered, washed with H₂O (2×50 mL), vacuum dried and purified by flash chromatography to give C as a white solid (1.1 g; 1.7 mmol). Yield 66%.

Figure 7B:
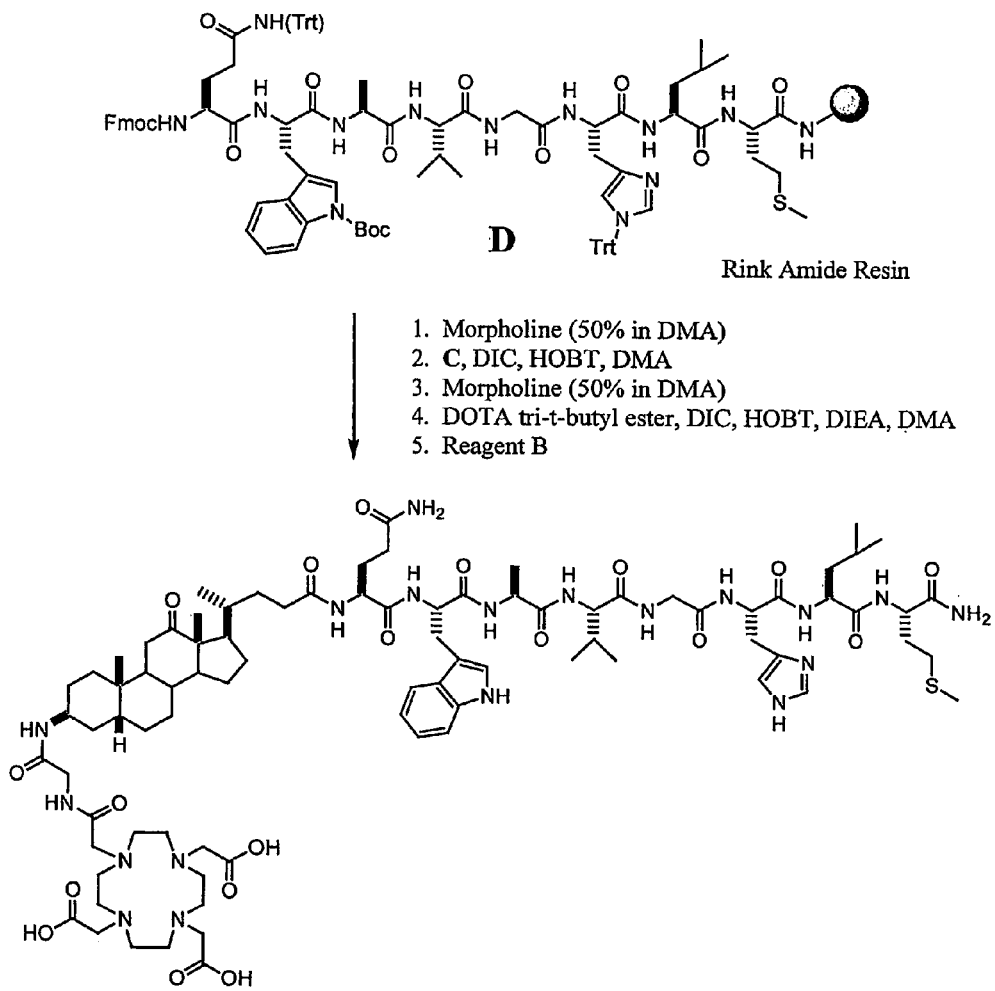
FIG. 7B is a graphical representation of the sequential reaction for the synthesis of N-[(3β,5β)-3-[[[[4,7,10-Tris (carboxymethyl)-1,4,7,10-tetraazacyclododec-1-yl]acetyl]amino]acetyl]amino]-12,24-dioxocholan-24-yl]-L-glutaminyl-L-tryptophyl-L-alanyl-L-valyl-glycyl-L-histidyl-L-leucyl-L-methioninamide (L67), as described in Example
Figure 7C:
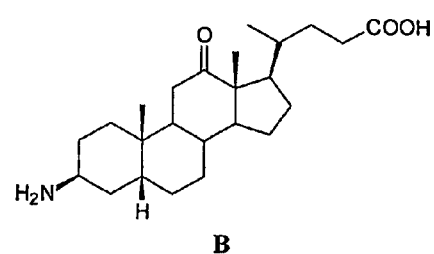
FIG. 7C is a chemical structure of (3β,5β)-3-Amino-12-oxocholan-24-oic acid (B), as described in Example IX.
Figure 7D:
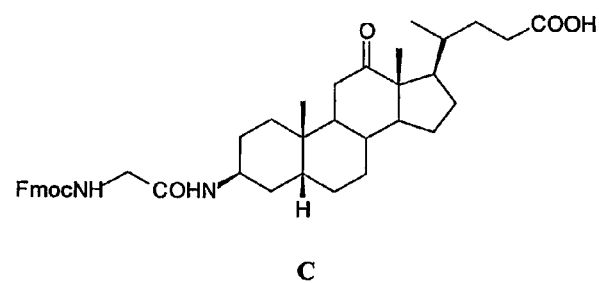
FIG. 7D is a chemical structure of (3β,5β)-3-[[(9H-Fluoren-9-ylmethoxy)amino]acetyl]amino-12-oxocholan-24-oic acid (C), as described in Example IX.
Figure 7E:
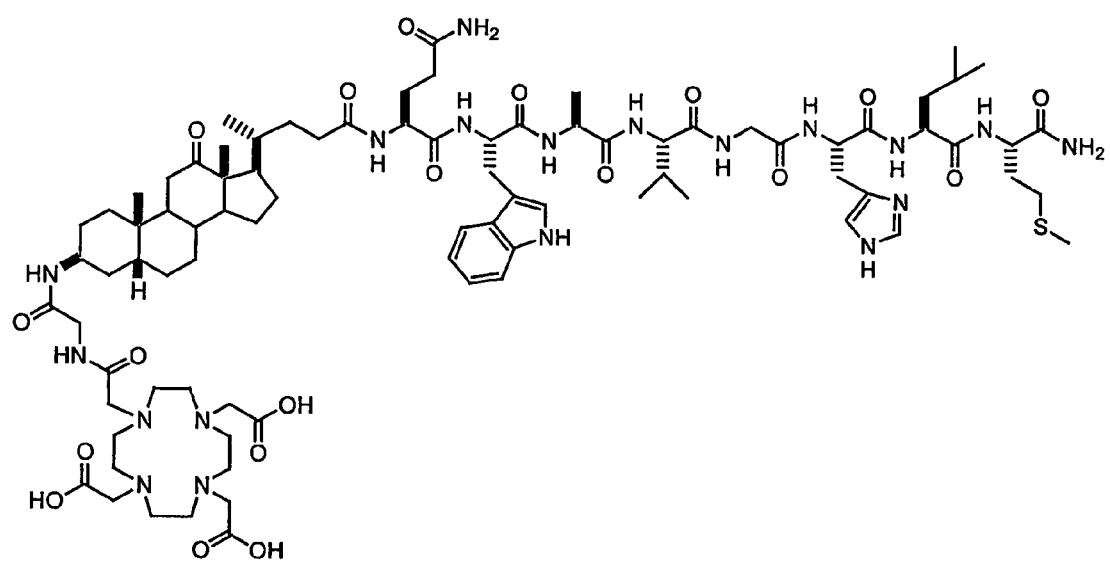
FIG. 7E is a chemical structure of N-[(3β,5β)-3-[[[[4,7,10-Tris(carboxymethyl)-1,4,7,10-tetraazacyclododec-1-yl]acetyl]amino]acetyl]amino]-12,24-dioxocholan-24-yl]-L-glutaminyl-L-tryptophyl-L-alanyl-L-valyl-glycyl-L-histidyl-L-leucyl-L-methioninamide (L67), as described in Example IX.

C. Synthesis of L67 (N-[3β,5β)-3-[[[[[4,7,10-Tris (carboxymethyl)-1,4,7,10-tetraazacyclododec-1-yl] acetyl]amino]acetyl]amino]-12,24-dioxocholan-24-yl]-L-glutaminyl-L-trwptophyl-L-alanyl-L-valyl-glycyl-L-histidyl-L-leucyl-L-methioninamide) (FIGS. 7B and 7E).

Resin D (0.5 g; 0.3 mmol) was shaken in a solid phase peptide synthesis vessel with 50% morpholine in DMA (7 mL) for 10 min, the solution was emptied and fresh 50% morpholine in DMA (7 mL) was added. The suspension was stirred for 20 min then the solution was emptied and the resin was washed with DMA (5×7 mL). (3β,5β)-3-[[(9H-Fluoren-9-ylmethoxy)amino]acetyl] amino]-12-oxocholan-24-oic acid C (0.80 g; 1.2 mmol), N-hydroxybenzotriazole (HOBT) (0.18 g; 1.2 mmol), N,N'-diisopropylcarbodiimide (DIC) (0.19 mL; 1.2 mmol) and DMA (7 mL) were added to the resin, the mixture was shaken for 24 h at room temperature, the solution was emptied and the resin was washed with DMA (5×7 mL). The resin was shaken with 50% morpholine in DMA (7 mL) for 10 min, the solution was emptied, fresh 50% morpholine in DMA (7 mL) was added and the mixture was shaken for 20 min. The solution was emptied and the resin washed with DMA (5×7 mL). 1,4,7,10-Tetraazacyclododecane-1,4,7,10-tetraacetic acid tris(1,1-dimethylethyl) ester adduct with NaCl (0.79 g; 1.2 mmol), HOBT (0.18 g; 1.2 mmol), DIC (0.19 mL: 1.2 mmol), DEEA (0.40 mL; 2.4 mmol) and DMA (7 mL) were added to the resin. The mixture was shaken for 24 h at room temperature, the solution was emptied and the resin was washed with DMA (5×7 mL), $CH_2Cl_2$ (5×7 mL) and vacuum dried. The resin was shaken in a flask with reagent B (25 mL) for 4.5 h. The resin was filtered and the solution was evaporated under reduced pressure to afford an oily crude that was triturated with $Et_2O$ (20 mL). L67 comprises a diagnostic moiety (a metal chelator) attached to a cholic acid derivative linker, which is attached to a targeting peptide (BBN[7-14]).

Example X

FIGS. 8A-H

Synthesis of L63 and L64

Summary: Hydrolysis of (3β,5β,7α,12α)-3-amino-7,12-dihydroxycholan-24-oic acid methyl ester 1b with NaOH gave the intermediate 2b, which was then reacted with Fmoc-glycine to give 3b. Rink amide resin functionalised with the octapeptide Gln-Trp-Ala-Val-Gly-His-Leu-Met-$NH_2$ (BBN [7-14] [SEQ ID NO:1]) was reacted with 3b and then with DOTA tri-t-butyl ester. After cleavage and deprotection with reagent B the crude was purified by preparative HPLC to give L64. The same procedure was repeated starting from intermediate 2a, already available, to give L63. Overall yields: 9 and 4%, respectively.

A. Synthesis of (3β,5β,7α, 12α)-3-Amino-7,12-dihydroxycholan-24-oic acid. (2b)(FIG. 8A)

A 1 M solution of NaOH (130 mL; 0.13 mol) was added dropwise to a solution of (3β,5β,7α,12α)-3-amino-7, 12-dihydroxycholan-24-oic acid methyl ester 1b (42.1 g; 0.10 mol) in MeOH (300 mL) heated at 45° C. After 3 h stirring at 45° C., the mixture was concentrated to 150 mL and $H_2O$ (350 mL) was added. After extraction with $CH_2Cl_2$ (2×100 mL) the aqueous solution was concentrated to 200 mL and 1 M HCl (150 mL) was added. The precipitated solid was filtered, washed with $H_2O$ (2×100 mL) and vacuum dried to give 2b as a white solid (34.8 g; 0.08 mol). Yield 80%.

B. Synthesis of (3β, 5β,12α)-3-[[(9H-Fluoren-9-ylmethoxy)amino]acetyl]amino-12-hydroxycholan-24-oic acid. (3a) (FIG. 8A)

Tributylamine (4.8 mL; 20.2 mmol) was added dropwise to a solution of N-α-Fmoc-glycine (6.0 g; 20.2 mmol) in TIE (120 mL) stirred at 0° C. Isobutyl chloroformate (2.6 mL; 20.2 mmol) was subsequently added and, after 10 min, a suspension of tributylamine (3.9 mL; 16.8 mmol) and (3β,5β,12α)-3-amino-12-hydroxycholan-24-oic acid 2a (6.6 g; 16.8 mmol) in DMF (120 mL) was added dropwise, over 1 h, into the cooled solution. The mixture was allowed to warm up and after 6 h the solution was concentrated to 150 mL, then $H_2O$ (250 mL) and 1 N HCl (40 mL) were added (final pH: 1.5). The precipitated solid was filtered, washed with $H_2O$ (2×100 mL), vacuum dried and purified by flash chromatography to give 3a as a white solid (3.5 g; 5.2 mmol). Yield 31%.

C. Synthesis of (3β,5β,7α,12α)-3-[[(9H-Fluoren-9-ylmethoxy)amino]acetyl]amino-7,12-dihydroxycholan-24-oic acid, (3b) (FIG. 8B)

Tributylamine (3.2 mL; 13.5 mmol) was added dropwise to a solution of N-α-Fmoc-glycine (4.0 g; 13.5 mmol) in THF (80 mL) stirred at 0° C. Isobutyl chloroformate (1.7 mL; 13.5 mmol) was subsequently added and, after 10 min, a suspension of tributylamine (2.6 mL; 11.2 mmol) and (3β,5β,7α,12α)-3-amino-7,12-dihydroxycholan-24-oic acid 3a (4.5 g; 11.2 mmol) in DMF (80 mL) was added dropwise, over 1 h, into the cooled solution. The mixture was allowed to warm up and after 6 h the solution was concentrated to 120 mL, then $H_2O$ (180 mL) and 1 N HCl (30 mL) were added (final pH: 1.5). The precipitated solid was filtered, washed with $H_2O$ (2×100 mL), vacuum dried and purified by flash chromatography to give 3a as a white solid (1.9 g; 2.8 mmol). Yield 25%.

In an alternative method, (3β,5β,7α,12α)-3-[[(9H-Fluoren-9-ylmethoxy)amino]acetyl]amino-7,12-dihydroxycholan-24-oic acid, (3b) can be prepared as follows:

N-Hydroxysuccinimide (1.70 g, 14.77 mmol) and DIC (1.87 g, 14.77 mmol) were added sequentially to a stirred solution of Fmoc-Gly-OH (4.0 g, 13.45 mmol) in dichloromethane (15 mL); the resulting mixture was stirred at room temperature for 4 h. The N,N'-diisopropylurea formed was removed by filtration and the solid was washed with ether (20 mL). The volatiles were removed and the solid Fmoc-Gly-succinimidyl ester formed was washed with ether (3×20 mL). Fmoc-Gly-succinimidyl ester was then redissolved in dry DMF (15 mL) and 3-aminodeoxycholic acid (5.21 g, 12.78 mmol) was added to the clear solution. The reaction mixture was stirred at room temperature for 4 h, water (200 mL) was added and the precipitated solid was filtered, washed with water, dried and purified by silica gel chromatography (TLC (silica): ($R_f$: 0.50, silica gel, $CH_2Cl_2/CH_3OH$, 9:1) (eluant: $CH_2Cl_2/CH_3OH$ (9:1) to give (3β,5β,7α, 12α)-3-[[(9H-Fluoren-9-ylmethoxy)amino]acetyl] amino-7,12-dihydroxycholan-24-oic acid, (3b) as a colorless solid. Yield: 7.46 g (85%).

D. Synthesis of L63 (N-[(3β,5β, 12α)-3-[[[[4,7,10-Tris(carboxymethyl)-1,4,7,10-tetraazacyclododec-1-yl]acetyl]amino]acetyl]amino]-12-hydroxy-24-oxo-cholan-24-yl]-L-glutaminyl-L-tryptophyl-L-alanyl-L-valyl-glycyl-L-histidvl-L-leucvl-L-methioninamide) (FIGS. 8B and 8G)

Resin A (0.5 g; 0.3 mmol) was shaken in a solid phase peptide synthesis vessel with 50% morpholine in DMA (7 mL) for 10 min, the solution was emptied and fresh 50% morpholine in DMA (7 mL) was added. The suspension was stirred for 20 min then the solution was emptied and the resin washed with DMA (5×7 mL). (3β,5β,12α)-3-[[(9H-Fluoren-9-ylmethoxy)amino] acetyl]amino-12-hydroxycholan-24-oic acid 3a (0.82 g; 1.2 mmol), N-hydroxybenzotriazole (HOBI) (0.18 g; 1.2 mmol), N,N'-diisopropylcarbodiimide (DIC) (0.19 mL; 1.2 mmol) and DMA (7 mL) were added to the resin, the mixture was shaken for 24 h at room temperature, the solution was emptied and the resin was washed with DMA (5×7 mL). The resin was then shaken with 50% morpholine in DMA (7 mL) for 10 min, the solution was emptied, fresh 50% morpholine in DMA (7 mL) was added and the mixture was shaken for 20 min. The solution was emptied and the resin washed with DMA (5×7 mL). 1,4,7,10-Tetraazacyclododecane-1,4,7,10-tetraacetic acid tris(1,1-dimethylethyl) ester adduct with NaCl (0.79 g; 1.2 mmol), HOBT (0.18 g; 1.2 mmol), DIC (0.19 mL: 1.2 mmol), DIEA (0.40 mL; 2.4 mmol) and DMA (7 mL) were added to the resin. The mixture was shaken for 24 h at room temperature, the solution was emptied and the resin washed with DMA (5×7 mL), CH$_2$Cl$_2$ (5×7 mL) and vacuum dried. The resin was shaken in a flask with reagent B (25 mL) for 4 h. The resin was filtered and the solution was evaporated under reduced pressure to afford an oily crude that after treatment with Et$_2$O (5 mL) gave a precipitate. The precipitate was collected by centrifugation and washed with Et$_2$O (5×5 mL), then analysed and purified by HPLC. The fractions containing the product were lyophilised to give L63 as a white fluffy solid (12.8 mg; 0.0073 mmol). Yield 9%. L63 comprises a diagnostic moiety (a metal chelator) attached to a cholic acid derivative linker, which is attached to a targeting peptide (BBN[7-14]).

E. Synthesis of L64 (N-[(3β,5β,7α,12α)-3-[[[[[4,7,10-Tris(carboxymethyl)-1,4,7,10-tetraazacyclododec-1-yl] acetyl]amino]acetyl]amino]-7,12-dihydroxy-24-oxocholan-24-yl]-L-glutaminyl-L-tryptophyl-L-alanyl-L-valyl-glycyl-L-histidyl-L-leucyl-L-methioninamide) (FIGS. 8C and 8H)

Resin A (0.5 g; 0.3 mmol) was shaken in a solid phase peptide synthesis vessel with 50% morpholine in DMA (7 mL) for 10 min, the solution was emptied and fresh 50% morpholine in DMA (7 mL) was added. The suspension was stirred for 20 min, the solution was emptied and the resin was washed with DMA (5×7 mL). (3β,5β,7α,12α)-3-[[(9H-Fluoren-9-ylmethoxy)amino]acetyl] amino-7,12-dihydroxycholan-24-oic acid 3b (0.81 g; 1.2 mmol), HOBT (0.18 g; 1.2 mmol), DIC (0.19 mL; 1.2 mmol) and DMA (7 mL) were added to the resin, the mixture shaken for 24 h at room temperature, the solution was emptied and the resin washed with DMA (5×7 mL). The resin was shaken with 50% morpholine in DMA (7 mL) for 10 min, the solution was emptied, fresh 50% morpholine in DMA (7 mL) was added and the mixture was shaken for 20 min. The solution was emptied and the resin was washed with DMA (5×7 mL). 1,4,7,10-Tetraazacyclododecane-1,4,7,10-tetraacetic acid tris(1,1-dimethylethyl) ester adduct with NaCl (0.79 g; 1.2 mmol), HOBT (0.18 g; 1.2 mmol), DIC (0.19 mL: 1.2 mmol), DIEA (0.40 mL; 2.4 mmol) and DMA (7 mL) were added to the resin. The mixture was shaken for 24 h at room temperature, the solution was emptied and the resin washed with DMA (5×7 mL), CH$_2$Cl$_2$ (5×7 mL) and vacuum dried. The resin was shaken in a flask with reagent B (25 mL) for 4 h. The resin was filtered and the solution was evaporated under reduced pressure to afford an oily crude that was triturated with Et$_2$O (5 mL). The precipitate was collected by centrifugation and washed with Et$_2$O (5×5 mL). Then it was dissolved in H$_2$O (20 mL), and Na$_2$CO$_3$ (0.10 g; 0.70 mmol) was added; the resulting mixture was stirred 4 h at room temperature. This solution was purified by HPLC, the fractions containing the product lyophilised to give L64 as a white fluffy solid (3.6 mg; 0.0021 mmol). Yield 4%. L64 comprises a diagnostic moiety (a metal chelator) attached to a cholic acid derivative linker, which is attached to a targeting peptide (BBN[7-14]).

Example XI

Preparation of $^{177}$Lu-L64 for Cell Binding and Biodistribution Studies

This compound was synthesized by incubating 10 µg L64 ligand (10 µL of a 1 mg/mL solution in water), 100 µL ammonium acetate buffer (0.2M, pH 5.2) and ~1-2 mCi of $^{177}$LuCl$_3$ in 0.05N HCl (MURR) at 90° C. for 15 min. Free $^{177}$Lu was scavenged by adding 20 µL of a 1% Na$_2$EDTA.2H$_2$O (Aldrich) solution in water. The resulting radiochemical purity (RCP) was ~95%. The radiolabeled product was separated from unlabeled ligand and other impurities by HPLC, using a YMC Basic C8 column [4.6×150 mm], a column temperature of 30° C. and a flow rate of 1 mL/min. with a gradient of 68% A/32% B to 66% A/34% B over 30 min., where A is citrate buffer (0.02M, pH 3.0), and B is 80% CH$_3$CN/20% CH$_3$OH. The isolated compound had an RCP of ~100% and an HPLC retention time of 23.4 minutes.

Samples for biodistribution and cell binding studies were prepared by collecting the desired HPLC peak into 1000 µL of citrate buffer (0.05 M, pH 5.3, containing 1% ascorbic acid, and 0.1% HSA). The organic eleunt in the collected eluate was removed by centrifugal concentration for 30 min. For cell binding studies, the purified sample was diluted with cell-binding media to a concentration of 1.5 µCi/mL within 30 minutes of the in vitro study. For biodistribution studies, the sample was diluted with citrate buffer (0.05 M, pH 5.3, containing 1% sodium ascorbate and 0.1% HSA) to a final concentration of 50 µCi/mL within 30 minutes of the in vivo study.

Example XII

Preparation of $^{177}$Lu-L64 for Radiotherapy Studies

This compound was synthesized by incubating 70 µg L64 ligand (70 µL of a 1 mg/mL solution in water), 200 µL ammonium acetate buffer (0.2M, pH 5.2) and ~30-40 mCi of $^{177}$LuCl$_3$ in 0.05N HCl (MURR) at 85° C. for 10 min. After cooling to room temperature, free $^{177}$Lu was scavenged by adding 20 µL of a 2% Na$_2$EDTA.2H$_2$O (Aldrich) solution in water. The resulting radiochemical purity (RCP) was ~95%. The radiolabeled product was separated from unlabeled ligand and other impurities by HPLC, using a 300VHP Anion Exchange column (7.5×50 mm) (Vydac) that was sequentially eluted at a flow rate of 1 mL/min with water, 50% acetonitrile/water and then 1 g/L aqueous ammonium acetate solution. The desired compound was eluted from the column with 50% CH$_3$CN and mixed with ~1 mL of citrate buffer (0.05 M, pH 5.3) containing 5% ascorbic acid, 0.2% HSA, and 0.9% (v:v) benzyl alcohol. The organic part of the isolated fraction was removed by spin vacuum for 40 min, and the concentrated solution (~20-25 mCi) was adjusted within 30 minutes of the in vivo study to a concentration of 7.5 mCi/mL using citrate buffer (0.05 M, pH 5.3) containing 5% ascorbic acid, 0.2% HSA, and 0.9% (v:v) benzyl alcohol. The resulting compound had an RCP of >95%.

Example XIII

Preparation of $^{111}$In-L64

This compound was synthesized by incubating 10 µg L64 ligand (5 µL of a 2 mg/mL solution in 0.01 N HCl), 60 µL ethanol, 1.12 mCi of $^{111}$InCl$_3$ in 0.05N HCl (80 µL) and 155 µL sodium acetate buffer (0.5M, pH 4.5) at 85° C. for 30 min. Free $^{111}$In was scavenged by adding 20 µL of a 1% Na$_2$EDTA.2H$_2$O (Aldrich) solution in water. The resulting radiochemical purity (RCP) was 87%. The radiolabeled product was separated from unlabeled ligand and other impurities by HPLC, using a Vydac C18 columns [4,6×250 mm], a column temperature of 50° C. and a flow rate of 1.5 mL/min. with a gradient of 75% A/25% B to 65% A/35% B over 20 min where A is 0.1% TFA in water, B is 0.085% TFA in acetonitrile. With this system, the retention time for $^{111}$n-L64 is 15.7 min. The isolated compound had an RCP of 96.7%.

Example XIV

Preparation of $^{177}$Lu-L63

A stock solution of peptide was prepared by dissolving L63 ligand (prepared as described in US Application Publication No. 2002/0054855 and WO 02/87637, both incorporated by reference) in 0.01 N HCl to a concentration of 1 mg/mL. $^{177}$Lu-L63 was prepared by mixing the following reagents in the order shown.

| | |
|---|---|
| 0.2 M NH$_4$OAc, pH 6.8 | 100 µl |
| Peptide stock, 1 mg/mL, in 0.01 N HCl | 5 µl |
| $^{177}$LuCl$_3$ (MURR) in 0.05 M HCl | 1.2 µl (1.4 mCi) |

The reaction mixture was incubated at 85° C. for 10 min. After cooling down to room temperature in a water bath, 20 µl of a 1% EDTA solution and 20 µl of EtOH were added. The compound was analyzed by HPLC using a C18 column (VYDAC Cat # 218TP54) that was eluted at flow rate of 1 mL/min with a gradient of 30-34% B over 20 min (where solvent is A. 0.1% TFA/H$_2$O and B is 0.1% TFA/CH$_3$CN). The $^{177}$Lu-L63 that formed had an RCP of 97.8% and a retention time of 14.2 min on this system.

Example XV

Relaxivity and HSA Binding of Gd-L64—FIGS. 11A-C

Gd-L64 displays a relaxivity in HEPES of about 10.45 mM$^{-1}$s$^{-1}$, which is consistent with the expected value based on molecular weight.

As shown in FIG. 11A, titration of a HEPES solution of Gd-L64 with HSA shows relatively strong binding (K$_a$=1.2× 10$^4$M$^{-1}$; R$_b$=20 mM$^{-1}$s$^{-1}$). Fitting the experimental curve yields a K$_a$ value of 1.2×10$^4$ M$^{-1}$ and a relaxivity of the fully bound species of about 20 mM$^{-1}$s$^{-1}$.

As shown in FIG. 11B, binding of Gd-L64 to HSA is confirmed by comparing NMRD profiles in HEPES and in serum, where the characteristic peak of bound species at frequencies of 10-30 MHz is seen in the presence of HAS. These results indicate that compounds containing linkers of the invention bind to HAS despite the absence of a free carboxylic acid at the 24 position.

Example XVI

In Vivo Pharmacokinetic Studies

A. Tracer Dose Biodistribution:
Low dose pharmacokinetic studies (e.g., biodistribution studies) were performed using the below-identified compounds of the invention and L 134, a control, in xenografted, PC3 tumor-bearing mice ([Ncr]-Foxn1<nu>). L134 is DO3A monoatnide-aminooctanyl-BBN[7-14]. In all studies, mice were administered 100 µL of $^{177}$Lu-labelled test compound at 200 µCi/kg, i.v., with a residence time of 1 and 24 h per group (n=3-4). Tissues were analyzed in an LKB 1282 CompuGamma counter with appropriate standards.

TABLE 2

Pharmacokinetic comparison at 1 and 24 h in PC3 tumor-bearing nude mice (200 µCi/kg; values as % ID/g) of Lu-177 labelled compounds of the invention compared to control

| | L134 | | L63 | | L64 | |
|---|---|---|---|---|---|---|
| Tissue | 1 hr | 24 hr | 1 hr | 24 hr | 1 hr | 24 hr |
| Blood | 0.44 | 0.03 | 7.54 | 0.05 | 1.87 | 0.02 |
| Liver | 0.38 | 0.04 | 12.15 | 0.20 | 2.89 | 0.21 |
| Kidneys | 7.65 | 1.03 | 7.22 | 0.84 | 10.95 | 1.45 |
| Tumor | 3.66 | 1.52 | 9.49 | 2.27 | 9.83 | 3.60 |
| Pancreas | 28.60 | 1.01 | 54.04 | 1.62 | 77.78 | 6.56 |

Whereas the distribution of radioactivity in the blood, liver and kidneys after injection of L64 is similar to that of the control compound, L134, the uptake in the tumor is much higher at 1 and 24 h for L64. L63 also shows high tumour uptake although with increased blood and liver values at early times. Uptake in the mouse pancreas, a normal organ known to have GRP receptors is much higher for L64 and L63 than for L134.

Example XVII

Radiotherapy Studies—FIGS. 12A-B

A. Short Term Efficacy Studies:
Radiotherapy studies were performed using the PC3 tumor-bearing nude mouse model. Lu-177 labelled compounds of the invention L64, L63 and the treatment control compound L134 were compared to an untreated control group. (n=12 for each treatment group and n=36 for the untreated control group). For the first study, mice were administered 100 µL of $^{177}$Lu-labelled compound of the invention at 30 mCi/kg, i.v, or s.c. under sterile conditions. The subjects were housed in a barrier environment for up to 30 days. Body weight and tumor size (by caliper measurement) were collected on each subject 3 times per week for the duration of the study. Criteria for early termination included: death; loss of total body weight (TBW) equal to or greater than 20%; tumor size equal to or greater than 2 cm$^3$. Results are displayed in FIG. 12A. These results show that animals treated with L64 or L63 have increased survival over the control animals given no treatment and over those animals given the same dose of L134.

A repeat study was performed with L64 using the same dose as before but using more animals per compound (n=46) and following them for longer. The results of the repeat study are displayed in FIG. 12B. Relative to the same controls as before (n=36), L64 treatment gave significantly increased survival (p<0.0001).

Example XVIII

Synthesis of LHRH Peptides

Linear peptides were synthesized using an Applied Biosystems Peptide Synthesizer, model 433A. Fmoc-Pal-Peg-PS resin was used for peptide synthesis, applying an orthogonal Fmoc strategy. The amino side chains were protected with trityl- (for His), t-butyl-(for Ser and Tyr), boc-(for Trp), methyltrityl-(for D-Lys) and Pmc- (for Arg) groups. Cleavage of the peptides and workup were performed as follows: Treatment of the resin loaded with the peptide of interest with 88% trifluoroacetic acid (TFA)/5% ophenol/5% water/2% triisopropylsilane (TIS) (reagent 'B') at room temperature for 4 h and subsequent evaporation and precipitation in diethyl ether provided crude peptide. The off-colored white solid was then dissolved in water, filtered and purified by HPLC using a Shimadzu System with a reversed phase C-18 column (YMC-Pack ODS/A column) employing water and acetonitrile with 0.1% TFA as eluents.

A. Synthesis of Fmoc-Gly-3-Aminodeoxycholic Acid (3β,5β,7α,12α)-3 [[9H-Fluoren-9-ylmethoxy)amino]acetyl]amino-7-12-dihydroxycholan-24-oic acid To a solution of Fmoc-Gly-OH (4.0 g, 13.45 mmol) in dichloromethane (15 mL) was added N-hydroxysuccinimide (1.70 g, 14.77-mmol) followed by DIC (diisopropyl-carbodiimide) (1.87 g, 14.77 mmol) and stirred at room temperature for 4 h. The urea formed was removed by filtration and washed the solid with ether (20 mL). The combined filtrate was evaporated on a rotary evaporator to remove the solvent and the solid, Fmoc-Gly-succinimidyl ester, formed was washed with ether (3×20 mL). Fmoc-Gly-succinimidyl ester was then redissolved in dry DMF (15 mL) and 3-aminodeoxycholic acid (5.21 g, 12.78 mmol) was then added to the clear solution. After stirring the reaction mixture at room temperature for 4 h, the mixture was added to water (200 mL) and the precipitated solid was filtered, washed with water, dried and purified by silica gel chromatography ($R_f$: 0.50, silica gel, $CH_2Cl_2/CH_3OH$, 9:1) (eluant: $CH_2Cl_2/CH_3OH$ (9:1) to give Fmoc-Gly-3-aminodeoxycholic acid as a colorless solid. Yield: 7.46 g (85%).
MS (API-ES, +ve ion): 710.2 (M+Na), 687.7 (M+H).

B. Pyr-YH's-Trp-Ser-Tyr-DLys(DOTA-Gly-Adca3)-Leu-Arg-Pro-Gly-$NH_2$

To a solution of Fmoc-Gly-3-aminodeoxycholic acid (20 mg, 0.029 mmol) in dichloromethane (0.2 mL) was added N-hydroxysuccinimide (4.0 mg, 0.035 mmol) followed by DIC (diisopropylcarbodiimide) (5.0 mg, 0.039 mmol) and stirred at room temperature for 4 h. After evaporation of the solvent, the solid was washed with diethyl ether (5×1.0 mL) and dried. Solid of Fmoc-Gly-3-aminodeoxycholic acid succinimidyl ester was then dissolved in dry DMF (0.5 mL) and to the clear solution was added pure H-Pyr-His-Trp-Ser-Tyr-DLys-Leu-Arg-Pro-Gly-$NH_2$ (30 mg, 0.024 mmol) and diisopropylethylamine (7.5 mg, 0.058 mmol), and stirred the reaction mixture at room temperature for 18 h. To reaction mixture, piperidine (0.1 mL) was added and stirred for 20 min to remove the Fmoc protecting group. Diluted with water, acidified the solution to pH 4.0 with TFA and loaded onto a YMC-Pack ODS/A, 30×250 mm column. Eluted the column employing water and acetonitrile with 0.1% TFA as eluents and collected the fractions containing the required peptide (based on MS results) and lyophilized to obtain pure Pyr-His-Trp-Ser-Tyr-DLys(H-Gly-Adca3)-Leu-Arg-Pro-Gly-$NH_2$ (15 mg, 41%) as a colorless fluffy solid. MS (API-ES, positive ion): 1700.4 (M+H), 851.5 [M+H]/2.

To the pre-activated solution of DOTA-tri-t-butyl ester (25.3 mg, 0.04 mmol), HBTU (15.2 mg, 0.04 mmol) and diisopropylethylamine (12 mg, 0.09 mmol) in dry DMF (0.2 mL) was added Pyr-His-Trp-Ser-Tyr-DLys(H-Gly-Adca3)-Leu-Arg-Pro-Gly-$NH_2$ (15 mg, 0.01 mmol)) and stirred the reaction mixture for 15 h. After evaporation of the solvent under vacuum, the residue was treated with TFA-anisole (95:5, 2 mL) for 5 h. After evaporation of the volatiles on a rotary evaporator, the peptide was precipitated by adding ether. The crude peptide was obtained by centrifugation, washed with ether and isolated the required peptide Pyr-His-Trp-Ser-Tyr-DLys(DOTA-Gly-Adca3)-Leu-Arg-Pro-Gly-$NH_2$ as a colorless solid. Yield: 12.5 mg (68%).
MS (API-ES, positive ion): 2086.5 (M+H), 1044.3 [M+H]/2

Example XIX

Preparation of $^{125}$I-labeled Compounds

Compounds of the invention can be labeld with a radioactive halogen such as, for example, $^{125}$I, $^{131}$I or $^{123}$I using labeling and purification procedures that are known to those skilled in the art or suitable modifications thereof. Typical procedures for labeling with radioiodine (or other radioactive halogens) using Bolton-Hunter Reagent, Lactoperoxidase, Iodogen and Chloramine T reagents are described by A. E. Bolton, Comparative Methods For The Radiolabeling Of Peptides, in "Methods in Enzymology", 1986, Vol. 124, p. 18-29. For example, the compounds of the present invention can be labeled with $^{125}$I by reacting the unlabeled compound in (e.g.) a small volume of borate buffer or DMF that has been previously adjusted to pH 8.5-9.0 using, for example, diisopropyl amine, with dried Bolton-Hunter reagent The vial is shaken and then incubated on ice for about 30 minutes with occasional shaking. After this time, the reaction can optionally be quenched with a solution of (e.g.) glycine and then purified using, for example, reversed phase HLPC to remove free labeled compound from impurities and from unlabeled compound. Alternatively, the compounds can be dissolved in phosphate buffer to a pH near 7, iodide (as Na$^{125}$I) can be added, and the solution treated with a buffered solution of Chloramine T to effect iodination, then treated with a reductant such as sodium meta bisulfite to quench the reaction. Free I$^-$ can be removed by ion exchange chromatography and unlabeled compound can be resolved from radiolabeled compound using HPLC methods such as C8 or C18 reversed phase chromatography.

Example XX

Synthesis of L69—FIGS. 13A and 13B

Summary: Reaction of (3β,5β,7α,12α)-3-amino-7,12-dihydroxycholan-24-oic acid A with Fmoc-Cl gave intermediate B. Rink amide resin functionalised with the octapeptide GlnTrpAlaValGlyHisLeuMetNH$_2$ (BBN[7-14]) (A), was sequentially reacted with B, Fmoc-8-amino-3,6-dioxaoctanoic acid and DOTA tri-t-butyl ester. After cleavage and deprotection with reagent B (2) the crude was purified by preparative HPLC to give L69. Overall yield: 4.2%.

A. (3β,5β,7α,12α)-3-(9H-Fluoren-9-ylmethoxy) amino-7,12-dihydroxycholan-24-oic acid, B (FIG. 13A)

A solution of 9-fluorenylmethoxycarbonyl chloride (1.4 g; 5.4 mmol) in 1,4-dioxane (18 mL) was added dropwise to a suspension of (3β,5β,7α,12α)-3-amino-7,12-dihydroxycholan-24-oic acid A (2.0 g; 4.9 mmol) (3) in 10% aq. Na$_2$CO$_3$ (30 mL) and 1,4-dioxane (18 mL) stirred at 0° C. After 6 h stirring at room temperature H$_2$O (100 mL) was added, the aqueous phase washed with Et$_2$O (2×90 mL) and then 2 M HCl (15 mL) was added (final pH: 1.5). The precipitated solid was filtered, washed with H$_2$O (3×100 mL), vacuum dried and then purified by flash chromatography (4) to give B as a white solid (2.2 g; 3.5 mmol). Yield 71%.

B. N-[(3β,5β,7α,12α)-3-[[[2-[2-[[[4,7,10-Tris(carboxymethyl)-1,4,7,10-tetraazacyclododec-1-yl] acetyl]amino]ethoxy]ethoxy]acetyl]amino]-7,12-dihydroxy-24-oxocholan-24-yl]-L-glutaminyl-L-tryptophyl-L-alanyl-L-valyl-glycyl-L-histidyl-L-leucyl-L-methioninamide, L69 (FIG. 13B)

Resin A (0.5 g; 0.3 mmol) (6) was shaken in a solid phase peptide synthesis vessel with 50% morpholine in DMA (7 mL) for 10 min, the solution flushed off and fresh 50% morpholine in DMA (7 mL) was added. The suspension was stirred for another 20 min then the solution was flushed off and the resin washed with DMA (5×7 mL). (3β,5β,7α,12α)-3-(9H-Fluoren-9-ylmethoxy)amino-7,12-dihydroxycholan-24-oic acid B (0.75 g; 1.2 mmol), N-hydroxybenzotriazole (HOBt) (0.18 g; 1.2 mmol), N,N'-diisopropylcarbodiimide (DIC) (0.19 mL; 1.2 mmol) and DMA (7 mL) were added to the resin, the mixture shaken for 24 h at room temperature, emptied and the resin washed with DMA (5×7 mL). The resin was then shaken with 50% morpholine in DMA (7 mL) for 10 min, the solution emptied, fresh 50% morpholine in DMA (7 mL) was added and the mixture shaken for another 20 min. The solution was emptied and the resin washed with DMA (5×7 mL). Fmoc-8-amino-3,6-dioxaoctanoic acid (0.79 g; 1.2 mmol) (7), HOBt (0.18 g; 1.2 mmol), DIC (0.19 mL; 1.2 mmol) and DMA (7 mL) were added to the resin. The mixture was shaken for 3 h at room temperature, emptied and the resin washed with DMA (5×7 mL). The resin was then shaken with 50% morpholine in DMA (7 mL) for 10 min, the solution flushed off, fresh 50% morpholine in DMA (7 mL) was added and the mixture shaken for another 20 min. The solution was flushed off and the resin washed with DMA (5×7 mL) 1,4,7, 10-Tetraazacyclododecane-1,4,7,10-tetraacetic acid tris(1,1-dimethylethyl) ester adduct with NaCl (0.79 g; 1.2 mmol), HOBt (0.18 g; 1.2 mmol), DIC (0.19 mL: 1.2 mmol), N-ethyldiisopropylamine (0.40 mL; 2.4 mmol) and DMA (7 mL) were added to the resin. The mixture was shaken for 24 h at room temperature, flushed off and the resin washed with DMA (5×7 mL), CH$_2$Cl$_2$ (5×7 mL) and vacuum dried. The resin was shaken in a flask with Reagent B (25 mL) (2) for 4.5 h. The resin was filtered and the solution was evaporated under reduced pressure to afford an oily crude that after treatment with Et$_2$O (20 mL) gave a precipitate. The precipitate was collected by centrifugation and washed with Et$_2$O (3×20 mL) to give a solid (248 mg) which was analysed by HPLC. An amount of crude (50 mg) was purified by preparative HPLC. The fractions containing the product were lyophilised to give L69 (6.5 mg; 3.5×10$^{-3}$ mmol) (FIG. 13B) as a white solid. Yield 5.8%.

Throughout the foregoing description of the invention, various patents, articles, and other publications have been cited or referenced. The entire contents of each patent, article and other publication is hereby incorporated by reference into the subject application.

What is claimed is:

1. A compound of the general formula:

M-N-O-P-Q wherein
M is a metal chelator;
N is absent, an alpha amino acid, a substituted bile acid or other linking group;
O is an alpha amino acid or a substituted bile acid; and
P is absent, an alpha amino acid, a substituted bile acid or other linking group; and
Q is a targeting peptide, and
wherein at least one of N, O or P is a substituted bile acid.

2. The compound of claim 1, wherein Q is a peptide hormone selected from the group consisting of luetinising hormone releasing hormone (LHRH), insulin, oxytosin, somatostatin, neuro kinin-1 (NK-1), vasoactive intestinal peptide (VIP), Substance P, neuropeptide Y (NPY), endothelin A, endothelin B, bradykinin, interleukin-1, epidural growth factor (EGF), cholecystokinin (CCK), galanan, MSH, Lanreotide, Octreotide, Maltose, arginine-vasopressin and analogues and derivatives thereof.

3. The compound of claim 1, wherein the substituted bile acid is selected from the group consisting of:
- (3β,5β)-3-aminocholan-24-oic acid;
- (3β,5β,12α)-3-amino-12-hydroxycholan-24-oic acid;
- (3β,5β,7α,12α)-3-amino-7,12-dihydroxycholan-24-oic acid;
- Lys(3,6,9)-trioxaundecane-1,11-dicarbonyl-3,7-dideoxy-3-aminocholic acid);
- (3β,5β,7α)-3-amino-7-hydroxy-12-oxocholan-24-oic acid; and
- (3β,5β,7α)-3-amino-7-hydroxycholan-24-oic acid.

4. A compound of the general formula:

M-N-O-P-Q wherein
- M is a metal chelator;
- N is absent, an alpha amino acid, a substituted bile acid or other linking group;
- O is an alpha amino acid or a substituted bile acid; and
- P is absent, an alpha amino acid, a substituted bile acid or other linking group; and
- Q is a luetinising hormone releasing hormone (LHRH) peptide or an analogue, and wherein at least one of N, O or P is a substituted bile acid.

5. A compound of claim 4, wherein Q is a luetinising hormone releasing hormone (LHRH) analogue of the formula:

PGlu-His-Trp-W-Tyr-DLys-X-Y-Pro-Z, wherein
- W=Ser, NMeSer, or Thr;
- X=Leu, NMeLeu, t-ButylGly;
- Y=Arg, Arg(Et2), Cit, Lys(isopropyl); and
- Z=Gly-NH$_2$, NHEthyl, Azagly-NH$_2$.

6. A compound of the general formula:

Glu-His-Trp-W-Tyr-DLys(M-N-O-P)-X-Y-Pro-Z, wherein
- M is a chelator;
- N is absent, an alpha amino acid, a substituted bile acid or other linking group;
- O is an alpha amino acid or a substituted bile acid; and
- P is absent, an alpha amino acid, a substituted bile acid or other linking group,
- W=Ser, NMeSer, or Thr.
- X=Leu, NMeLeu, t-ButylGly.
- Y=Arg, Arg(Et2), Cit, Lys(isopropyl).
- Z=Gly-NH$_2$, NHEthyl, Azagly-NH$_2$.
wherein at least one of N, O or P is a substituted bile amino acid.

7. The compound of claim 5, wherein M is 1, 4, 7, 10-tetraazacyclotetradecane-1, 4, 7, 10-tetraacetic acid (DOTA)-Gly.

8. The compound of claim 4 or 5, wherein the substituted bile acid is selected from the group consisting of:
- (3β,3β)-3-aminocholan-24-oic acid;
- (3β,5β,12α)-3-amino-12-hydroxycholan-24-oic acid;
- (3β,5β,7α,12α)-3-amino-7,12-dihydroxycholan-24-oic acid;
- Lys-(3,6,9)-trioxaundecane-1,11-dicarbonyl-3,7-dideoxy-3-aminocholic acid);
- (3β,5β,7α)-3-amino-7-hydroxy-12-oxocholan-24-oic acid; and
- (3β,5β,7α)-3-amino-7-hydroxycholan-24-oic acid.

9. A method of imaging comprising the steps of:
administering to a patient a diagnostic imaging agent comprising the compound of claim 1 wherein the chelator is complexed with a diagnostic radionuclide or a paramagnetic metal, and
imaging said patient.

10. A method of radiotherapy comprising the steps of:
administering to a patient a radiotherapeutic agent comprising the compound of claim 1 wherein the chelator is complexed with a therapeutic radionuclide, and
imaging said patient.

11. A method of imaging comprising the steps of:
administering to a patient a diagnostic imaging agent comprising the compound of claim 4 wherein the chelator is complexed with a diagnostic radionuclide or a paramagnetic metal, and
imaging said patient.

12. A method of radiotherapy comprising the steps of:
administering to a patient a radiotherapeutic agent comprising the compound of claim 4 wherein the chelator is complexed with a therapeutic radionuclide, and
imaging said patient.

13. A method of imaging comprising the steps of:
administering to a patient a diagnostic imaging agent comprising the compound of claim 6 wherein the chelator is complexed with a diagnostic radionuclide or a paramagnetic metal, and
imaging said patient.

14. A method of radiotherapy comprising the steps of:
administering to a patient a radiotherapeutic agent comprising the compound of claim 6 wherein the chelator is complexed with a therapeutic radionuclide, and
imaging said patient.

* * * * *

SEQUENCE LISTING

<160> NUMBER OF SEQ ID NOS: 1

<210> SEQ ID NO 1
<211> LENGTH: 8
<212> TYPE: PRT
<213> ORGANISM: Artificial
<220> FEATURE:
<223> OTHER INFORMATION: Description of Artificial Sequence: This
      peptide is known as bombesin (i.e., BBN (7-14)) and binds to
      gastrin releasing peptide (GRP) receptors.

<400> SEQUENCE: 1

Gln Trp Ala Val Gly His Leu Met
1               5